US 7,351,881 B2

United States Patent
Carozzi et al.

(10) Patent No.: US 7,351,881 B2
(45) Date of Patent: Apr. 1, 2008

(54) AXMI-008, A DELTA-ENDOTOXIN GENE AND METHODS FOR ITS USE

(75) Inventors: Nadine Carozzi, Raleigh, NC (US); Tracy Hargiss, Cary, NC (US); Michael G. Koziel, Raleigh, NC (US); Nicholas B. Duck, Apex, NC (US); Brian Carr, Raleigh, NC (US)

(73) Assignee: Athenix Corporation, Research Triangle Park, NC (US)

( * ) Notice: Subject to any disclaimer, the term of this patent is extended or adjusted under 35 U.S.C. 154(b) by 333 days.

(21) Appl. No.: 10/781,979

(22) Filed: Feb. 19, 2004

(65) Prior Publication Data

US 2004/0250311 A1    Dec. 9, 2004

Related U.S. Application Data

(60) Provisional application No. 60/448,797, filed on Feb. 20, 2003.

(51) Int. Cl.
*A01H 5/00* (2006.01)
*A01H 5/10* (2006.01)
*C12N 15/82* (2006.01)
*C12N 1/21* (2006.01)
*C12N 15/32* (2006.01)

(52) U.S. Cl. .................. 800/302; 435/418; 435/252.3; 435/320.1; 424/93.2; 536/23.71

(58) Field of Classification Search .................. None
See application file for complete search history.

(56) References Cited

U.S. PATENT DOCUMENTS 6,833,449 B1 * 12/2004 Barton et al. ............ 536/23.71

OTHER PUBLICATIONS

Lazar et al, 1988, Mol. Cell. Biol. 8:1247-1252.*
Hill et al, 1998, Biochem. Biophys. Res. Comm. 244:573-577.*
Guo et al, 2004, Proc. Natl. Acad. Sci. USA 101: 9205-9210.*
de Maagd et al, 1999, Appl. Environ. Microbiol. 65:4369-4374.*
Tounsi et al, 2003, J. Appl. Microbiol. 95:23-28.*
Angsuthanasombat et al, 2001, J. Biochem. Mol. Biol. 34:402-407.*
Ibarra et al, 2003, Appl. Environ. Microbiol. 69:5269-5274.*
Aaronson et al, 2001, FEMS Microbiol. Lett. 195:1-8.*
de Maagd et al, 2001, Trends Genet. 17:193-199.*
Rosso, M-L., and Delécluse, A., "Contribution of the 65-Kilodalton Protein Encoded by the Cloned Gene *cry19A* to the Mosquitocidal Activity of *Bacillus thuringiensis* subsp. *jegathesan*," *Appl. Environ. Microbiol.*, Nov. 1997, pp. 4449-4455, vol. 63, No. 11.
NCBI Database Report for Accession No. BAB72017, Direct Submission on Nov. 14, 2001.
NCBI Database Report for Accession No. BAB72018, Direct Submission on Nov. 14, 2001.
NCBI Database Report for Accession No. BAB72019, Direct Submission on Nov. 14, 2001.

* cited by examiner

*Primary Examiner*—Anne Kubelik
(74) *Attorney, Agent, or Firm*—Alston & Bird LLP

(57) ABSTRACT

Compositions and methods for conferring pesticidal activity to bacteria, plants, plant cells, tissues and seeds are provided. Compositions comprising a coding sequence for a delta-endotoxin and delta-endotoxin-associated polypeptides are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin and delta-endotoxin-associated nucleic acid molecules are provided. Additionally, amino acid sequences corresponding to the polynucleotides are encompassed. In particular, the present invention provides for isolated nucleic acid molecules comprising nucleotide sequences encoding the amino acid sequences shown in SEQ ID NOS:3, 5, and 7, and the nucleotide sequences set forth in SEQ ID NO:1, 2, 4, and 6, as well as variants and fragments thereof.

14 Claims, 12 Drawing Sheets

```
                   *         20          *         40          *         60          *         80
axmi008   : ----VKKMSPYQNKMEYEILESSSNN---TNTPNRYPFANNRDMSTMSWNDCQGISWDEIWES-----------------------VE :  58
cry1Aa    : --------------------------------MDMNPNINECIPYMCLSNPEVEVLG-----G--ERIETGYTPI :  36
cry1Ac    : --------------------------------MDMNPNINECIPYMCLSNPEVEVLG-----G--ERIETGYTPI :  36
cry1Ia    : -----MKLKNQDKHQSFSSNAKVDKISTDS----LKNETDIELQNINHEDCLKMSEYEN------VEPFVSASTIQ :  61
cry2Aa    : --------------------------------MNNVLNSGRTTICDAYNVVAHDPFSFEHKSLDTIQKEWMEWKRTDHS--------L :  48
cry3Aa1   : MIRKGGRKMNPNNRSEHDTIKTTEMNEVPTNHVQYPLAETPNPTLEDLNYKEFLRMTADNN-----TEALDSSTTKDVIQ :  75
cry3Bb    : -----MNPNNRSEHDTIKVTPNSELQTMHNQYPLADNPNSTLEELNYKEFLRMTEDSS-----TEVLDNSTVKDAVG :  67
cry4Aa    : -----MNPYQNKMEYETLNASQKKLNISMNYTRYPIENSPKQLLQSTNYKDWLNMCQQNQ-QY--GGDFETFIDSGELS :  71
cry4Ba    : --------------------------------MNSGYPLANDLQGSMKNTNYKDWLAMCENNQ-QY--GVNPAAINSS-SV5 :  46
cry6Aa    : -----MIIDSKTTLPRHSLIHTIKLNSNKKYGPGDMTNGNQ---------FIISKQ :  42
cry7Aa    : -----MNLNNLDGYEDSNRTLN-----NSLNYPTQKALSPSLKNMNYQDFLSITEREQ-----PE--ALASGNTAIN :  60
cry8Aa    : -----MSPNNQNEYEIIDATPSTSVSSDSNRYPFANEPTDALQNMNYKDYLKMSGGENPEL--FGNPETFISSSTIQ :  70
cry10Aa   : -----MNPYQNKNEYEIFNAPSNGFSKSNNYSRYPLANKPNQPLKNTNYKDWLNVCQDNQYGMNAGNFASSETIVGV5 :  74
cry16Aa   : -----MHYYGNRNEYDILNASSNDSNMSNTYPRYPLANPQQDLMQNTNYKDWLNVCEGYHIEN--PR--EASVRAGLG :  69
cry19Ba   : -----MNSYQNKNEYEILDAKRNTCHMSNCYPKYPLANDPQMYLRNTHYKDWIMCEEASYAS-------S-----GPS :  62
cry24Aa   : -----MNQYQNKNEYEILESSQNN-----MNTPNRYPFADDPNAVMKNGNYKDWVNECEGSN---------ISPSPAAA :  60
cry25Aa   : -----MNPYQNKSECEILNAPLNN----INMPNRYPFANDPNAVMKNGNYKDWLNECDGITP-----SIFGTLG :  60
cry39Aa1  : -----NSYENKNEYEILNDSKKS-NMSNPYLRYPLANDSLASMQNTNYKDWLTMCDRTDTDV--LS-----SRGAVS :  64
cry40Aa1  : -----NSYENKNEYEILESSSNN---TNMPNRYPFANDRDMSTMSFNDCQGISWDEIWES----------------AE :  54
```

FIG. 1A

```
             *         100         *         120         *         140         *         160
axmi008  : TITSIGINLIEFVIEPSLGGINTLLSIIGKLIPTNRQ-TVS---ALSICDLLSIIRKEVADSVLSDAIA-DFDGKLKNYR : 133
cry1Ae   : DISLSLTQFLLSEFVPGAGFVLGLVDIIWGIFGPSQ--------WDAFPVQIEQLINQRIEEFARNQAIS--RLEGLSNLY : 107
cry1Ac   : DISLSLTQFLLSEFVPGAGFVLGLVDIIWGIFGPSQ--------WDAFLVQIEQLINQRIEEFARNQAIS--RLEGLSNLY : 107
cry1Ie   : TGIGIAGKILGTLGVPFAGQVASLYSFILGELWP-KG-KNQ--WEIFMEHVEEIINQKISTYARMKALT--DLKGLGDAL : 135
cry2Ae   : YVAPVVGTVSSFLLKKVGSLIGKRILSELWGIIFPSG--STNLMQDILRETEQFLNQRLNTDTLARVNA--ELIGLQANI : 124
cry3Ae1  : KGISVVGDLLGVVGFPPFGGALVSFYTNFLNTIWPS---EDP--WKAFMEQVEALMDQKIADYAKNKALA--ELQGLQNNV : 148
cry3Bb   : TGISVVGQILGVVGVPFAGALTSFYQSFLNTIWPSD--ADP--WKAFMAQVEVLIDKKIEEYAKSKALA--ELQGLQNNF : 141
cry4Ae   : AYTIWGTVLTGFGFTTPLGLALIGFGTLIPVLFPAQ-DQSNTUSDFITQTKNIIKKEIASTYISNAMK--ILNRSFNVI : 148
cry4Be   : TALKVAGAILKFVNPPAGTVLTVLSAVLPILWPTNTP-TPERVWNDFMTNTGNLIDQTVTAYVRTDANA--KMTVVKDYL : 123
cry6Ae   : EWATIGAYIQTGLGLPVNEQQLRTHVNLSQDISIPSDFSQLYDVYCSDKTSAEWWNKNLYPLIIKSAND-IASYGFKVAG : 121
cry7Ae   : TWVSVTGATLSALGVPGASFITNFYLKIAGLLWPEN--GKI--WDEFMTEVEALIDQKIEEYVRMKAIA--ELDGLGSAL : 134
cry8Ae   : TGIGIVGRILGALGVPFASQIASFYSFTVGQLWPSKS-VDI--WGEIMERVEELVDQKIEKYVKDKALA--ELKGLGNAL : 145
cry10Ae  : AGIIVVGTMLGAFAAPVLAAGIISFGTLIPIFWQGSDPAN---VWQDLLNIGGRPIQEIDKNIINVLTS--IVTPIKNQL : 149
cry16Ae  : KGLGIVSTIVGFFGGSIILDTIGLFYQISELLWPEDD-TQQYTWQDIMNHVEDLIDKRITEVIRGMAIR--TLADLQGKV : 146
cry19Be  : QLFKVGGSIVAKILG-MIPEVGPLLSWMVSLFWPTIE-EKNTVWEDMIKYVANLLKQELTNDTLNRATS--NLSGLNESL : 138
cry24Ae  : ITSKIVSIVLKTLAKAVASSLADSIKSSLGISKTITENNVS---QVSMVQVHQIINRRIQETILDLGES--SLNGLVAIYN : 136
cry25Ae  : VLASIVISTINLATSPSIGDAFALVSSIGEYWPETKT------SFPLSVADVNRLIREALDQNAINRATG-KFNGLMDTYN : 134
cry39Ae1 : TGVGMLSTILSLFGIPLIGEGIDLLLGAADFLWPESDGGHQYTWEDLMNHIEELMDERLETEKRTTALD--DLRGLKALL : 142
cry40Ae1 : TITSIGIDLIEFLMEPSLGGINTLFSIIGKLIPTNHQ-SVS---ALSICDLLSIIRKEVADSVLSDAICRFLDGKLKNYR : 130
```

FIG. 1B

```
                       *         180         *         200         *         220         *         240
axmi008    : EYYLSYLGAULKDGKPL-QKTMNSDIGQLVYYFKLSERDFNEILGGSLSRN----MAQVLLLPTFAQAANVQLLLLRDAV : 208
cry1Aa     : QIYAESFREWEADP------TNPALREEMRIQFNDMNSALTTAIPLLAVQ------NYQVPLLSVYVQAANLHLSVLRDVS : 176
cry1Ac     : QIYAESFREWEADP------TNPALREEMRIQFNDMNSALTTAIPLFAVQ------NYQVPLLSVYVQAANLHLSVLRDVS : 176
cry1Ia     : AVYHDSLESUVGN-------RNNTRARSVVKSQYIALELMFVQKLPSFAVS-----GEEVPLLPIYAQAANLHLLLRDAS  : 204
cry2Aa     : REFNQQVDNFLNP-------TQNPVPLSITSSVNTMQQLFLNRLPQFQIQG-----YQLLLLPLFAQAANMHLSFIRDVI  : 192
cry3Aa1    : EDYVSALSSUQKNPV-----SSRNPHSQGRIRELFSQAESHFRNSMPSFAIS----GYEVLFLTTYAQANTHLFLLKDAQ  : 220
cry3Bb     : EDYVNALNSUKKTPL-----SLRSKRSQDRIRELFSQAESHFRNSMPSFAVS----KFEVLFLPTYAQAANTHLLLLKDAQ : 213
cry4Aa     : STYHMHLKTUENNPN-----PQNTQDVRTQIQLVHYHFQNVIPELVNSCPPNPSDCDYYNILVLSSYAQAANLHLTVLNQAV : 225
cry4Ba     : DQYTTKFNTUKREPN-----NQ---------SYRTAVITQFMLTSAKLRETAVYFSNLVGYELLLLPIYAQVANFMLLIRDGL : 193
cry6Aa     : DPSIKKDGYFKKLQD-----ELDNIVDNNSDDDAIAKAIKDFKARCG--------ILIKEAKQYEEAAKNIVTSLDQF   : 186
cry7Aa     : DKYQKALADULGK-------QDDPEAILSVATEFRIIDSLFEFSMPSFKVT-----GYEIPLLTVYAQAANLHLALIRDST : 203
cry8Aa     : DVYQQSLEDULEN-------RNDARTRSVVSMQFIALDLNFVSSIPSFAVS-----GHEVLLAVYAQAVNLHLLLRDAS  : 214
cry10Aa    : DKYQEFFDKUEPAR------THANAKAVHDLFTTLEPIIDKDLDMLKNN-------ASYRIPTLPAYAQIATWHLNLLKHAA : 218
cry16Aa    : DDYNMULKKURDDP------KSTGNLSTLVTKFTALDSDFNGAIRTVNNQGS----PGYELLLLPVVAQIANLHLLLRDAQ : 218
cry19Ba    : NIYNRALAAUKQNK------MNFASGELIRSYINDLHILFTRDIQSDFSLG-----GYETVLLPSYASANLHLLLRDVA   : 208
cry24Aa    : RDYLGALEAUNNNK------SNIMYQTNVAEAFKTVEREFFTKLKGIYRTS----SSQITLLPTFTQAANLHLSMLRDAV  : 206
cry25Aa    : TVYLKNLQDUYDTRIPANPQGDSQLREAARRSLEEIERDFRKALAGEFAEAG----SQIVLLPIYAQAANIHLLLIKDAM  : 210
cry39Aa1   : GLFRDAFDSWEKNQ------NDPIAKNRVGGYFEDVHTHFVKDMASIFSAT-----NYEVLLLPVYAQAANLHLLLREGV  : 212
cry40Aa1   : EYYLPYLEAULKDGKPL-QKTMNSDIGQLVKYFELSERDFNEILGGSLARN-----MAQILLLPYFCASCKCQLLLRDAV  : 205
```

FIG. 1C

```
              *         260         *         280         *         300         *         320
axmi008  : QYKAQWFPFLSAENVRSELISPNSGCDFTGDYYERLKCKTAEYTNYCLYWYQVGLNQIKQGGTGADT-----WSKFNKFRR : 284
cry1Aa   : VFGQRWGFDAA----------------------------TINSRYNDLTRLIGNYTDYAVRWYNTGLERVWGPDSRD-----WVRYNQFRR : 234
cry1Ac   : VFGQRWGFDAA----------------------------TINSRYNDLTRLIGNYTDYAVRWYNTGLERVWGPDSRD-----WVRYNQFRR : 234
cry1Ia   : IFGKEWGLSSS----------------------------EISTFYNRQVERAGDYSDHCVKWYSTGLNNLRGTNAES-----WVRYNQFRR : 262
cry2Aa   : LMADEWGISAAT---------------------------LRTYRDYLRNYTRDYSNYCINTYQTAFRGLNTRLHDMLEFR-TYMFLNVFEY : 255
cry3Aa1  : IYGEEWGYEKE----------------------------DIAEFYKRQLKLTQEYTDHCVKWYNVGLDKLRGSSYES-----WVNFNRYRR : 278
cry3Bb   : VFGEEWGYSSE----------------------------DVAEFYHRQLKLTQQYTDHCVNWYNWYNGLNGLRGSTYDA----WVKFNRFRR : 271
cry4Aa   : KFEAYLKNNRQFDYL------------------------EPLPTAIDYYPVLTKAIEDYTNYCVTTYKKGLNLIKTTPDSNLDGNINWNTYNTYRT : 297
cry4Ba   : INAQEWSLAR-------S-----------------AGDQLYNTMVQYTKEYIAHSITWYNKGLDVLRNKSNG-------Q--WITFNDYKR : 251
cry6Aa   : LHGDQKKLEGVIN--------------------------IQKRLKEVQTALNQAHGESSPAHKELLEKVKNLKT--------------TLER- : 238
cry7Aa   : LYGDKWGFTQN----------------------------NIEENYNRQKKRISEYSDHCTKWYNSGLSRLNGSTYEQ-----WLNYNRFRR : 261
cry8Aa   : IFGEEWGFTPG----------------------------EISRFYNRQVQLTAEYSDYCVKWYKIGLDKLKGTTSKS-----WLNYHQFRR : 272
cry10Aa  : TYYNIWLQNQGINPSTFN---------------------SSNYYQGYLRRKIQEYTDYCIQTWNAGLTMIRTNTNAT----WNMYNTYRL : 283
cry16Aa  : IYGDKWWSARANA--------------------------RDNYYQIQLEKIKEYTEYCINWYNKGLNDFRTAGQ-------WVNFNRYRR : 275
cry19Ba  : IYG-KELGYPSTD--------------------------VEFYYNEQKYYTEKYSNYCVNTYKSGLESKKQIG--------WSDFNRYRR : 263
cry24Aa  : MYQEGWNLQSHIN----------------------YSKELDDALEDYTNYCVEVYTKGLNALRGSTAID-----WLEFNSFRR : 262
cry25Aa  : QFRTDLGLIRPVG---------------------VPITTSAEDPFESEFLLRIKKYTDHCISYYDDGLAKIRSRGSDG-----ETWWEFNKFRR : 278
cry39Aa1 : IYGSRWGIAPA----------------------------ADFYHDQLLKYTAIYANHCVTWYNNGLAQQKELFAKSPN----WNRFNAYRR : 271
cry40Aa1 : QYEEQWFPFLSAENVRSELISPNSGCDFTGDYYERLKCKIAEYTDYCEYWYQAGLNQIKQAGTGADT-----WAKFNKFRR : 281
```

FIG. 1D

```
axmi008  : EMTLAVLDIIAIFPTYDFEKYPLP------THVELTREIYTDAVGYSSGTYSWLRNWPNTFNGLEAN------GTRGPGL : 352
cry1Ae   : ELTLTVLDIVALFSNYDSRRYPIR------TVSQLTREIYTNPVLENFDGSFRGMAQRIEQN------------IRQPHL : 296
cry1Ac   : ELTLTVLDIVALFPNYDSRRYPIR------TVSQLTREIYTNPVLENFDGSFRGSAQGIERS------------IRSPHL : 296
cry1Ie   : DMTLMVLDIVALFPSYDTQMYPIK------TTAQLTREVYTDAIGTVHPHPSFTSTTWYMNNAPSFSALEAAVVRNPHL : 335
cry1Ie   : VSIWSLFKYQSLMVSSGANLYASG------

FIG. 1F

```
              *         500         *         520         *         540         *         560
exmi008   : N---LWGETTARPEYRVSKADFRRWGGPDLNYDAGNMGLSRMTIESTFPLVHSN------------GVRGPSHRLSNAACVVY : 488
cry1Aa    : YRRIILG-SGPMNQELFVLDGTEFSFASLTTNLPSTIYRQRGTVDSLDVIPPQDNS------------VPPRAGFSHRLSHVTMLSQ : 439
cry1Ac    : VRRPFN--IGINQQLSVLDGTEFAYG-TSSMLPSAVTRKSGTVDSLDEIPPQNNN------------VPPRQGFSHRLSHVSMFRS : 438
cry1Ia    : LTQPVNGVPRVDFHUKFVTHPIASDMFYPGVAGIG-----TQLQDSENELPEATG------------QPNYESYSHRLSHIGLISA : 481
cry2Aa    : LRCGAFSARGNSNYFPDYFIRNISGVPLVIRNEDLTRPLHYNQIRNIESPSGTPGG-----------ARAYLVSVHNRKNNIY : 475
cry3Aa1   : AVUPS-AVYSGVTKAVEFSQVMDQTDEASTQTYDSKRN-VGAVSUDSIDQLPPETID-----------EPLEKGYSHQLNYVMCFLM : 489
cry3Bb    : AAUPNGKVYLGVTKWDFSQVDDQKNETSTQTYDSKRNNGHVSAQDSIDQLPPETID-----------EPLEKAYSHQLNYAECFLM : 484
cry4Aa    : DNKYLNDYNNISKMDFFITNGTIRLLEKELTAGSGQITYDVMKNIFGLPILKRRENQGNPTLFPTYDNYSHILSFIKSLSI : 509
cry4Ba    : P---S----MRVTKMDFYKIDGTLASYNSNIIPTP----EGLRTTFFGFSTNENTPNQ---------PTVNDYTHILSYIKTDVI : 453
cry6Aa    : FTLNAYSTMSRQMLPINVISDSCNCSTTNMTSMQYSNPTTNMTSMQYMISHEYTSLP---------MNFMLSRNSNIEYKC : 451
cry7Aa    : VVYPY---TQMYGVEQVEFYGVKGHVHYRGDNKYDLT-----YDSIDQLPPDGE---------PIHERVTHRLCHATAIFK : 466
cry8Aa    : YYQKAYGVPGSUFHMVKRGTSSTTAYLYSKTHTALQG--CTQVYESSDEIPLDRT---------VPVAESYSHRLSHITSHSF : 494
cry10Aa   : DKVEIVRHREYSDIIVEMIFSMSSEVFRYSSNSTIENNYKRTDSYMIPKQTURME--------EYGHTLSYIKTDNY : 479
cry16Aa   : EYIYPUGDPVNITKMNFSVIDNNSSKELIYGAHRTNKPVWRTDFDFLTNKEGIEL--------AKYNDYNHILSYMLINGE : 483
cry19Ba   : EWIYPUTDPVNITKLNFSITDNSNSSESIYGAERMNKPTVRTDFNFLLNRAGNGP--------TTYNDYNHILSYMLINGE : 477
cry24Aa   : VSTIQGAMDTTFGVSSSRFFDIRGRMQLYQSNKFYPSLPITITFPGEESSEGNAN--------DVSHLLCDVKILQE : 482
cry25Aa   : QALPGLNMSIHVIVGIDSFRAIGPGGQGDHTFSLPGGDMYDCGKVQINPLEDYRWS--------DHHISDMTINQSVQL : 491
cry39Aa1  : TNISPYTDPVGISQMQFSLTMMQQLTYTGTSAPKYP-----VRAETFFEIPPTDEKP---------LTYEMYSHILSYMTSAQH : 473
cry40Aa1  : N---LWGEINARPEYRVSRAEFSESTAFIYLDAGNSGLSSMTTISKLPGIKNPEP-----------SYRDYSHRLSNAACVGA : 486
```

FIG. 1G

|           |   |     |   | 580 |   | 600 |   | 620 |   | 640 |   |     |
|-----------|---|-----|---|-----|---|-----|---|-----|---|-----|---|-----|
| axmi008   | : | GNS------RVNVYGWTHTSLKRENIIEANQITQIPAVKSYYLQNYLANAYTYV-IKGTHTGGDLIRFLRTKSEYNAVY | : | 560 |
| cry1Ae    | : | AAG------AVYTLRAPTFSWQHRSAEFNNIIPSSQITQIPLIKSTNLGSGTSV------VKGPGFTGGDLIRRTSPG--------- | : | 505 |
| cry1Ac    | : | GFSNSSVSIIRAPMFSWIHRSAEFNNIIASDSITQIPAVKGNFLFNGSVI------S-GPGFTGGDLVRLNSSGN----NIQ | : | 509 |
| cry1Ia    | : | S-------HVKALVYSWTHRSADRINTIEPNSITQIPLVKAFNLSSGAAV------VRGPGFTGGDILRRIN-------T | : | 541 |
| cry2Aa    | : | AAN------ENGTMIHLAPEDYTGFTISPIHATQVNNQTRTFISEKFGN---------------GDSLRFEQSN------- | : | 529 |
| cry3Aa1   | : | QGS------RGTIPVLTWTHRSVDFFNMIDSKKITQLPLVKAYKLQSGASV------VAGPRFTGGDIIQCTE-------N | : | 551 |
| cry3Bb    | : | QDR------RGTIPFFTWTHRSVDFFNTIDAEKITQLPVVKAYALSSGASI------IEGPGFTGGNLLFLKESS------N | : | 548 |
| cry4Aa    | : | PATY-----KTQVYTFAWTHSSVDPKNTIYTHLTTQIPAVKANSLGTASKV------VQGPGHTGGDLIDFKDHFK----IT- | : | 576 |
| cry4Ba    | : | DYN------SNRVSFAWTHKIVDPMNQIYTDAITQVPAVKSNFLNATAKV------IKGPGHTGGDLVALTSNGT----LSG | : | 519 |
| cry6Aa    | : | P-------ENNFMIYUYNNSDUYNNSDUYNN------------------------------------------ | : | 475 |
| cry7Aa    | : | STP--DYDNATIPIFSWTHRSAEYYNRIYPNKITKIPAVKMYKLDDPSTV------VKGPGFTGGDLVKRGS-------T | : | 531 |
| cry8Aa    | : | SKNG-SAYYGSFPVFVWTHTSADLNNTIYSDKITQIPAVKRGDMLYLGGSV------VQGPGFTGGDILKRTN-------P | : | 560 |
| cry10Aa   | : | IFSVVR--ERRRVAFSWTHTSVDFQNTIDLDMITQIHALKALKVSSDSKIVK------GPGHTGGDLVILKDSMD------ | : | 546 |
| cry16Aa   | : | TFGQ-----KRHGYSFAFTHSSVDPNNTIAANKITQIPVVKSSINGSISI------EKGPGFTGGDLVKMRADS------ | : | 547 |
| cry19Ba   | : | TFGQ-----KRHGYSFAFTHSSVDRYNTIVPDKIVQIPAVKTNLVGANIIK------GPGHTGGDLLKLEYER------ | : | 539 |
| cry24Aa   | : | DSSNICEGRSSLLSHAWTHASLDRNNTILPDEITQIPAVTAYELRGNSS------VVAGPGSTGGDLVKMSYHS------ | : | 550 |
| cry25Aa   | : | ASNPTQTFAFSALSLGWHHSSAGNRNVYVYDKITQIPATKTVREHPMIK---------GPGFTGGDLADLSSNS----DIL | : | 559 |
| cry39Aa1  | : | FGD------KKIGYTFAWMHESVDFDNRVDPDKITQIPAVKGDYIQYGYVK------QGPGHTGGDLVSMIRTDR------ | : | 536 |
| cry40Aa1  | : | GNS------RINVYGWTHTSMSKYNLIYPDKITQIPAVKAFDISDTGP--GQVI-AGPGHTGGNVVSLP--------YY | : | 548 |

```
                         *         740         *         760         *         780
axmi008    : LPSSN-----IQMDVEMQANSFQSDVNVLIDKIEFLPSNTTTLEYEGERDLEKTKNAVNDLFTN : 693
cry1Ab     : NFSNG-----SSVFTLSAHVFNSGNEVYIDRIEFVPAEVTFEAE---YDLERAQKAVNELFTS : 629
cry1Ac     : TSSLG-----N----IVGVRNFSGTAGVIIDRFEFIPVTATLEAE---YNLERAQKAVNALFTS : 631
cry1Ib     : SFLDV-----QSTFTIGAUNFSSGNEVYIDRIEFVPVEVTYEAE---YDFEKAQEKVTALFTS : 666
cry2Aa     : NTNVT-----LDINVTLNSGTPFDLMNIMFVPTNLPPLY------------------------ : 633
cry3Aa1    : ELSG------NNLQIGVTGLSAGDKVYIDKIEFIPVN------------------------ : 652
cry3Bb     : GFSGD-----KNELIIGAESFVSNEKIYIDKIEFIPVQL----------------------- : 652
cry4Aa     : KFAPN-----QNISLVFNRSDVYTNTTVLIDKIEFLPITRSIREDREKQKLETVQQIINTFYAN : 703
cry4Ba     : VPMRLSSNQLITTAIQPLNMTSNNQVILDRIEIPITQSVLDETENQNLESEREVVNALFTN : 659
cry6Aa     : ------------------------------------------------------------  : —
cry7Aa     : QFPDE-----HPKITLHLSDLSMNNSSFYVDSIEFIPVDWNYAEK---EKLEKAQKAVNTLFTE : 659
cry8Aa     : QFRET-----QDKILLSMGDFSSGQEVYIDRIEFIPVDETYEAE---QDLEAAKKAVNALFTN : 684
cry10Aa    : PNKTFEG---EDTLLMTLYGTPNHSYNIYIDKIEFIPITQSVLDYTEKQNIEKTQKIVNDLFVN : 675
cry16Aa    : DLTME-----VTYPYGRQFVEDIPSLIILDKIEFLPTN------------------------ : 648
cry19Ba    : SGGPS-----ISSNTLWLDNFSMGPVILDKIEFIPLGITLNQAQGYDTYDQNANGMYHQMYS : 663
cry

```
axmi008-orf2  : VSPMFTSSTKNTLKIETTDYEIDQAAISIECMSDEQNPQEKIMLDEIKLAKQLSQSRNLLQN---GDFSGNDWTFGNDIIIGSNNPIFKGKFLQMRGAR :  97
cry19Aa-orf2  : VNFMLTSGAKNMLKLETTDYEIDQAAISIECMSDEQNPQEKIMLDEIKLAKQLSQSRNLLQN---GDFSGNDWTFGNDIIIGSNNPIFKGKFLQMRGAR :  99
crybun2orf2   : ---MFISNIKNTLKIETTDYEIDQMANAIENMSGEQYSQEKMMQHDIKYAKQLSQARNLLQNG-DFEDLFSGWTTSMQMSIQADMATFKGNYLHMSGAR :  96
crybun3orf2   : ---MFTNGTKNTLKIETTDYEIDQAAISIECMSNEHSSKEEMMLGDEVKQAKQLSWSRNLLYNG-DFEDVSNGWKTSNTTEIPENSPVFKGHYLHMFGAR :  97
cry4Aa        : INTFYANPIKNTLQSELTDYDIDQAANLVECISEELYPKEKMLLDEVKNAKQLSQSRNVLQNG-DFESATLGWTTSDNITIQEDDPIFKGHYLHMSGAR :  99
cry4Ba        : VNALFTNDAKDALNIGTDYDIDQAANLVECISEELYPKEKMLLDEVKNAKQLSQSRNVLQNG-DFESATLGWTTSDNITIQEDDPIFKGHYLHMSGAR :  99 axmi008-orf2  : DIYGTLFPTYICQKIDESKLKPYTRYRVRGFVGSSKDLKLMVTRYGKEIDAIMNVPNDLAYMQPNPSCGDYRCESS---SQYVSQGYPTP--TDGYAPDM : 192
cry19Aa-orf2  : DIYGTIFPTYIVQKIDESKLKPYTRYLVRGFVGSSKDLELMVMRYGKEIDTWMNVPNDIPYVPSMPVCNELYDGQQPYTNRHVGYNPMPVSQPSYTSDT : 199
crybun2orf2   : DIDGTLFPTYIFPTYIEESKLKPYTRYLVRGFVGSSKDLKLMVTRYGKEIDAIMNVPNDLAYMQPNPSCGDSRCESS---SRYVSQGYPTPV-TDGYASGR : 192
crybun3orf2   : DIYGTIFPTYIYQKIDESKLKPYTRYLVRGFVGSSKDLRLMVTRYGKEIDAMMNVPMDLAYMQPNPSCGDSRCESS---SQYVSQGYPTP--TDGYAPDR : 192
cry4Aa        : DIDGTIFPTYIFQKIDESKLKPYTRYLVRGFVGSSKDVELVVSRYGEEIDAIMNVPADLNYLYP----STFDCEGS-----MRCETSAVPANIGNTSDML : 190
cry4Ba        : DIDGTIFPTYIFQKIDESKLKPYTRYLVRGFVGSSKDVELVVSRYGEEIDAIMNVPADLNYLYP----STFDCEGS-----MRCETSAVPANIGNTSDML : 190 axmi008-orf2  : YACPQNIDRKHVKCHDRKHPFDFHIDTGEVDTNTNVGIDVLKISNPDGYATVGNLEVIEEGPLTGEALAHVKQEKKKQHMEKKRWETQQAYDPAKQAV : 292
cry19Aa-orf2  : CQCTP--GKKHVKCHDSHQFKFHIDTGEVDYNTNLGIWVLFKISSPDGYATLGNLEVIEEGPVRGEAVTHVKQEKKKUNQQMEKKRMETKRVYDRAKQAV : 297
crybun2orf2   : ACQSNRGTKHVKCHDRHPFDFHIDTGEVDTNTNVGLDTNTNVGIDVLFKISNPDGYATLGNLEVIEEGPLTGEALTHVKQKEKKQKHMEKKRWETQQAYDPAKQAV : 292
crybun3orf2   : YACPSSSDRKHVMCHDRHPFDFHIDTGEVDTNTNVGIDVLFKISNPDGYATLGNLEVIEEGPLTGEALTHVKQKEKKUKQHMEKKRWETQQAYDPAKQAV : 292
cry4Aa        : YSCQYDTGKKHVVCQDSHQFSFTIDTGALDTMENIGVWVMFKISSPDGYASLDNLEVIEEGPIDGEALSRVKHMEKKWNDQMEAKRSETQQAYDVAKQAI : 290
cry4Ba        : YSCQYDTGKKHVVCQDSHQFSFTIDTGALDTMENIGVWVMFKISSPDGYASLDNLEVIEEGPIDGEALSRVKHMEKKWNDQMEAKRSETQQAYDVAKQAI : 290
```

AXMI-008, A DELTA-ENDOTOXIN GENE AND METHODS FOR ITS USE

CROSS REFERENCE TO RELATED APPLICATION

This application claims the benefit of U.S. Provisional Application Ser. No. 60/448,797, filed Feb. 20, 2003, the contents of which are herein incorporated by reference in their entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In Advanced Engineered Pesticides. Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in 'jelly-roll' formation (de Maagd et al. (2001) supra). Domains II and III are involved in receptor recognition and binding, and are therefore considered determinants of toxin specificity.

Because of the devastation that insects can confer, there is a continual need to discover new forms of *Bacillus thuringiensis* delta-endotoxins.

SUMMARY OF INVENTION

Compositions and methods for conferring pesticide resistance to bacteria, plants, plant cells, tissues, and seeds are provided. Compositions include isolated nucleic acid molecules encoding sequences for delta-endotoxin and delta-endotoxin-associated polypeptides, vectors comprising those nucleic acid molecules, and host cells comprising the vectors. Compositions also include isolated or recombinant polypeptide sequences of the endotoxin, compositions comprising these polypeptides, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for optimum expression in an organism, including, but not limited to, a microorganism or a plant. Compositions also comprise transformed bacteria, plants, plant cells, tissues, and seeds.

In particular, the present invention provides for isolated nucleic acid molecules comprising a nucleotide sequence encoding an amino acid sequence shown in SEQ ID NO:3, 5, or 7, or a nucleotide sequence set forth in SEQ ID NO:1, 2, 4, or 6, as well as variants and fragments thereof. Nucleotide sequences that are complementary to a nucleotide sequence of the invention, or that hybridize to a sequence of the invention, are also encompassed.

Methods are provided for producing the polypeptides of the invention, and for using those polypeptides for controlling or killing a lepidopteran or coleopteran pest.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin or delta-endotoxin-associated proteins that have pesticidal activity, or for detecting the presence of delta-endotoxin or delta-endotoxin-associated proteins or nucleic acids in products or organisms.

DESCRIPTION OF FIGURES

Figure 1F:
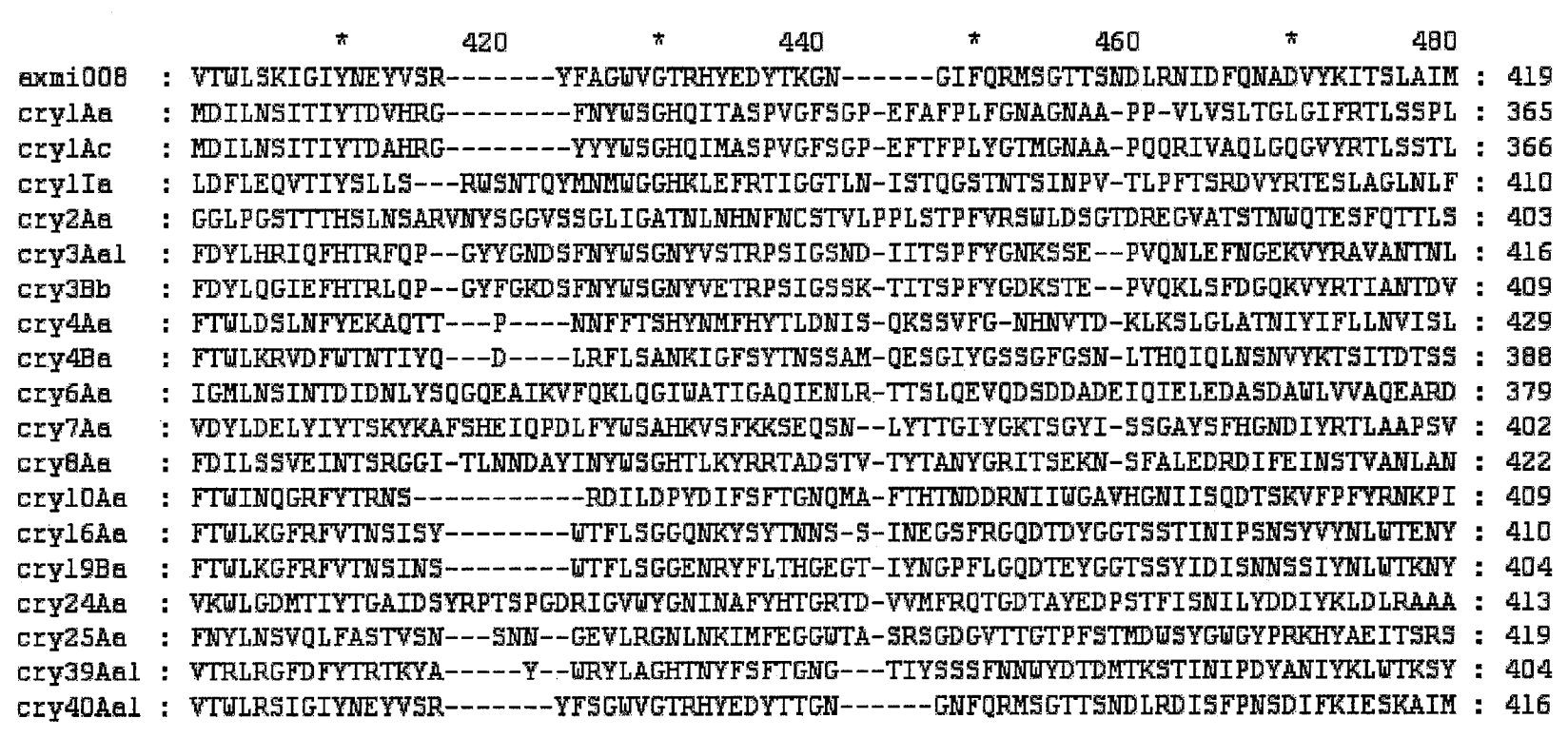

FIGS. 1A through 1J show an alignment of AXMI-008 (SEQ ID NO:3) with cry1Aa (SEQ ID NO:8), cry1Ac (SEQ ID NO:9), cry1Ia (SEQ ID NO:10), cry2Aa (SEQ ID NO:11), cry3Aa1 (SEQ ID NO:12), cry3Bb (SEQ ID NO:13), cry4Aa (SEQ ID NO:14), cry4Ba (SEQ ID NO:15), cry6Aa (SEQ ID NO:16), cry7Aa (SEQ ID NO:17), cry8Aa (SEQ ID NO:18), cry10Aa (SEQ ID NO:19), cry16Aa (SEQ ID NO:20), cry19Ba (SEQ ID NO:21), cry24Aa (SEQ ID NO:22), cry25Aa (SEQ ID NO:23), cry39Aa1 (SEQ ID NO:24), and cry40Aa1 (SEQ ID NO:25). Toxins having C-terminal non-toxic domains were artificially truncated as shown. Conserved group 1 is found from about amino acid residue 185 to about 206 of SEQ ID NO:3. Conserved group 2 is found from about amino acid residue 276 to about 318 of SEQ ID NO:3. Conserved group 3 is found from about amino acid residue 497 to about 547 of SEQ ID NO:3. Conserved group 4 is found from about amino acid residue 576 to about 586 of SEQ ID NO:3. Conserved group 5 is found from about amino acid residue 657 to about 667 of SEQ ID NO:3

FIGS. 2A and B show an alignment of AXMI-008orf2 (SEQ ID NO:7) with cry19Aa-orf2 (SEQ ID NO:26), crybun2-orf2 (SEQ ID NO:27), crybun3-orf2 (SEQ ID NO:28), cry4Aa (SEQ ID NO:14), and cry4Ba (SEQ ID NO:15). The alignment shows the most highly conserved amino acid residues highlighted in black, and highly conserved amino acid residues highlighted in gray.

DETAILED DESCRIPTION

The present invention is drawn to compositions and methods for regulating pest resistance in organisms, particularly plants or plant cells. The methods involve transforming organisms with a nucleotide sequence encoding a delta-endotoxin or delta-endotoxin-associated protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin or delta-endotoxin-associated nucleic acids and proteins of *Bacillus thuringiensis*. The sequences find use in the construction of expression vectors for subsequent transformation into organisms of interest, as probes for the isolation of other delta-endotoxin or delta-endotoxin-associated genes, and for the generation of altered pesticidal proteins by methods known in the art, such as domain swapping or DNA shuffling. The proteins find use in controlling or killing lepidopteran or coleopteran pest populations and for producing compositions with pesticidal activity.

DEFINITIONS

By "delta-endotoxin" is intended a toxin from *Bacillus thuringiensis* that has toxic activity against one or more pests, including, but not limited to, members of the Lepidoptera, Diptera, and Coleoptera orders. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Bacterial genes, such as the AXMI-008 gene of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. For example, an alternate start site for a delta-endotoxin protein of the invention may be at nucleotide 177 of SEQ ID NO:1. Translation from this alternate start site results in the amino acid sequence found in SEQ ID NO:5. These delta-endotoxin proteins are encompassed in the present invention and may be used in the methods of the present invention.

In addition, there may be one or more additional open reading frames in the disclosed nucleotide sequences that encode one or more delta-endotoxin-associated proteins. By "delta-endotoxin-associated protein" is intended a protein encoded by a nucleotide sequence disclosed herein using an alternate open reading frame than that used by the delta-endotoxins of the present invention. Proteins such as these are known in the art as helper proteins, stabilizing sequences, or delta-endotoxin-associated proteins. These delta-endotoxin-associated proteins may have pesticidal activity, or may be important in facilitating expression of delta-endotoxin proteins. Methods are known in the art for measuring pesticidal activity and for determining the effects of delta-endotoxin-associated proteins on delta-endotoxin protein expression and crystal formation (see, for example, Park et al. (1999) *FEMS Microbiol. Lett.* 181:319-327; Ge et al. (1998) *FEMS Microbiol. Lett.* 165:35-41; Rosso and Delecluse (1997) *Appl. Environ. Microbiol.* 63:4449-4455). These delta-endotoxin-associated proteins are encompassed by the present invention, and may be used in the methods disclosed herein, either alone or in combination with known delta-endotoxin proteins. In one embodiment, the delta-endotoxin-associated protein has the amino acid sequence found in SEQ ID NO:7 and is encoded by the nucleotide sequence of SEQ ID NO:6.

By "plant cell" is intended all known forms of plant, including undifferentiated tissue (e.g. callus), suspension culture cells, protoplasts, leaf cells, root cells, phloem cells, plant seeds, pollen, propagules, embryos and the like. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has ability to incorporate, integrate and express heterologous DNA sequences or fragments in a foreign cell.

"Transgenic plants" or "transformed plants" or "stably transformed plants or cells or tissues" refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Provided herein are novel isolated nucleotide sequences that confer pesticidal activity. Also provided are the amino acid sequences for the delta-endotoxin and delta-endotoxin-associated proteins. The protein resulting from translation of this gene allows cells to control or kill pests that ingest it.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin or delta-endotoxin-associated-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. A delta-endotoxin or delta-endotoxin-associated protein that is substantially free of cellular material includes preparations of protein having less than about 30%, 20%, 10%, or 5% (by dry weight) of non-delta-endotoxin or non-delta-endotoxin-associated protein (also referred to herein as a "contaminating protein"). Various aspects of the invention are described in further detail in the following subsections.

Isolated Nucleic Acid Molecules, and Variants and Fragments Thereof

One aspect of the invention pertains to isolated nucleic acid molecules comprising nucleotide sequences encoding delta-endotoxin or delta-endotoxin-associated proteins and polypeptides or biologically active portions thereof, as well as nucleic acid molecules sufficient for use as hybridization probes to identify delta-endotoxin or delta-endotoxin-associated-encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOS:1, 2, 4, and 6, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the delta-endotoxin or delta-endotoxin-associated proteins encoded by these nucleotide sequences are set forth in SEQ ID NOS:3, 5, and 7.

Nucleic acid molecules that are fragments of these delta-endotoxin or delta-endotoxin-associated protein-encoding nucleotide sequences are also encompassed by the present invention. By "fragment" is intended a portion of the nucleotide sequence encoding a delta-endotoxin protein or delta-endotoxin-associated protein. A fragment of a nucleotide sequence may encode a biologically active portion of a delta-endotoxin or delta-endotoxin-associated protein, or it may be a fragment that can be used as a hybridization probe or PCR primer using methods disclosed below. Nucleic acid molecules that are fragments of a delta-endotoxin or a delta-endotoxin-associated nucleotide sequence comprise at least about 15, 20, 50, 75, 100, 200, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 3000, 3500, 4000, 4500, 5000, 5500 nucleotides, or up to the number of nucleotides present in a full-length delta-endotoxin or delta-endotoxin-associated protein-encoding nucleotide sequence disclosed herein (for example, 5980 nucleotides for SEQ ID NO:1, 2082 for SEQ ID NO:2, 2073 for SEQ ID NO:4, or 1686 for SEQ ID NO:6), depending upon the intended use.

Fragments of the nucleotide sequences of the present invention will encode protein fragments that retain the biological activity of the delta-endotoxin or delta-endotoxin-associated protein and, hence, retain pesticidal activity or delta-endotoxin-associated protein activity, respectively. By "delta-endotoxin activity" is intended pesticidal activity. By "delta-endotoxin-associated protein activity" is intended that the protein have pesticidal activity, or that the protein improves expression of a delta-endotoxin protein. This improvement in protein expression can happen by any mechanism. By "retains activity" is intended that the fragment will have at least about 30%, preferably at least about 50%, more preferably at least about 70%, even more preferably at least about 80% of the activity of the delta-endotoxin or delta-endotoxin-associated protein. Methods are known in the art for determining the effects of delta-endotoxin-associated proteins on delta-endotoxin protein expression and crystal formation (see, for example, Park et al. (1999) *FEMS Microbiol. Lett.* 181:319-327; Ge et al. (1998) *FEMS Microbiol. Lett.* 165:35-41; Rosso and Delecluse (1997) *Appl. Environ. Microbiol.* 63:4449-4455).

Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin or delta-endotoxin-associated protein-encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, or 650 contiguous amino acids, or up to the total number of amino acids present in a full-length delta-endotoxin or delta-endotoxin-associated protein of the invention (for example, 693 amino acids for SEQ ID NO:3, 690 amino acids for SEQ ID NO:5, or 561 amino acids for SEQ ID NO:7).

Preferred delta-endotoxin or delta-endotoxin-associated proteins of the present invention are encoded by a nucleotide sequences sufficiently identical to the nucleotide sequences of SEQ ID NO:1, 2, 4, or 6. By "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin or delta-endotoxin-associated nucleic acid molecules of the invention. BLAST protein searches can be performed with the BLASTX program, score=50, wordlength=3, to obtain amino acid sequences homologous to delta-endotoxin or delta-endotoxin-associated protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See, Altschul et al. (1997) supra. When utilizing BLAST, Gapped BLAST, and PSI-Blast programs, the default parameters of the respective programs (e.g., BLASTX and BLASTN) can be used. See, www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

The invention also encompasses variant nucleic acid molecules. "Variants" of the delta-endotoxin or delta-endotoxin-associated protein-encoding nucleotide sequences include those sequences that encode the delta-endotoxin or delta-endotoxin-associated proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin or delta-endotoxin-associated proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, preferably at least about 50%, more preferably about at least 70%, even more preferably at least about 80% of the activity of the native protein. Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The invention also encompasses variant nucleic acid molecules. "Variants" of the delta-endotoxin or delta-endotoxin-associated-encoding nucleotide sequences include those sequences that encode the delta-endotoxin or delta-endotoxin-associated proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin or delta-endotoxin-associated proteins disclosed in the present invention as discussed below.

The skilled artisan will further appreciate that changes can be introduced by mutation into the nucleotide sequences of the invention thereby leading to changes in the amino acid sequence of the encoded delta-endotoxin or delta-endotoxin-associated proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a delta-endotoxin or delta-endotoxin-associated protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

There are generally five highly conserved regions among the delta-endotoxin proteins, concentrated largely in the center of the domain or at the junction between domains (Rajamohan et al. (1998) *Prog. Nucleic Acid Res. Mol. Biol.* 60:1-23). The blocks of conserved amino acids for various delta-endotoxins as well as consensus sequences may be found in Schnepf et al. (1998) *Microbio. Mol. Biol. Rev.* 62:775-806 and Lereclus et al. (1989) Role, Structure, and Molecular Organization of the Genes Coding for the Parasporal d-endotoxins of *Bacillus thuringiensis*. In Regulation of Procaryotic Development. Issar Smit, Slepecky, R. A., Setlow, P. American Society for Microbiology, Washington, D.C. 20006. It has been proposed that delta-endotoxins having these conserved regions may share a similar structure, consisting of three domains (Li et al. (1991) *Nature* 353: 815-821). Domain I has the highest similarity between delta-endotoxins (Bravo (1997) *J. Bacteriol.* 179: 2793-2801).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in the alignment of FIGS. 1A through 1J or 2A and B. Examples of residues that are conserved but that may allow conservative amino acid substitutions and still retain activity include, for example, residues that have only conservative substitutions between all proteins contained in the alignment of FIGS. 1A through 1J or 2A and B. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin or delta-endotoxin-associated activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin or delta-endotoxin-associated sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin or delta-endotoxin-associated nucleotide sequence can be used to screen cDNA or genomic libraries. Methods for construction of such cDNA and genomic libraries are generally known in the art and are disclosed in Sambrook and Russell, 2001. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known delta-endotoxin or delta-endotoxin-associated-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably at least about 50, 75, 100, 125, 150, 175, 200, 250, 300, 350, or 400 consecutive nucleotides of delta-endotoxin or delta-endotoxin-associated-encoding nucleotide sequence of the invention or a fragment or variant thereof. Preparation of probes for hybridization is generally known in the art and is disclosed in Sambrook and Russell, 2001, herein incorporated by reference.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the delta-endotoxin or delta-endotoxin-associated sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire delta-endotoxin or delta-endotoxin-associated sequence disclosed herein, or one or more portions thereof, may be used as a probe capable of specifically hybridizing to corresponding delta-endotoxin or delta-endotoxin-associated-like sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding delta-endotoxin or delta-endotoxin-associated sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 110° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated Proteins and Variants and Fragments Thereof

Delta-endotoxin and delta-endotoxin-associated proteins are also encompassed within the present invention. By "delta-endotoxin protein" is intended a protein having the amino acid sequence set forth in SEQ ID NO:3 or 5. By "delta-endotoxin-associated protein" is intended a protein having the amino acid sequence set forth in SEQ ID NO:7. Fragments, biologically active portions, and variants thereof are also provided, and may be used to practice the methods of the present invention.

"Fragments" or "biologically active portions" include polypeptide fragments comprising a portion of an amino acid sequence encoding a delta-endotoxin or delta-endotoxin-associated protein as set forth in SEQ ID NO:3, 5, or 7, and that retain delta-endotoxin activity or delta-endotoxin-associated activity. A biologically active portion of a delta-endotoxin or delta-endotoxin-associated protein can be a polypeptide that is, for example, 10, 25, 50, 100 or more amino acids in length. Such biologically active portions can be prepared by recombinant techniques and evaluated for delta-endotoxin or delta-endotoxin-associated activity. Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids SEQ ID NO:3, 5, or 7. The invention encompasses other fragments, however, such as any fragment in the protein greater than about 10, 20, 30, 50, 100, 150, 200, 250, 300, 350, 400, 450, 500, 550, 600, and 650 amino acids.

By "variants" is intended proteins or polypeptides having an amino acid sequence that is at least about 60%, 65%, preferably about 70%, 75%, more preferably about 80%, 85%, most preferably about 90%, 91%, 92%, 93%, 94%, 95%, 96%, 97%, 98% or 99% identical to the amino acid sequence of SEQ ID NO:3, 5, or 7. Variants also include polypeptides encoded by a nucleic acid molecule that hybridizes to the nucleic acid molecule of SEQ ID NO:1, 2, 4, or 6, or a complement thereof, under stringent conditions. Such variants generally retain delta-endotoxin or delta-endotoxin-associated activity. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Altered or Improved Variants

It is recognized that DNA sequences of a delta-endotoxin or delta-endotoxin-associated protein may be altered by various methods, and that these alterations may result in DNA sequences encoding proteins with amino acid sequences different than that encoded by the delta-endotoxin or delta-endotoxin-associated protein of the present invention. This protein may be altered in various ways including amino acid substitutions, deletions, truncations, and insertions. Methods for such manipulations are generally known in the art. For example, amino acid sequence variants of the delta-endotoxin or delta-endotoxin-associated protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin or delta-endotoxin-associated protein to confer pesticidal activity may be improved by the use of such techniques upon the compositions of this invention. For example, one may express the delta-endotoxin or delta-endotoxin-associated protein in host cells that exhibit high rates of base misincorporation during DNA replication, such as XL-1 Red (Stratagene). After propagation in such strains, one can isolate the delta-endotoxin or delta-endotoxin-associated DNA (for example by preparing plasmid DNA, or by amplifying by PCR and cloning the resulting PCR fragment into a vector), culture the delta-endotoxin or delta-endotoxin-associated mutations in a non-mutagenic strain, and identify mutated delta-endotoxin or delta-endotoxin-associated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin or delta-endotoxin-associated protein coding regions can be used to create a new delta-endotoxin or delta-endotoxin-associated protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the delta-endotoxin or delta-endotoxin-associated gene of the invention and other known delta-endotoxin or delta-endotoxin-associated genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin or delta-endotoxin-associated proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266: 17954-17958; Schnepf et al. (1990) *J. Biol. Chem.* 265: 20923-20930; Rang et al. 91999) *Appl. Environ. Micriobiol.* 65:2918-2925).

Plant Transformation

Transformation of plant cells can be accomplished by one of several techniques known in the art. First, one engineers the delta-endotoxin or delta-endotoxin-associated gene in a way that allows its expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this 'plant expression cassette' will be inserted into a 'plant transformation vector'. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a 'gene of interest' (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science*, 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethelene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6: 271-282; Ishida et al. (1996) *Nature Biotechnology* 14: 745-750). Explants are typically transferred to a fresh supply of the same medium and cultured routinely. A general description of the techniques and methods for generating transgenic plantlets are found in Ayres and Park, 1994 (*Critical Reviews in Plant Science* 13: 219-239) and Bommineni and Jauhar, 1997 (*Maydica* 42: 107-120). Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6: 271-282; Ishida et al. (1996) *Nature Biotechnology* 14: 745-750; Ayres and Park (1994) *Critical Reviews in Plant Science* 13: 219-239; Bommineni and Jauhar (1997) *Maydica* 42: 107-120) to transfer DNA.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055; U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); aerosol beam transformation (U.S. Published Application No. 20010026941; U.S. Pat. No. 4,945,050; International Publication No. WO 91/00915; U.S. Published Application No. 2002015066); and Lec1 transformation (WO 00/28058). Also see Weissinger et al. (1988) *Ann. Rev. Genet.* 22:421-477; Sanford et al. (1987) *Particulate Science and Technology* 5:27-37; Christou et al. (1988) *Plant Physiol.* 87:671-674; McCabe et al. (1988) *Bio/Technology* 6:923-926; Finer and McMullen (1991) *In Vitro Cell Dev. Biol.* 27P:175-182; Singh et al. (1998) *Theor. Appl. Genet.* 96:319-324 (soybean); Datta et al. (1990) *Biotechnology* 8:736-740; Klein et al. (1988) *Proc. Natl. Acad. Sci. USA* 85:4305-4309; U.S. Pat. No. 5,240,855; U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin); Klein et al. (1988) *Plant Physiol.* 91:440-444; Hooykaas-Van Slogteren et al. (1984) *Nature (London)* 311:763-764; U.S. Pat. No. 5,736,369; Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209; Kaeppler et al. (1990) *Plant Cell Reports* 9:415-418 and Kaeppler et al. (1992) *Theor. Appl. Genet.* 84:560-566; D'Halluin et al. (1992) *Plant Cell* 4:1495-1505; Li et al. (1993) *Plant Cell Reports* 12:250-255 and Christou and Ford (1995) *Annals of Botany* 75:407-413; Osjoda et al. (1996) *Nature Biotechnology* 14:745-750; all of which are herein incorporated by reference.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The delta-endotoxin or delta-endotoxin-associated sequences of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the delta-endotoxin or delta-endotoxin-associated sequence to be under the transcriptional regulation of the regulatory regions.

The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably-linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing plant-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis: PCR analysis is a rapid method to screen transformed cells, tissue or shoots for the presence of incorporated gene at the earlier stage before transplanting into the soil (Sambrook and Russell, 2001). PCR is carried out using oligonucleotide primers specific to the gene of interest or *Agrobacterium* vector background, etc.

Southern Analysis: Plant transformation is confirmed by Southern blot analysis of genomic DNA (Sambrook and Russell, 2001). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}$P target DNA fragment to confirm the integration of introduced gene in the plant genome according to standard techniques (Sambrook and Russell, 2001. *Molecular Cloning: A Laboratory Manual*. Cold Spring Harbor Laboratory Press, Cold Spring Harbor, N.Y.).

Northern Analysis: RNA is isolated from specific tissues of transformant, fractionated in a formaldehyde agarose gel, blotted onto a nylon filter according to standard procedures that are routinely used in the art (Sambrook, J., and Russell, D. W. 2001. *Molecular Cloning: A Laboratory Manual*, Cold Spring Harbor Laboratory Press, Cold Spring Harbor, N.Y.). Expression of RNA encoded by the delta-endotoxin or delta-endotoxin-associated is then tested by hybridizing the filter to a radioactive probe derived from a delta-endotoxin or delta-endotoxin-associated protein, by methods known in the art (Sambrook and Russell, 2001).

Western blot and Biochemical assays: Western blot and biochemical assays and the like may be carried out on the transgenic plants to confirm the presence of protein encoded by the delta-endotoxin or delta-endotoxin-associated gene by standard procedures (Sambrook, J., and Russell, D. W. 2001. *Molecular Cloning: A Laboratory Manual*, Cold Spring Harbor Laboratory Press, Cold Spring Harbor, N.Y.) using antibodies that bind to one or more epitopes present on the delta-endotoxin or delta-endotoxin-associated protein.

Pesticidal Activity in Plants

In another aspect of the invention, one may generate transgenic plants expressing delta-endotoxin or delta-endotoxin-associated proteins that have pesticidal activity. Methods described above by way of example may be utilized to generate transgenic plants, but the manner in which the transgenic plant cells are generated is not critical to this invention. Methods known or described in the art such as *Agrobacterium*-mediated transformation, aerosol beam, biolistic transformation, and non-particle-mediated methods may be used at the discretion of the experimenter. Plants expressing delta-endotoxin or delta-endotoxin-associated proteins may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene).

Fertile plants expressing a delta-endotoxin or a delta-endotoxin-associated protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

Use in Pesticidal Control

General methods for employing the strains of the invention in pesticide control or in engineering other organisms as pesticidal agents are known in the art. See, for example U.S. Pat. No. 5,039,523 and EP 0480762A2.

The *Bacillus* strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a heterologous gene into a cellular host. Expression of the heterologous gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing the genes of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, mollusocides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be preparable by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leu-*

*copterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The following examples are offered by way of illustration and not by way of limitation.

EXPERIMENTAL

Example 1

Extraction of Plasmid DNA

A pure culture of strain ATX13026 was grown in large quantities of rich media. The culture was spun to harvest the cell pellet. The cell pellet was then prepared by treatment with SDS by methods known in the art, resulting in breakage of the cell wall and release of DNA. Proteins and large genomic DNA was then precipitated by a high salt concentration. The plasmid DNA was then precipitated by standard ethanol precipitation. The plasmid DNA was separated from any remaining chromosomal DNA by high-speed centrifugation through a cesium chloride gradient. The DNA was visualized in the gradient by UV light and the band of lower density (i.e. the lower band) was extracted using a syringe. This band contained the plasmid DNA from strain ATX 13026. The quality of the DNA was checked by visualization on an agarose gel by methods known in the art.

Example 2

Cloning of Genes

The purified plasmid DNA was sheared into 5-10 kb sized fragments and the 5' and 3' single stranded overhangs repaired using T4 DNA polymerase and Klenow fragment in the presence of all four dNTPs, as known in the art. Phosphates were then attached to the 5' ends by treatment with T4 polynucleotide kinase, as known in the art. The repaired DNA fragments were then ligated overnight into a standard high copy vector (i.e. pBluescript SK+), suitably prepared to accept the inserts as known in the art (for example by digestion with a restriction enzyme producing blunt ends).

The quality of the library was analyzed by digesting a subset of clones with a restriction enzyme known to have a cleavage site flanking the cloning site. A high percentage of clones were determined to contain inserts, with an average insert size of 5-6 kb.

Example 3

High Throughput Sequencing of Library Plates

Once the shotgun library quality was checked and confirmed, colonies were grown in a rich broth in 2 ml 96-well blocks overnight at 37° C. at a shaking speed of 350 rpm. The blocks were spun to harvest the cells to the bottom of the block. The blocks were then prepared by standard alkaline lysis prep in a high throughput format.

The end sequences of clones from this library were then determined for a large number of clones from each block in the following way: The DNA sequence of each clone chosen for analysis was determined using the fluorescent dye terminator sequencing technique (Applied Biosystems) and standard primers flanking each side of the cloning site. Once the reactions had been carried out in the thermocycler, the DNA was precipitated using standard ethanol precipitation. The DNA was resuspended in water and loaded onto a capillary sequencing machine. Each library plate of DNA was sequenced from either end of the cloning site, yielding two reads per plate over each insert.

Example 4

Assembly and Screening of Sequencing Data

DNA sequences obtained were compiled into an assembly project and aligned together to form contigs. This can be done efficiently using a computer program, such as Vector NTi, or alternatively by using the Pred/Phrap suite of DNA alignment and analysis programs. These contigs, along with any individual read that may not have been added to a contig, were compared to a compiled database of all classes of known pesticidal genes. Contigs or individual reads identified as having identity to a known endotoxin or pesticidal gene were analyzed further. Among the sequences obtained, clone pAX008 contained DNA identified as having homology to known endotoxin genes. Therefore, pAX008 was selected for further sequencing.

Example 5

Sequencing of pAX008, and Identification of AXMI-008

Primers were designed to anneal to pAX008, in a manner such that DNA sequences generated from such primers will overlap existing DNA sequence of the clone(s). This process, known as "oligo walking," is well known in the art. This process was utilized to determine the entire DNA sequence of the region exhibiting homology to a known endotoxin gene. In the case of pAX008, this process was used to determine the DNA sequence of the entire clone, resulting in a single nucleotide sequence. The completed DNA sequence was then placed back into the original large assembly for further validation. This allowed incorporation of more DNA sequence reads into the contig, resulting in multiple reads of coverage over the entire region.

Analysis of the DNA sequence of pAX008 by methods known in the art identified an open reading frame with homology to known delta endotoxin genes. This open reading frame is designated as AXMI-008. The DNA sequence of AXMI-008 is provided as SEQ ID NO:1, and the amino acid sequence of the predicted AMXI-008 protein is provided in SEQ ID NO:3. An alternate start site for AXMI-008 at nucleotide 177 of SEQ ID NO:1 generates the amino acid sequence provided as SEQ ID NO:5. Further analysis identified an open reading frame immediately 3' to the end of the AXMI-008 open reading frame. This predicted amino acid sequence of this orf, referred to herein as AXMI-008orf2, is provided in SEQ ID NO:7.

Example 6

Homology of AXMI-008 to Known Endotoxin Genes

Searches of DNA and protein databases with the DNA sequence and amino acid sequence of AXMI-008 reveal that AXMI-008 is homologous to known endotoxins.

Blast searches identify cry40Aa as having the strongest block of homology, and alignment of AMXI-008 protein (SEQ ID NO:3) to a large set of endotoxin proteins shows that the most homologous proteins is cry40Aa. The overall amino acid identity of cry40Aa to AXMI-008 is 66% (see Table 1). Inspection of the amino acid sequence of AXMI-008 suggests that it does not contain a C-terminal non-toxic domain as is present in several endotoxin families. By removing this C-terminal protein of the toxins from the alignment, the alignment reflects the amino acid identify present solely in the toxin domains (see Table 1, column three). This 'trimmed' alignment is shown in FIG. 1.

TABLE 1

Amino Acid Identity of AXMI-008 with Exemplary Endotoxin Classes

| Endotoxin | Percent Amino Acid Identity to AXMI-008 | Percent Amino Acid Identity of truncated Toxins to AXMI-008 |
| --- | --- | --- |
| cry1Aa | 11% | 20% |
| cry1Ac | 11% | 20% |
| cry1Ia | 22% | 22% |
| cry2A | 10% | 10% |
| cry3Aa | 21% | 21% |
| cry3Bb | 21% | 21% |
| cry4Aa | 13% | 21% |
| cry4Ba | 13% | 20% |
| cry6Aa | 5% | 5% |
| cry7Aa | 12% | 20% |
| cry8Aa | 13% | 22% |
| cry10Aa | 20% | 20% |
| cry16Aa | 22% | 22% |
| cry19Ba | 21% | 22% |
| cry24Aa | 26% | 26% |
| cry25Aa | 23% | 23% |
| cry39Aa | 25% | 25% |
| cry40Aa | 66% | 66% |

Example 7

Figure 2B:
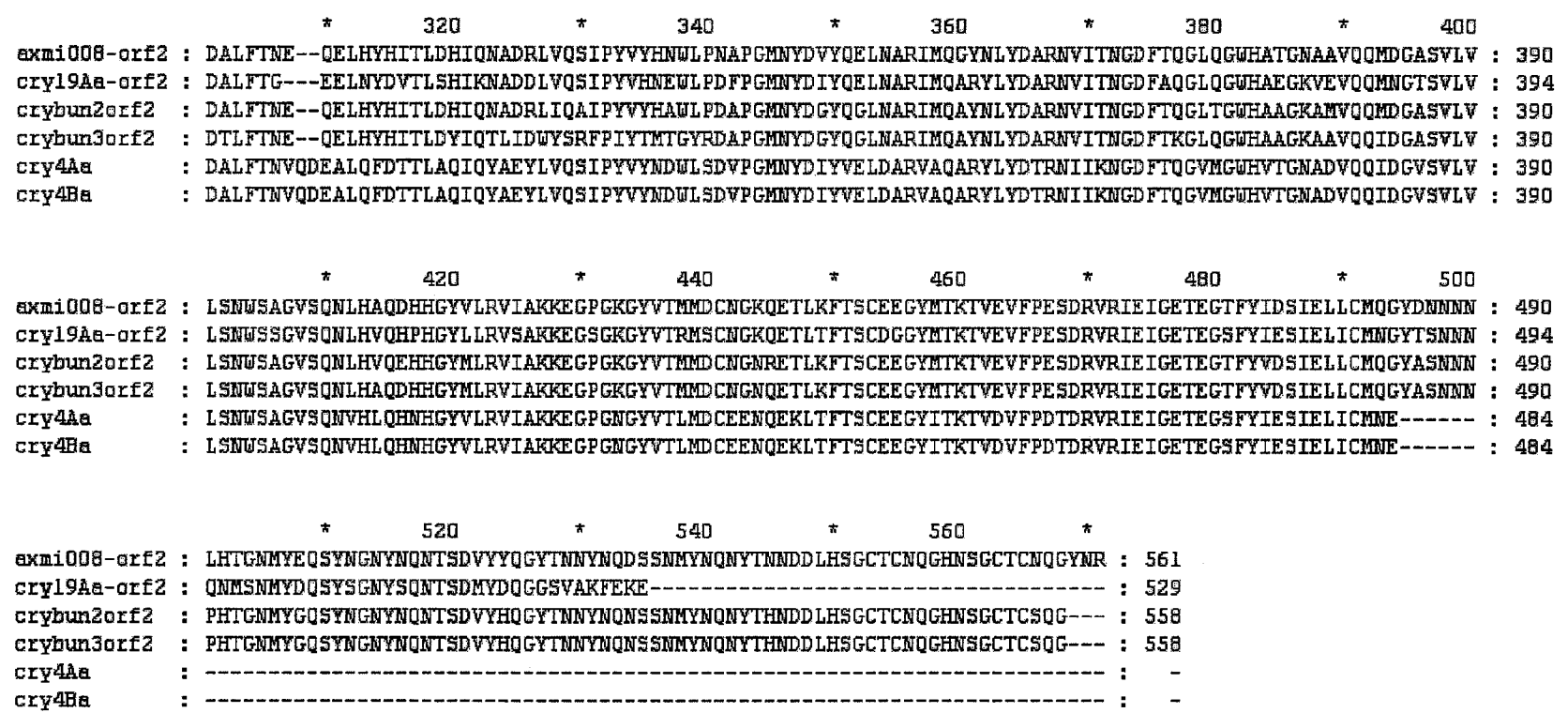

The ORF Immediately Downstream of AXMI-008 is Homologous to Downstream ORFs of Several Endotoxins The open reading frame immediately downstream (3') to the AXMI-008 coding region has homology to known endotoxin-related proteins. Blast searches identify crybun3 orf2 (the downstream orf of cry40Aa) as having the strongest block of homology. Several other orf-2 like proteins are present in databases, and an alignment of AMXI-008 protein (SEQ ID NO:3) to a set of these proteins is shown in FIG. 2. These proteins also share homology to the C-terminal non-toxic domain of cry4Aa and cry4Ba. The overall amino acid identity of AXMI-8-orf2 to cry40Aaorf2 is 86% (see Table 2).

TABLE 2

Amino acid identity of AXMI-008-orf2 to related proteins

| Protein | Percent amino acid identity to AXMI-008-orf2 |
| --- | --- |
| crybun3orf2 (cry40Aa orf2) | 86% |
| crybun2orf2 (cry39Aa orf2) | 85% |
| cry19Aorf2 | 62% |
| C-terminus cry4Aa | 53% |
| C-terminus cry4Ba | 54% |

Example 8

Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*.

CRC, Boca Raton, Fla. Alternatively, assays are commonly described in the journals "Arthropod Management Tests" and "Journal of Economic Entomology" or by discussion with members of the Entomological Society of America (ESA).

Example 9

Bioassay of pAX008 on *Trichoplusia ni* (Cabbage Looper)

An *Escherichia coli* strain containing pAX008, as well as a culture of untransformed *Escherichia coli* were grown in 2 ml of LB Broth (Luria-Bertani Broth, Becton Dickinson & Company, Sparks, Md.) for 24 hours at 37° C. with agitation at 250 rpm. pAX-008 was grown in LB containing the appropriate antibiotic to select for maintenance of the plasmid in *E. coli*.

Bioassays were performed using artificial diet (Multiple Species Diet, Southland Products, Lake Village, Ark.) in 24 well tissue culture plates. Bioassays were carried out by applying the *Escherichia coli* culture containing pAX-008 to the diet surface and allowing the diet surface to dry. The strains were applied as whole cultures to the diet at a concentration of 40 µl of culture per well. The bioassays were held in the dark at 25° C. and 65% relative humidity. Trays were sealed with Breathe Easy Sealing Tape (Diversified Biotech, Boston, Mass.). Results were recorded at 5 days.

TABLE 3

Assay of AXMI-008 clone pAX008 on *T. ni*

| Sample | # Dead/Total | % Mortality |
|---|---|---|
| pAX-008 | 6/6 | 100% |
| Negative Control | 0/13 | 0% |

Example 10

Expression of AXMI-008 in *Bacillus*

The 1,890 base pair insecticidal axmi008 gene was amplified by PCR from pAX008, and cloned into the *Bacillus* Expression vector pAX922 by methods well known in the art. The resulting clone, pAX922, expressed AXMI-008 protein when transformed into cells of a cry(−) *Bacillus thuringiensis* strain. The *Bacillus* strain containing pAX922 and expressing the AXMI-008 insecticidal protein may be cultured on a variety of conventional growth media. A *Bacillus* strain containing pAX922 was grown in CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation was evident by microscopic examination. Samples were prepared, and AXMI-008 was tested for insecticidal activity in bioassays against important insect pests.

Example 11

Bioassay of AXMI-008 on *Tenebrio molitor*

Samples of *Bacillus* cultures expressing AXMI-008 were prepared and tested for pesticidal activity on *Tenebrio molitor*. When pAX 922 is prepared as an insoluble fraction at pH 4.0 it showed activity against commonly called the yellow mealworm.

Samples of AXMI-008 were prepared from a culture of a *Bacillus* strain containing pAX 922. The bioassay sample was prepared by growing a culture in CYS media for 4 days, until sporulation. The sample was centrifuged at 10,000 rpm for 10 minutes and the supernatant discarded. The pellet was washed in 20 mM Tris pH 8 and spun at 10,000 rpm for 10 minutes. The supernatant was discarded and the pellet resuspended in 3 mls of 50 mM Sodium Citrate and 25 mM Sodium Chloride with 2 mM DTT at pH 4. The sample was incubated at 37° C. for 1 hour. After incubation the sample was spun at 13,000 rpm for 10 minutes and the supernatant discarded. The pellet was resuspended in 50 mM Sodium Citrate and 25 mM Sodium Chloride at pH 4.

Bioassays of samples on *Tenebrio molitor* were performed on an artificial diet (Southern Corn Rootworm Diet, Bioserv, Frenchtown, N.J., #F9757B) in 24 well tissue culture plates. The sample was applied as a surface treatment with a concentration of Axmi008 at 8 $ug/cm^2$ and allowed to air dry. The insects were applied using a fine tip brush. Bioassay trays were sealed with Breathe Easy Sealing Tape (Diversified Biotech, Boston, Mass.) and incubated without light at 65% relative humidity, 25° C. for seven days and results recorded.

TABLE 4

Assay of AXMI-008 clone pAX008 on *T. molitor*

| Sample | # Dead/Total | % Mortality |
|---|---|---|
| pAX922 | 3 of 4 | 75%* |

*Remaining *Tenebrio molitor* was stunted. Stunting is observed as reduced larval size and growth, and severely reduced or minimal feeding. The insect may also demonstrate avoidance of the treated diet compared to the untreated diet.

Methods

To prepare CYS media: 10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$. The CYS mix should be pH 7, if adjustment is necessary. NaOH or HCl are preferred. The media is then autoclaved and 100 ml of 10× filtered glucose is added after autoclaving. If the resultant solution is cloudy it can be stirred at room temperature to clear.

Example 12

Vectoring of AXMI-008 for Plant Expression

The AXMI-008 coding region DNA is operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

Example 13

Transformation of Maize Cells with AXMI-008

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 µL/L (of 1000× Stock) N6 Vitamins; 800 mg/L L-Asparagine; 100 mg/L Myoinositol; 1.4 g/L L-Proline; 100 mg/L Casaminoacids; 50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express AXMI-008 in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

| Components | Materials DN62A5S Media per liter | Source |
|---|---|---|
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 14

Transformation of AXMI-008 into Plant Cells by Agrobacterium-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an Agrobacterium strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated nucleic acid molecule selected from the group consisting of:
   a) a nucleic acid molecule comprising the nucleotide sequence of SEQ ID NO:1, 2, or 4; and,
   b) a nucleic acid molecule which encodes a polypeptide comprising the amino acid sequence of SEQ ID NO:3 or 5.

2. The isolated nucleic acid molecule of claim 1, wherein said nucleotide sequence is a synthetic sequence that has been designed for expression in a plant.

3. The nucleic acid molecule of claim 2, wherein said synthetic sequence has an increased GC content relative to the GC content of SEQ ID NO:1, 2, or 4.

4. A vector comprising the nucleic acid molecule of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A method for producing a polypeptide with pesticidal activity, comprising culturing the host cell of claim 6 under conditions in which the nucleic acid molecule encoding the polypeptide is expressed.

13. A plant having stably incorporated into its genome a DNA construct comprising a nucleotide sequence that encodes a protein having pesticidal activity, wherein said nucleotide sequence is selected from the group consisting of:
   a) the nucleotide sequence of SEQ ID NO: 1, 2, or 4; and,
   b) a nucleotide sequence encoding a polypeptide comprising the amino acid sequence of SEQ ID NO:3 or 5;
   wherein said nucleotide sequence is operably linked to a promoter that drives expression of a coding sequence in a plant cell.

14. A plant cell having stably incorporated into its genome a DNA construct comprising a nucleotide sequence that encodes a protein having pesticidal activity, wherein said nucleotide sequence is selected from the group consisting of:
   a) the nucleotide sequence of SEQ ID NO:1, 2, or 4; and,
   b) a nucleotide sequence encoding a polypeptide comprising the amino acid sequence of SEQ ID NO:3 or 5;
   wherein said nucleotide sequence is operably linked to a promoter that drives expression of a coding sequence in a plant cell.

* * * * *

SEQUENCE LISTING

<160> NUMBER OF SEQ ID NOS: 28

<210> SEQ ID NO 1
<211> LENGTH: 5980
<212> TYPE: DNA
<213> ORGANISM: Bacillus thuringiensis

<400> SEQUENCE: 1

| | | | | | |
|---|---|---|---|---|---|
| tacatgcaat | acataaagag | aaggtttaaa | aaatcaatac | ctcaccaaaa | ataatgggtt | 60 |
| tatttgtaga | aacattgtta | caggaataca | ttggggtact | acgaatatat | agaaagacac | 120 |
| ctaacatata | tttattaggt | gtcttaaaaa | taaggactat | ataaggagtg | aaaaagatga | 180 |
| gtccatatca | aaataaaaat | gaatatgaaa | tattggaatc | ctcatcgaat | aacacaaata | 240 |
| cgccaaacag | atatcctttt | gcaaataatc | gggatatgtc | tactatgtct | tggaatgatt | 300 |
| gtcagggaat | ctcatgggat | gaaatttggg | aatcagtcga | aacgataaca | agtattggga | 360 |
| taaatcttat | agagtttgtg | atagaaccta | gtttgggtgg | aattaataca | ctattatcaa | 420 |
| taataggaaa | actaattccg | actaatcgtc | aaactgtgtc | agcactttct | atatgtgatt | 480 |
| tattatctat | aattcgtaaa | gaggtagccg | atagtgtttt | aagtgatgcg | attgcagatt | 540 |
| ttgacggtaa | attgaaaaat | tatagagagt | attatctttc | ttatcttggg | gcttggctta | 600 |
| aagacggtaa | accacttcaa | aagacaaata | attctgatat | cggacaatta | gtttattatt | 660 |
| ttaaactttc | agaagagat | ttcaatgaaa | ttctaggagg | gtcattgtca | agaaacaatg | 720 |
| ctcaagtatt | gttattacct | acttttgcac | aagctgcaaa | tgtgcagtta | ttactattaa | 780 |
| gggatgcagt | tcaatataaa | gcacaatggt | tcccattttt | gagtgcagag | aatgtaagat | 840 |
| cggaattaat | atcacctaac | agtggttgtg | attttaccgg | tgattactat | gagcgattaa | 900 |
| aatgcaaaac | ggcagagtat | accaattatt | gtttatattg | gtatcaggta | ggtttaaatc | 960 |
| agataaaaca | ggggggaca | ggtgctgaca | cttggtcgaa | atttaataaa | tttcgtagag | 1020 |
| aaatgacgtt | ggcggtattg | gatattatcg | ctatatttcc | aacttatgat | tttgagaaat | 1080 |
| atccattgcc | aacacatgta | gagttgacta | gggaaattta | tacagatgca | gtgggatatt | 1140 |
| catcgggaac | ttatagttgg | ttacggaatt | ggcctaatac | ttttaatggg | ttagaggcta | 1200 |
| atggaacacg | gggacctggt | ttagttactt | ggcttagcaa | aataggtata | tataatgagt | 1260 |
| atgtttcgag | atattttgcc | ggctgggtag | gaactcgtca | ttatgaagac | tacacaaagg | 1320 |
| gtaacggtat | ttttcaacgt | atgtctggaa | ctacgagtaa | tgatctacgt | aatattgatt | 1380 |
| ttcagaatgc | cgatgtatat | aaaattactt | cattagctat | catgaaccta | gtaggagaga | 1440 |
| ctaccgctag | accagagtat | cgtgtttcaa | aggcagattt | tcgtagggta | gggggacctg | 1500 |
| atttaaatta | tgatgcaggt | aataatgggc | taagcaggat | gacaattgaa | tctacgttcc | 1560 |
| cacttgtatt | gcactctaat | ggtgttagag | gaccctctca | tagattatca | aatgcggcat | 1620 |
| gtgttgtata | tggaaactcc | agagttaacg | tatatggttg | gacacataca | agtttaaaac | 1680 |
| gtgaaaatat | aattgaagcc | aatcaaatta | cacaaatacc | ggcggtgaag | agttattacc | 1740 |
| ttcaaaatta | tcttgctaat | gcctatacct | atgtaataaa | aggcactcat | acaggtgggg | 1800 |
| atttaatccg | ttttttaaga | acaaaatcag | agtataacgc | agtttatgca | ggtggcggaa | 1860 |
| ttagattgat | tattaataac | aaaactgcag | gacaaagtta | ccgtattcgt | tttcgttatg | 1920 |
| ctgcagataa | agctgcttc | tttagtgtat | atctttatcc | aggaggttgg | ggttcaaatc | 1980 |
| gttttgtatc | gcttgaaaaa | tcttactctg | gaaattatga | cgatttaaaa | tatagtgatt | 2040 |

-continued

```
ttaaattcgc tgaaattatc acacctccat tacctagttc aaacattcag atggatgtgg    2100
agatgcaagc gaatagtttt caatcagatg taaacgtggt tctcgacaaa attgaattcc    2160
tcccaagtaa tacaacaact ttagaatatg agggagaacg ggacctagaa aaaacaaaga    2220
acgcggtgaa cgatctgttt accaattaaa acaaataat ttactagaat aggtggtatt     2280
gctgtttaac aaataagcga aaaaggttgt gagtcctatg tttacaagta gtacgaaaaa    2340
tacgttaaaa atagaaacga cagattatga aatagatcaa gcggccattt ctatagaatg    2400
tatgtcagat gaacaaaatc ctcaggaaaa ataatgtta tgggatgaaa taaaactggc     2460
aaaacaactt agtcagtctc gtaatctact ccaaaatgga acttttctg gaatgattg      2520 gacattcggt aatgatatta tcataggatc caataatcct attttaaag gaaaatttct     2580 acagatgcgt ggagcacgag acatatatgg aactctattt ccaacctata tctgtcaaaa    2640
aatagatgag tctaaattaa aaccatatac acgttatcga gtaagagggt tgtgggaag     2700 tagtaaagat ttgaaattaa tggtaacacg ttacgggaaa gaaattgatg ctatcatgaa    2760
tgttccaaat gatttggcct atatgcagcc taatccttca tgtggagatt atcgctgtga    2820
atcatcgtct cagtatgtga gccaagggta tcctacacca acagatggat atgctcccga    2880
tatgtatgca tgcccgcaaa atatagatag aaagcatgtg aagtgtcacg atcgtcatcc    2940
atttgatttt catattgaca ccggagaagt agatacaaat acaaatgtag gtattgatgt    3000
cttattaaaa atttctaatc cagatggata cgctacagta gggaatctag aagtcattga    3060
agaaggacca ctaacaggtg aagcattggc acatgtgaaa caaaaggaaa agaaatggaa    3120
acaacacatg gagaaaaaac gttgggaaac acaacaagcc tatgatccag caaaacaggc    3180
tgtagatgca ttatttacaa atgaacaaga gttacactat catattactt tagatcatat    3240
tcaaaacgct gatcgactgg tacagtcgat tccctatgta taccataatt ggttaccgaa    3300
tgctccaggt atgaactatg atgtatatca agagttaaac gcacgtatca tgcaaggtta    3360
taatttatat gatgcacgaa atgtcataac aaatggtgac tttacacaag gattacaggg    3420
atggcacgca acaggaaatg ccgcggtaca acaaatggat ggagcttcag tattagttct    3480
atcaaattgg agcgcggggg tatctcaaaa cttgcatgct caagatcatc atggatatgt    3540
gttacgtgtg attgccaaaa aagaaggacc tggaaaaggg tatgtaacga tgatggattg    3600
taatggaaag caggaaacac ttaagttcac ttcttgcgaa gaaggatata tgacaaaaac    3660
agtagaggta ttcccagaaa gtgatcgtgt acggattgaa ataggagaaa ccgaaggtac    3720
attttatata gatagcatcg agttgctttg tatgcaagga tatgataaca ataataacct    3780
gcacacgggt aatatgtatg agcaaagtta taatggaaat tataatcaaa atactagcga    3840
tgtgtattac caagggtata caaacaacta taaccaagac tctagtaata tgtataatca    3900
aaattatact aacaatgatg acctgcattc cggttgcaca tgtaaccaag gcataactc     3960 tggctgtaca tgtaatcaag gatataaccg ttaacgattc taaataagaa tcaacatcat    4020
tgcgaaaaat aaaaacctac tcacaaaatc tattgcatat cataacataa gctttacaaa    4080
taacggacat attctagaag aggtctcctt aattctaaaa taaggagatt ttttcgttt     4140 ccccaatatt gattaatgaa aatactcctt tacagaaaga tttaggctga ttggtgtttt    4200
gtgcaagcag caattcctga aaaatgcaga aaaaattcca gaggcatgca gctactttt     4260 taaatgttaa ttttggtatt tccagaagat aaagcatttc gtaaacgata actttcacct    4320
gtgaatgcaa tgatatgagc atgatggacc aaacggtcca ccaatgcaga agtaagccgg    4380
```

-continued

```
ttatcaccaa atatacgatt ccattgacca aattctaagt ttgaagtaac tatgacactt   4440
ttttgttcgt aacagtcggc aataatatga aataggagct ccgctccttg cttttgaaat   4500
ggtacataac ctagttcatc taaaattaat aaatcacagg cttcaatttg cttcttgatg   4560
cgggttaaat tcccttgttt taaagcctct tctaatagac ctactaaatc tgctactcgg   4620
aaaaacttca cttgatatcc ctgttcacaa gccttcaaac ctaatgctgt agctaaatgt   4680
gttttcccag ttccaggaga tccaagtaat aaaagatttt gtttcccttc aaaaaatcgc   4740
aattcacaaa tgtgttcttg attcgttgta gatggcagat gaatttgttc actccattca   4800
taattcttga gccattttaa ctctcgaaat ttcgctttct tgattaagtt tgctactttt   4860
ttcgtttgac gagattcaat ctctatattg aaaatatcac gcagaaattg ttctttggtt   4920
tcaaaaggta tttcatcata atggtctata atatagctta aatgcagtga tttacaggcg   4980
tcttgcaggt ttcgttgtat cataatgaga atgaacccct ttctaaagtt ggacaaagct   5040
ttcgatcata ttgctgaaga tctgtttcgt aatctattaa aacaggtggc gtatggtttt   5100
cttgccattt ttgtggatac gtcacttgtt gagtctgcaa tatgatatcg agttcgtgag   5160
gagctttttt caaccattct tcattctcta acagtaagtg tagctgctgt aatgagtatt   5220
tttgaattaa atatttgaat cctgttaaac aagcttttct ttcatcctta tgaaagagca   5280
gataatcttg aacccgctga ggtaaatatt tgaaaaatct agaataacga acaacgcgtg   5340
gtttcttttc ccaatcttca aaaatctctt cccatagaat cggcctactc gtgtgcatat   5400
acggtctgta ttctgtaaaa atgttctcgc cttctgcggt ataacatgta aattgatccc   5460
attctttttt aatgataatc acttgtttta cgtaaaacaa aacgttcttg atccactgtg   5520
atttctccat atttatttac cgttgttgtg tccattgaga agaccgttag gtcttccaaa   5580
ggtaatggtt tcaatgcagc cttatcatca ttccaaaggt cttcaatcat gacttccttc   5640
tcataatgta ggcgtttctg atcttctatt gcttgtactt ctaaccattg tgcgagttga   5700
gaaaaactct ccataatcgg agcggttgta aaccaattgt ttcgtgtata actgactttc   5760
cgttcaacgt tccccttttc atgcccgcta taaggattac aaggttgcac ttcaaagtta   5820
taatgcattt gaaattgtaa aaatgcatcc gtataagttc gattatcacc ttttcctact   5880
gtgactacag cggcagataa gttatcaatt cgaagatgcg ttggtacacc accagcttga   5940
tgaaataatc gttttaagcc ttctaaaaag ccttctgtat                         5980

<210> SEQ ID NO 2
<211> LENGTH: 2082
<212> TYPE: DNA
<213> ORGANISM: Bacillus thuringiensis
<220> FEATURE:
<221> NAME/KEY: CDS
<222> LOCATION: (1)...(2082)

<400> SEQUENCE: 2 gtg aaa aag atg agt cca tat caa aat aaa aat gaa tat gaa ata ttg        48
Met Lys Lys Met Ser Pro Tyr Gln Asn Lys Asn Glu Tyr Glu Ile Leu
 1               5                  10                  15 gaa tcc tca tcg aat aac aca aat acg cca aac aga tat cct ttt gca        96
Glu Ser Ser Ser Asn Asn Thr Asn Thr Pro Asn Arg Tyr Pro Phe Ala
            20                  25                  30 aat aat cgg gat atg tct act atg tct tgg aat gat tgt cag gga atc       144
Asn Asn Arg Asp Met Ser Thr Met Ser Trp Asn Asp Cys Gln Gly Ile
        35                  40                  45 tca tgg gat gaa att tgg gaa tca gtc gaa acg ata aca agt att ggg       192
Ser Trp Asp Glu Ile Trp Glu Ser Val Glu Thr Ile Thr Ser Ile Gly
```

```
                                -continued
        50                  55                  60
ata aat ctt ata gag ttt gtg ata gaa cct agt ttg ggt gga att aat       240
Ile Asn Leu Ile Glu Phe Val Ile Glu Pro Ser Leu Gly Gly Ile Asn
 65                  70                  75                  80 aca cta tta tca ata ata gga aaa cta att ccg act aat cgt caa act       288
Thr Leu Leu Ser Ile Ile Gly Lys Leu Ile Pro Thr Asn Arg Gln Thr
                 85                  90                  95 gtg tca gca ctt tct ata tgt gat tta tta tct ata att cgt aaa gag       336
Val Ser Ala Leu Ser Ile Cys Asp Leu Leu Ser Ile Ile Arg Lys Glu
            100                 105                 110 gta gcc gat agt gtt tta agt gat gcg att gca gat ttt gac ggt aaa       384
Val Ala Asp Ser Val Leu Ser Asp Ala Ile Ala Asp Phe Asp Gly Lys
        115                 120                 125 ttg aaa aat tat aga gag tat tat ctt tct tat ctt ggg gct tgg ctt       432
Leu Lys Asn Tyr Arg Glu Tyr Tyr Leu Ser Tyr Leu Gly Ala Trp Leu
    130                 135                 140 aaa gac ggt aaa cca ctt caa aag aca aat aat tct gat atc gga caa       480
Lys Asp Gly Lys Pro Leu Gln Lys Thr Asn Asn Ser Asp Ile Gly Gln
145                 150                 155                 160 tta gtt tat tat ttt aaa ctt tca gaa aga gat ttc aat gaa att cta       528
Leu Val Tyr Tyr Phe Lys Leu Ser Glu Arg Asp Phe Asn Glu Ile Leu
                165                 170                 175 gga ggg tca ttg tca aga aac aat gct caa gta ttg tta tta cct act       576
Gly Gly Ser Leu Ser Arg Asn Asn Ala Gln Val Leu Leu Leu Pro Thr
            180                 185                 190 ttt gca caa gct gca aat gtg cag tta tta cta tta agg gat gca gtt       624
Phe Ala Gln Ala Ala Asn Val Gln Leu Leu Leu Leu Arg Asp Ala Val
        195                 200                 205 caa tat aaa gca caa tgg ttc cca ttt ttg agt gca gag aat gta aga       672
Gln Tyr Lys Ala Gln Trp Phe Pro Phe Leu Ser Ala Glu Asn Val Arg
    210                 215                 220 tcg gaa tta ata tca cct aac agt ggt tgt gat ttt acc ggt gat tac       720
Ser Glu Leu Ile Ser Pro Asn Ser Gly Cys Asp Phe Thr Gly Asp Tyr
225                 230                 235                 240 tat gag cga tta aaa tgc aaa acg gca gag tat acc aat tat tgt tta       768
Tyr Glu Arg Leu Lys Cys Lys Thr Ala Glu Tyr Thr Asn Tyr Cys Leu
                245                 250                 255 tat tgg tat cag gta ggt tta aat cag ata aaa cag ggg gga aca ggt       816
Tyr Trp Tyr Gln Val Gly Leu Asn Gln Ile Lys Gln Gly Gly Thr Gly
            260                 265                 270 gct gac act tgg tcg aaa ttt aat aaa ttt cgt aga gaa atg acg ttg       864
Ala Asp Thr Trp Ser Lys Phe Asn Lys Phe Arg Arg Glu Met Thr Leu
        275                 280                 285 gcg gta ttg gat att atc gct ata ttt cca act tat gat ttt gag aaa       912
Ala Val Leu Asp Ile Ile Ala Ile Phe Pro Thr Tyr Asp Phe Glu Lys
    290                 295                 300 tat cca ttg cca aca cat gta gag ttg act agg gaa att tat aca gat       960
Tyr Pro Leu Pro Thr His Val Glu Leu Thr Arg Glu Ile Tyr Thr Asp
305                 310                 315                 320 gca gtg gga tat tca tcg gga act tat agt tgg tta cgg aat tgg cct      1008
Ala Val Gly Tyr Ser Ser Gly Thr Tyr Ser Trp Leu Arg Asn Trp Pro
                325                 330                 335 aat act ttt aat ggg tta gag gct aat gga aca cgg gga cct ggt tta      1056
Asn Thr Phe Asn Gly Leu Glu Ala Asn Gly Thr Arg Gly Pro Gly Leu
            340                 345                 350 gtt act tgg ctt agc aaa ata ggt ata tat aat gag tat gtt tcg aga      1104
Val Thr Trp Leu Ser Lys Ile Gly Ile Tyr Asn Glu Tyr Val Ser Arg
        355                 360                 365 tat ttt gcc ggc tgg gta gga act cgt cat tat gaa gac tac aca aag      1152
```

```
Tyr Phe Ala Gly Trp Val Gly Thr Arg His Tyr Glu Asp Tyr Thr Lys
        370                 375                 380 ggt aac ggt att ttt caa cgt atg tct gga act acg agt aat gat cta      1200
Gly Asn Gly Ile Phe Gln Arg Met Ser Gly Thr Thr Ser Asn Asp Leu
385                 390                 395                 400 cgt aat att gat ttt cag aat gcc gat gta tat aaa att act tca tta      1248
Arg Asn Ile Asp Phe Gln Asn Ala Asp Val Tyr Lys Ile Thr Ser Leu
                405                 410                 415 gct atc atg aac cta gta gga gag act acc gct aga cca gag tat cgt      1296
Ala Ile Met Asn Leu Val Gly Glu Thr Thr Ala Arg Pro Glu Tyr Arg
            420                 425                 430 gtt tca aag gca gat ttt cgt agg gta ggg gga cct gat tta aat tat      1344
Val Ser Lys Ala Asp Phe Arg Arg Val Gly Gly Pro Asp Leu Asn Tyr
        435                 440                 445 gat gca ggt aat aat ggg cta agc agg atg aca att gaa tct acg ttc      1392
Asp Ala Gly Asn Asn Gly Leu Ser Arg Met Thr Ile Glu Ser Thr Phe
450                 455                 460 cca ctt gta ttg cac tct aat ggt gtt aga gga ccc tct cat aga tta      1440
Pro Leu Val Leu His Ser Asn Gly Val Arg Gly Pro Ser His Arg Leu
465                 470                 475                 480 tca aat gcg gca tgt gtt gta tat gga aac tcc aga gtt aac gta tat      1488
Ser Asn Ala Ala Cys Val Val Tyr Gly Asn Ser Arg Val Asn Val Tyr
                485                 490                 495 ggt tgg aca cat aca agt tta aaa cgt gaa aat ata att gaa gcc aat      1536
Gly Trp Thr His Thr Ser Leu Lys Arg Glu Asn Ile Ile Glu Ala Asn
            500                 505                 510 caa att aca caa ata ccg gcg gtg aag agt tat tac ctt caa aat tat      1584
Gln Ile Thr Gln Ile Pro Ala Val Lys Ser Tyr Tyr Leu Gln Asn Tyr
        515                 520                 525 ctt gct aat gcc tat acc tat gta ata aaa ggc act cat aca ggt ggg      1632
Leu Ala Asn Ala Tyr Thr Tyr Val Ile Lys Gly Thr His Thr Gly Gly
530                 535                 540 gat tta atc cgt ttt tta aga aca aaa tca gag tat aac gca gtt tat      1680
Asp Leu Ile Arg Phe Leu Arg Thr Lys Ser Glu Tyr Asn Ala Val Tyr
545                 550                 555                 560 gca ggt ggc gga att aga ttg att att aat aac aaa act gca gga caa      1728
Ala Gly Gly Gly Ile Arg Leu Ile Ile Asn Asn Lys Thr Ala Gly Gln
                565                 570                 575 agt tac cgt att cgt ttt cgt tat gct gca gat aaa gct gct ttc ttt      1776
Ser Tyr Arg Ile Arg Phe Arg Tyr Ala Ala Asp Lys Ala Ala Phe Phe
            580                 585                 590 agt gta tat ctt tat cca gga ggt tgg ggt tca aat cgt ttt gta tcg      1824
Ser Val Tyr Leu Tyr Pro Gly Gly Trp Gly Ser Asn Arg Phe Val Ser
        595                 600                 605 ctt gaa aaa tct tac tct gga aat tat gac gat tta aaa tat agt gat      1872
Leu Glu Lys Ser Tyr Ser Gly Asn Tyr Asp Asp Leu Lys Tyr Ser Asp
610                 615                 620 ttt aaa ttc gct gaa att atc aca cct cca tta cct agt tca aac att      1920
Phe Lys Phe Ala Glu Ile Ile Thr Pro Pro Leu Pro Ser Ser Asn Ile
625                 630                 635                 640 cag atg gat gtg gag atg caa gcg aat agt ttt caa tca gat gta aac      1968
Gln Met Asp Val Glu Met Gln Ala Asn Ser Phe Gln Ser Asp Val Asn
                645                 650                 655 gtg gtt ctc gac aaa att gaa ttc ctc cca agt aat aca aca act tta      2016
Val Val Leu Asp Lys Ile Glu Phe Leu Pro Ser Asn Thr Thr Thr Leu
            660                 665                 670 gaa tat gag gga gaa cgg gac cta gaa aaa aca aag aac gcg gtg aac      2064
Glu Tyr Glu Gly Glu Arg Asp Leu Glu Lys Thr Lys Asn Ala Val Asn
        675                 680                 685
```

```
gat ctg ttt acc aat taa                                              2082
Asp Leu Phe Thr Asn *
        690
```

<210> SEQ ID NO 3
<211> LENGTH: 693
<212> TYPE: PRT
<213> ORGANISM: Bacillus thuringiensis

<400> SEQUENCE: 3

```
Met Lys Lys Met Ser Pro Tyr Gln Asn Lys Asn Glu Tyr Glu Ile Leu
 1               5                  10                  15

Glu Ser Ser Ser Asn Asn Thr Asn Thr Pro Asn Arg Tyr Pro Phe Ala
             20                  25                  30

Asn Asn Arg Asp Met Ser Thr Met Ser Trp Asn Asp Cys Gln Gly Ile
         35                  40                  45

Ser Trp Asp Glu Ile Trp Glu Ser Val Glu Thr Ile Thr Ser Ile Gly
     50                  55                  60

Ile Asn Leu Ile Glu Phe Val Ile Glu Pro Ser Leu Gly Gly Ile Asn
 65                  70                  75                  80

Thr Leu Leu Ser Ile Ile Gly Lys Leu Ile Pro Thr Asn Arg Gln Thr
                 85                  90                  95

Val Ser Ala Leu Ser Ile Cys Asp Leu Leu Ser Ile Ile Arg Lys Glu
            100                 105                 110

Val Ala Asp Ser Val Leu Ser Asp Ala Ile Ala Asp Phe Asp Gly Lys
        115                 120                 125

Leu Lys Asn Tyr Arg Glu Tyr Tyr Leu Ser Tyr Leu Gly Ala Trp Leu
    130                 135                 140

Lys Asp Gly Lys Pro Leu Gln Lys Thr Asn Asn Ser Asp Ile Gly Gln
145                 150                 155                 160

Leu Val Tyr Tyr Phe Lys Leu Ser Glu Arg Asp Phe Asn Glu Ile Leu
                165                 170                 175

Gly Gly Ser Leu Ser Arg Asn Asn Ala Gln Val Leu Leu Leu Pro Thr
            180                 185                 190

Phe Ala Gln Ala Ala Asn Val Gln Leu Leu Leu Arg Asp Ala Val
        195                 200                 205

Gln Tyr Lys Ala Gln Trp Phe Pro Phe Leu Ser Ala Glu Asn Val Arg
    210                 215                 220

Ser Glu Leu Ile Ser Pro Asn Ser Gly Cys Asp Phe Thr Gly Asp Tyr
225                 230                 235                 240

Tyr Glu Arg Leu Lys Cys Lys Thr Ala Glu Tyr Thr Asn Tyr Cys Leu
                245                 250                 255

Tyr Trp Tyr Gln Val Gly Leu Asn Gln Ile Lys Gln Gly Gly Thr Gly
            260                 265                 270

Ala Asp Thr Trp Ser Lys Phe Asn Lys Phe Arg Arg Glu Met Thr Leu
        275                 280                 285

Ala Val Leu Asp Ile Ile Ala Ile Phe Pro Thr Tyr Asp Phe Glu Lys
    290                 295                 300

Tyr Pro Leu Pro Thr His Val Glu Leu Thr Arg Glu Ile Tyr Thr Asp
305                 310                 315                 320

Ala Val Gly Tyr Ser Ser Gly Thr Tyr Ser Trp Leu Arg Asn Trp Pro
                325                 330                 335

Asn Thr Phe Asn Gly Leu Glu Ala Asn Gly Thr Arg Gly Pro Gly Leu
            340                 345                 350

Val Thr Trp Leu Ser Lys Ile Gly Ile Tyr Asn Glu Tyr Val Ser Arg
```

-continued

```
                355                 360                 365
Tyr Phe Ala Gly Trp Val Gly Thr Arg His Tyr Glu Asp Tyr Thr Lys
    370                 375                 380

Gly Asn Gly Ile Phe Gln Arg Met Ser Gly Thr Thr Ser Asn Asp Leu
385                 390                 395                 400

Arg Asn Ile Asp Phe Gln Asn Ala Asp Val Tyr Lys Ile Thr Ser Leu
                405                 410                 415

Ala Ile Met Asn Leu Val Gly Glu Thr Thr Ala Arg Pro Glu Tyr Arg
            420                 425                 430

Val Ser Lys Ala Asp Phe Arg Arg Val Gly Pro Asp Leu Asn Tyr
        435                 440                 445

Asp Ala Gly Asn Asn Gly Leu Ser Arg Met Thr Ile Glu Ser Thr Phe
    450                 455                 460

Pro Leu Val Leu His Ser Asn Gly Val Arg Gly Pro Ser His Arg Leu
465                 470                 475                 480

Ser Asn Ala Ala Cys Val Val Tyr Gly Asn Ser Arg Val Asn Val Tyr
                485                 490                 495

Gly Trp Thr His Thr Ser Leu Lys Arg Glu Asn Ile Ile Glu Ala Asn
            500                 505                 510

Gln Ile Thr Gln Ile Pro Ala Val Lys Ser Tyr Tyr Leu Gln Asn Tyr
        515                 520                 525

Leu Ala Asn Ala Tyr Thr Tyr Val Ile Lys Gly Thr His Thr Gly Gly
    530                 535                 540

Asp Leu Ile Arg Phe Leu Arg Thr Lys Ser Glu Tyr Asn Ala Val Tyr
545                 550                 555                 560

Ala Gly Gly Gly Ile Arg Leu Ile Ile Asn Asn Lys Thr Ala Gly Gln
                565                 570                 575

Ser Tyr Arg Ile Arg Phe Arg Tyr Ala Ala Asp Lys Ala Ala Phe Phe
            580                 585                 590

Ser Val Tyr Leu Tyr Pro Gly Gly Trp Gly Ser Asn Arg Phe Val Ser
        595                 600                 605

Leu Glu Lys Ser Tyr Ser Gly Asn Tyr Asp Asp Leu Lys Tyr Ser Asp
    610                 615                 620

Phe Lys Phe Ala Glu Ile Ile Thr Pro Pro Leu Pro Ser Ser Asn Ile
625                 630                 635                 640

Gln Met Asp Val Glu Met Gly Ala Asn Ser Phe Gln Ser Asp Val Asn
                645                 650                 655

Val Val Leu Asp Lys Ile Glu Phe Leu Pro Ser Asn Thr Thr Thr Leu
            660                 665                 670

Glu Tyr Glu Gly Glu Arg Asp Leu Glu Lys Thr Lys Asn Ala Val Asn
        675                 680                 685

Asp Leu Phe Thr Asn
    690
```

```
<210> SEQ ID NO 4
<211> LENGTH: 2073
<212> TYPE: DNA
<213> ORGANISM: Bacillus thuringiensis
<220> FEATURE:
<221> NAME/KEY: CDS
<222> LOCATION: (1)...(2073)

<400> SEQUENCE: 4 atg agt cca tat caa aat aaa aat gaa tat gaa ata ttg gaa tcc tca    48
Met Ser Pro Tyr Gln Asn Lys Asn Glu Tyr Glu Ile Leu Glu Ser Ser
1               5                   10                  15
```

```
tcg aat aac aca aat acg cca aac aga tat cct ttt gca aat aat cgg      96
Ser Asn Asn Thr Asn Thr Pro Asn Arg Tyr Pro Phe Ala Asn Asn Arg
             20                  25                  30 gat atg tct act atg tct tgg aat gat tgt cag gga atc tca tgg gat     144
Asp Met Ser Thr Met Ser Trp Asn Asp Cys Gln Gly Ile Ser Trp Asp
         35                  40                  45 gaa att tgg gaa tca gtc gaa acg ata aca agt att ggg ata aat ctt     192
Glu Ile Trp Glu Ser Val Glu Thr Ile Thr Ser Ile Gly Ile Asn Leu
     50                  55                  60 ata gag ttt gtg ata gaa cct agt ttg ggt gga att aat aca cta tta     240
Ile Glu Phe Val Ile Glu Pro Ser Leu Gly Gly Ile Asn Thr Leu Leu
 65                  70                  75                  80 tca ata ata gga aaa cta att ccg act aat cgt caa act gtg tca gca     288
Ser Ile Ile Gly Lys Leu Ile Pro Thr Asn Arg Gln Thr Val Ser Ala
                 85                  90                  95 ctt tct ata tgt gat tta tta tct ata att cgt aaa gag gta gcc gat     336
Leu Ser Ile Cys Asp Leu Leu Ser Ile Ile Arg Lys Glu Val Ala Asp
            100                 105                 110 agt gtt tta agt gat gcg att gca gat ttt gac ggt aaa ttg aaa aat     384
Ser Val Leu Ser Asp Ala Ile Ala Asp Phe Asp Gly Lys Leu Lys Asn
        115                 120                 125 tat aga gag tat tat ctt tct tat ctt ggg gct tgg ctt aaa gac ggt     432
Tyr Arg Glu Tyr Tyr Leu Ser Tyr Leu Gly Ala Trp Leu Lys Asp Gly
    130                 135                 140 aaa cca ctt caa aag aca aat aat tct gat atc gga caa tta gtt tat     480
Lys Pro Leu Gln Lys Thr Asn Asn Ser Asp Ile Gly Gln Leu Val Tyr
145                 150                 155                 160 tat ttt aaa ctt tca gaa aga gat ttc aat gaa att cta gga ggg tca     528
Tyr Phe Lys Leu Ser Glu Arg Asp Phe Asn Glu Ile Leu Gly Gly Ser
                165                 170                 175 ttg tca aga aac aat gct caa gta ttg tta tta cct act ttt gca caa     576
Leu Ser Arg Asn Asn Ala Gln Val Leu Leu Leu Pro Thr Phe Ala Gln
            180                 185                 190 gct gca aat gtg cag tta tta cta tta agg gat gca gtt caa tat aaa     624
Ala Ala Asn Val Gln Leu Leu Leu Leu Arg Asp Ala Val Gln Tyr Lys
        195                 200                 205 gca caa tgg ttc cca ttt ttg agt gca gag aat gta aga tcg gaa tta     672
Ala Gln Trp Phe Pro Phe Leu Ser Ala Glu Asn Val Arg Ser Glu Leu
    210                 215                 220 ata tca cct aac agt ggt tgt gat ttt acc ggt gat tac tat gag cga     720
Ile Ser Pro Asn Ser Gly Cys Asp Phe Thr Gly Asp Tyr Tyr Glu Arg
225                 230                 235                 240 tta aaa tgc aaa acg gca gag tat acc aat tat tgt tta tat tgg tat     768
Leu Lys Cys Lys Thr Ala Glu Tyr Thr Asn Tyr Cys Leu Tyr Trp Tyr
                245                 250                 255 cag gta ggt tta aat cag ata aaa cag ggg gga aca ggt gct gac act     816
Gln Val Gly Leu Asn Gln Ile Lys Gln Gly Gly Thr Gly Ala Asp Thr
            260                 265                 270 tgg tcg aaa ttt aat aaa ttt cgt aga gaa atg acg ttg gcg gta ttg     864
Trp Ser Lys Phe Asn Lys Phe Arg Arg Glu Met Thr Leu Ala Val Leu
        275                 280                 285 gat att atc gct ata ttt cca act tat gat ttt gag aaa tat cca ttg     912
Asp Ile Ile Ala Ile Phe Pro Thr Tyr Asp Phe Glu Lys Tyr Pro Leu
    290                 295                 300 cca aca cat gta gag ttg act agg gaa att tat aca gat gca gtg gga     960
Pro Thr His Val Glu Leu Thr Arg Glu Ile Tyr Thr Asp Ala Val Gly
305                 310                 315                 320 tat tca tcg gga act tat agt tgg tta cgg aat tgg cct aat act ttt    1008
Tyr Ser Ser Gly Thr Tyr Ser Trp Leu Arg Asn Trp Pro Asn Thr Phe
```

-continued

```
                325                 330                 335
aat ggg tta gag gct aat gga aca cgg gga cct ggt tta gtt act tgg      1056
Asn Gly Leu Glu Ala Asn Gly Thr Arg Gly Pro Gly Leu Val Thr Trp
            340                 345                 350 ctt agc aaa ata ggt ata tat aat gag tat gtt tcg aga tat ttt gcc      1104
Leu Ser Lys Ile Gly Ile Tyr Asn Glu Tyr Val Ser Arg Tyr Phe Ala
        355                 360                 365 ggc tgg gta gga act cgt cat tat gaa gac tac aca aag ggt aac ggt      1152
Gly Trp Val Gly Thr Arg His Tyr Glu Asp Tyr Thr Lys Gly Asn Gly
    370                 375                 380 att ttt caa cgt atg tct gga act acg agt aat gat cta cgt aat att      1200
Ile Phe Gln Arg Met Ser Gly Thr Thr Ser Asn Asp Leu Arg Asn Ile
385                 390                 395                 400 gat ttt cag aat gcc gat gta tat aaa att act tca tta gct atc atg      1248
Asp Phe Gln Asn Ala Asp Val Tyr Lys Ile Thr Ser Leu Ala Ile Met
                405                 410                 415 aac cta gta gga gag act acc gct aga cca gag tat cgt gtt tca aag      1296
Asn Leu Val Gly Glu Thr Thr Ala Arg Pro Glu Tyr Arg Val Ser Lys
            420                 425                 430 gca gat ttt cgt agg gta ggg gga cct gat tta aat tat gat gca ggt      1344
Ala Asp Phe Arg Arg Val Gly Gly Pro Asp Leu Asn Tyr Asp Ala Gly
        435                 440                 445 aat aat ggg cta agc agg atg aca att gaa tct acg ttc cca ctt gta      1392
Asn Asn Gly Leu Ser Arg Met Thr Ile Glu Ser Thr Phe Pro Leu Val
    450                 455                 460 ttg cac tct aat ggt gtt aga gga ccc tct cat aga tta tca aat gcg      1440
Leu His Ser Asn Gly Val Arg Gly Pro Ser His Arg Leu Ser Asn Ala
465                 470                 475                 480 gca tgt gtt gta tat gga aac tcc aga gtt aac gta tat ggt tgg aca      1488
Ala Cys Val Val Tyr Gly Asn Ser Arg Val Asn Val Tyr Gly Trp Thr
                485                 490                 495 cat aca agt tta aaa cgt gaa aat ata att gaa gcc aat caa att aca      1536
His Thr Ser Leu Lys Arg Glu Asn Ile Ile Glu Ala Asn Gln Ile Thr
            500                 505                 510 caa ata ccg gcg gtg aag agt tat tac ctt caa aat tat ctt gct aat      1584
Gln Ile Pro Ala Val Lys Ser Tyr Tyr Leu Gln Asn Tyr Leu Ala Asn
        515                 520                 525 gcc tat acc tat gta ata aaa ggc act cat aca ggt ggg gat tta atc      1632
Ala Tyr Thr Tyr Val Ile Lys Gly Thr His Thr Gly Gly Asp Leu Ile
    530                 535                 540 cgt ttt tta aga aca aaa tca gag tat aac gca gtt tat gca ggt ggc      1680
Arg Phe Leu Arg Thr Lys Ser Glu Tyr Asn Ala Val Tyr Ala Gly Gly
545                 550                 555                 560 gga att aga ttg att att aat aac aaa act gca gga caa agt tac cgt      1728
Gly Ile Arg Leu Ile Ile Asn Asn Lys Thr Ala Gly Gln Ser Tyr Arg
                565                 570                 575 att cgt ttt cgt tat gct gca gat aaa gct gct ttc ttt agt gta tat      1776
Ile Arg Phe Arg Tyr Ala Ala Asp Lys Ala Ala Phe Phe Ser Val Tyr
            580                 585                 590 ctt tat cca gga ggt tgg ggt tca aat cgt ttt gta tcg ctt gaa aaa      1824
Leu Tyr Pro Gly Gly Trp Gly Ser Asn Arg Phe Val Ser Leu Glu Lys
        595                 600                 605 tct tac tct gga aat tat gac gat tta aaa tat agt gat ttt aaa ttc      1872
Ser Tyr Ser Gly Asn Tyr Asp Asp Leu Lys Tyr Ser Asp Phe Lys Phe
    610                 615                 620 gct gaa att atc aca cct cca tta cct agt tca aac att cag atg gat      1920
Ala Glu Ile Ile Thr Pro Pro Leu Pro Ser Ser Asn Ile Gln Met Asp
625                 630                 635                 640 gtg gag atg caa gcg aat agt ttt caa tca gat gta aac gtg gtt ctc      1968
```

```
                Val Glu Met Gln Ala Asn Ser Phe Gln Ser Asp Val Asn Val Val Leu
                                645                 650                 655 gac aaa att gaa ttc ctc cca agt aat aca aca act tta gaa tat gag           2016
Asp Lys Ile Glu Phe Leu Pro Ser Asn Thr Thr Thr Leu Glu Tyr Glu
            660                 665                 670 gga gaa cgg gac cta gaa aaa aca aag aac gcg gtg aac gat ctg ttt           2064
Gly Glu Arg Asp Leu Glu Lys Thr Lys Asn Ala Val Asn Asp Leu Phe
675                 680                 685 acc aat taa                                                               2073
Thr Asn  *
690

<210> SEQ ID NO 5
<211> LENGTH: 690
<212> TYPE: PRT
<213> ORGANISM: Bacillus thuringiensis

<400> SEQUENCE: 5

Met Ser Pro Tyr Gln Asn Lys Asn Glu Tyr Glu Ile Leu Glu Ser Ser
 1               5                  10                  15

Ser Asn Asn Thr Asn Thr Pro Asn Arg Tyr Pro Phe Ala Asn Asn Arg
            20                  25                  30

Asp Met Ser Thr Met Ser Trp Asn Asp Cys Gln Gly Ile Ser Trp Asp
        35                  40                  45

Glu Ile Trp Glu Ser Val Glu Thr Ile Thr Ser Ile Gly Ile Asn Leu
    50                  55                  60

Ile Glu Phe Val Ile Glu Pro Ser Leu Gly Gly Ile Asn Thr Leu Leu
65                  70                  75                  80

Ser Ile Ile Gly Lys Leu Ile Pro Thr Asn Arg Gln Thr Val Ser Ala
                85                  90                  95

Leu Ser Ile Cys Asp Leu Leu Ser Ile Ile Arg Lys Glu Val Ala Asp
            100                 105                 110

Ser Val Leu Ser Asp Ala Ile Ala Asp Phe Asp Gly Lys Leu Lys Asn
        115                 120                 125

Tyr Arg Glu Tyr Tyr Leu Ser Tyr Leu Gly Ala Trp Leu Lys Asp Gly
    130                 135                 140

Lys Pro Leu Gln Lys Thr Asn Asn Ser Asp Ile Gly Gln Leu Val Tyr
145                 150                 155                 160

Tyr Phe Lys Leu Ser Glu Arg Asp Phe Asn Glu Ile Leu Gly Gly Ser
                165                 170                 175

Leu Ser Arg Asn Asn Ala Gln Val Leu Leu Pro Thr Phe Ala Gln
            180                 185                 190

Ala Ala Asn Val Gln Leu Leu Leu Arg Asp Ala Val Gln Tyr Lys
        195                 200                 205

Ala Gln Trp Phe Pro Phe Leu Ser Ala Glu Asn Val Arg Ser Glu Leu
    210                 215                 220

Ile Ser Pro Asn Ser Gly Cys Asp Phe Thr Gly Asp Tyr Tyr Glu Arg
225                 230                 235                 240

Leu Lys Cys Lys Thr Ala Glu Tyr Thr Asn Tyr Cys Leu Tyr Trp Tyr
                245                 250                 255

Gln Val Gly Leu Asn Gln Ile Lys Gln Gly Gly Thr Gly Ala Asp Thr
            260                 265                 270

Trp Ser Lys Phe Asn Lys Phe Arg Arg Glu Met Thr Leu Ala Val Leu
        275                 280                 285

Asp Ile Ile Ala Ile Phe Pro Thr Tyr Asp Phe Glu Lys Tyr Pro Leu
    290                 295                 300
```

```
Pro Thr His Val Glu Leu Thr Arg Glu Ile Tyr Thr Asp Ala Val Gly
305                 310                 315                 320

Tyr Ser Ser Gly Thr Tyr Ser Trp Leu Arg Asn Trp Pro Asn Thr Phe
            325                 330                 335

Asn Gly Leu Glu Ala Asn Gly Thr Arg Gly Pro Gly Leu Val Thr Trp
            340                 345                 350

Leu Ser Lys Ile Gly Ile Tyr Asn Glu Tyr Val Ser Arg Tyr Phe Ala
            355                 360                 365

Gly Trp Val Gly Thr Arg His Tyr Glu Asp Tyr Thr Lys Gly Asn Gly
    370                 375                 380

Ile Phe Gln Arg Met Ser Gly Thr Thr Ser Asn Asp Leu Arg Asn Ile
385                 390                 395                 400

Asp Phe Gln Asn Ala Asp Val Tyr Lys Ile Thr Ser Leu Ala Ile Met
                405                 410                 415

Asn Leu Val Gly Glu Thr Thr Ala Arg Pro Glu Tyr Arg Val Ser Lys
            420                 425                 430

Ala Asp Phe Arg Arg Val Gly Gly Pro Asp Leu Asn Tyr Asp Ala Gly
            435                 440                 445

Asn Asn Gly Leu Ser Arg Met Thr Ile Glu Ser Thr Phe Pro Leu Val
            450                 455                 460

Leu His Ser Asn Gly Val Arg Gly Pro Ser His Arg Leu Ser Asn Ala
465                 470                 475                 480

Ala Cys Val Val Tyr Gly Asn Ser Arg Val Asn Val Tyr Gly Trp Thr
                485                 490                 495

His Thr Ser Leu Lys Arg Glu Asn Ile Ile Glu Ala Asn Gln Ile Thr
            500                 505                 510

Gln Ile Pro Ala Val Lys Ser Tyr Tyr Leu Gln Asn Tyr Leu Ala Asn
            515                 520                 525

Ala Tyr Thr Tyr Val Ile Lys Gly Thr His Thr Gly Gly Asp Leu Ile
            530                 535                 540

Arg Phe Leu Arg Thr Lys Ser Glu Tyr Asn Ala Val Tyr Ala Gly Gly
545                 550                 555                 560

Gly Ile Arg Leu Ile Ile Asn Asn Lys Thr Ala Gly Gln Ser Tyr Arg
            565                 570                 575

Ile Arg Phe Arg Tyr Ala Ala Asp Lys Ala Ala Phe Phe Ser Val Tyr
            580                 585                 590

Leu Tyr Pro Gly Gly Trp Gly Ser Asn Arg Phe Val Ser Leu Glu Lys
            595                 600                 605

Ser Tyr Ser Gly Asn Tyr Asp Asp Leu Lys Tyr Ser Asp Phe Lys Phe
610                 615                 620

Ala Glu Ile Ile Thr Pro Pro Leu Pro Ser Ser Asn Ile Gln Met Asp
625                 630                 635                 640

Val Glu Met Gln Ala Asn Ser Phe Gln Ser Asp Val Asn Val Val Leu
                645                 650                 655

Asp Lys Ile Glu Phe Leu Pro Ser Asn Thr Thr Thr Leu Glu Tyr Glu
            660                 665                 670

Gly Glu Arg Asp Leu Glu Lys Thr Lys Asn Ala Val Asn Asp Leu Phe
            675                 680                 685

Thr Asn
    690

<210> SEQ ID NO 6
<211> LENGTH: 1686
```

```
<212> TYPE: DNA
<213> ORGANISM: Bacillus thuringiensis
<220> FEATURE:
<221> NAME/KEY: CDS
<222> LOCATION: (1)...(1686)

<400> SEQUENCE: 6 gtg agt cct atg ttt aca agt agt acg aaa aat acg tta aaa ata gaa        48
Met Ser Pro Met Phe Thr Ser Ser Thr Lys Asn Thr Leu Lys Ile Glu
 1               5                  10                  15 acg aca gat tat gaa ata gat caa gcg gcc att tct ata gaa tgt atg        96
Thr Thr Asp Tyr Glu Ile Asp Gln Ala Ala Ile Ser Ile Glu Cys Met
             20                  25                  30 tca gat gaa caa aat cct cag gaa aaa ata atg tta tgg gat gaa ata       144
Ser Asp Glu Gln Asn Pro Gln Glu Lys Ile Met Leu Trp Asp Glu Ile
         35                  40                  45 aaa ctg gca aaa caa ctt agt cag tct cgt aat cta ctc caa aat gga       192
Lys Leu Ala Lys Gln Leu Ser Gln Ser Arg Asn Leu Leu Gln Asn Gly
     50                  55                  60 gac ttt tct ggg aat gat tgg aca ttc ggt aat gat att atc ata gga       240
Asp Phe Ser Gly Asn Asp Trp Thr Phe Gly Asn Asp Ile Ile Ile Gly
 65                  70                  75                  80 tcc aat aat cct att ttt aaa gga aaa ttt cta cag atg cgt gga gca       288
Ser Asn Asn Pro Ile Phe Lys Gly Lys Phe Leu Gln Met Arg Gly Ala
                 85                  90                  95 cga gac ata tat gga act cta ttt cca acc tat atc tgt caa aaa ata       336
Arg Asp Ile Tyr Gly Thr Leu Phe Pro Thr Tyr Ile Cys Gln Lys Ile
            100                 105                 110 gat gag tct aaa tta aaa cca tat aca cgt tat cga gta aga ggg ttt       384
Asp Glu Ser Lys Leu Lys Pro Tyr Thr Arg Tyr Arg Val Arg Gly Phe
        115                 120                 125 gtg gga agt agt aaa gat ttg aaa tta atg gta aca cgt tac ggg aaa       432
Val Gly Ser Ser Lys Asp Leu Lys Leu Met Val Thr Arg Tyr Gly Lys
    130                 135                 140 gaa att gat gct atc atg aat gtt cca aat gat ttg gcc tat atg cag       480
Glu Ile Asp Ala Ile Met Asn Val Pro Asn Asp Leu Ala Tyr Met Gln
145                 150                 155                 160 cct aat cct tca tgt gga gat tat cgc tgt gaa tca tcg tct cag tat       528
Pro Asn Pro Ser Cys Gly Asp Tyr Arg Cys Glu Ser Ser Ser Gln Tyr
                165                 170                 175 gtg agc caa ggg tat cct aca cca aca gat gga tat gct ccc gat atg       576
Val Ser Gln Gly Tyr Pro Thr Pro Thr Asp Gly Tyr Ala Pro Asp Met
            180                 185                 190 tat gca tgc ccg caa aat ata gat aga aag cat gtg aag tgt cac gat       624
Tyr Ala Cys Pro Gln Asn Ile Asp Arg Lys His Val Lys Cys His Asp
        195                 200                 205 cgt cat cca ttt gat ttt cat att gac acc gga gaa gta gat aca aat       672
Arg His Pro Phe Asp Phe His Ile Asp Thr Gly Glu Val Asp Thr Asn
    210                 215                 220 aca aat gta ggt att gat gtc tta tta aaa att tct aat cca gat gga       720
Thr Asn Val Gly Ile Asp Val Leu Leu Lys Ile Ser Asn Pro Asp Gly
225                 230                 235                 240 tac gct aca gta ggg aat cta gaa gtc att gaa gaa gga cca cta aca       768
Tyr Ala Thr Val Gly Asn Leu Glu Val Ile Glu Glu Gly Pro Leu Thr
                245                 250                 255 ggt gaa gca ttg gca cat gtg aaa caa aag gaa aag aaa tgg aaa caa       816
Gly Glu Ala Leu Ala His Val Lys Gln Lys Glu Lys Lys Trp Lys Gln
            260                 265                 270 cac atg gag aaa aaa cgt tgg gaa aca caa caa gcc tat gat cca gca       864
His Met Glu Lys Lys Arg Trp Glu Thr Gln Gln Ala Tyr Asp Pro Ala
        275                 280                 285
```

```
aaa cag gct gta gat gca tta ttt aca aat gaa caa gag tta cac tat      912
Lys Gln Ala Val Asp Ala Leu Phe Thr Asn Glu Gln Glu Leu His Tyr
    290                 295                 300 cat att act tta gat cat att caa aac gct gat cga ctg gta cag tcg      960
His Ile Thr Leu Asp His Ile Gln Asn Ala Asp Arg Leu Val Gln Ser
305                 310                 315                 320 att ccc tat gta tac cat aat tgg tta ccg aat gct cca ggt atg aac     1008
Ile Pro Tyr Val Tyr His Asn Trp Leu Pro Asn Ala Pro Gly Met Asn
                325                 330                 335 tat gat gta tat caa gag tta aac gca cgt atc atg caa ggt tat aat     1056
Tyr Asp Val Tyr Gln Glu Leu Asn Ala Arg Ile Met Gln Gly Tyr Asn
            340                 345                 350 tta tat gat gca cga aat gtc ata aca aat ggt gac ttt aca caa gga     1104
Leu Tyr Asp Ala Arg Asn Val Ile Thr Asn Gly Asp Phe Thr Gln Gly
        355                 360                 365 tta cag gga tgg cac gca aca gga aat gcc gcg gta caa caa atg gat     1152
Leu Gln Gly Trp His Ala Thr Gly Asn Ala Ala Val Gln Gln Met Asp
    370                 375                 380 gga gct tca gta tta gtt cta tca aat tgg agc gcg ggg gta tct caa     1200
Gly Ala Ser Val Leu Val Leu Ser Asn Trp Ser Ala Gly Val Ser Gln
385                 390                 395                 400 aac ttg cat gct caa gat cat cat gga tat gtg tta cgt gtg att gcc     1248
Asn Leu His Ala Gln Asp His His Gly Tyr Val Leu Arg Val Ile Ala
                405                 410                 415 aaa aaa gaa gga cct gga aaa ggg tat gta acg atg atg gat tgt aat     1296
Lys Lys Glu Gly Pro Gly Lys Gly Tyr Val Thr Met Met Asp Cys Asn
            420                 425                 430 gga aag cag gaa aca ctt aag ttc act tct tgc gaa gaa gga tat atg     1344
Gly Lys Gln Glu Thr Leu Lys Phe Thr Ser Cys Glu Glu Gly Tyr Met
        435                 440                 445 aca aaa aca gta gag gta ttc cca gaa agt gat cgt gta cgg att gaa     1392
Thr Lys Thr Val Glu Val Phe Pro Glu Ser Asp Arg Val Arg Ile Glu
    450                 455                 460 ata gga gaa acc gaa ggt aca ttt tat ata gat agc atc gag ttg ctt     1440
Ile Gly Glu Thr Glu Gly Thr Phe Tyr Ile Asp Ser Ile Glu Leu Leu
465                 470                 475                 480 tgt atg caa gga tat gat aac aat aat aac ctg cac acg ggt aat atg     1488
Cys Met Gln Gly Tyr Asp Asn Asn Asn Asn Leu His Thr Gly Asn Met
                485                 490                 495 tat gag caa agt tat aat gga aat tat aat caa aat act agc gat gtg     1536
Tyr Glu Gln Ser Tyr Asn Gly Asn Tyr Asn Gln Asn Thr Ser Asp Val
            500                 505                 510 tat tac caa ggg tat aca aac aac tat aac caa gac tct agt aat atg     1584
Tyr Tyr Gln Gly Tyr Thr Asn Asn Tyr Asn Gln Asp Ser Ser Asn Met
        515                 520                 525 tat aat caa aat tat act aac aat gat gac ctg cat tcc ggt tgc aca     1632
Tyr Asn Gln Asn Tyr Thr Asn Asn Asp Asp Leu His Ser Gly Cys Thr
    530                 535                 540 tgt aac caa ggg cat aac tct ggc tgt aca tgt aat caa gga tat aac     1680
Cys Asn Gln Gly His Asn Ser Gly Cys Thr Cys Asn Gln Gly Tyr Asn
545                 550                 555                 560 cgt taa                                                              1686
Arg *

<210> SEQ ID NO 7
<211> LENGTH: 561
<212> TYPE: PRT
<213> ORGANISM: Bacillus thuringiensis

<400> SEQUENCE: 7
```

```
Met Ser Pro Met Phe Thr Ser Ser Thr Lys Asn Thr Leu Lys Ile Glu
 1               5                  10                  15

Thr Thr Asp Tyr Glu Ile Asp Gln Ala Ala Ile Ser Ile Glu Cys Met
             20                  25                  30

Ser Asp Glu Gln Asn Pro Gln Glu Lys Ile Met Leu Trp Asp Glu Ile
         35                  40                  45

Lys Leu Ala Lys Gln Leu Ser Gln Ser Arg Asn Leu Leu Gln Asn Gly
     50                  55                  60

Asp Phe Ser Gly Asn Asp Trp Thr Phe Gly Asn Asp Ile Ile Ile Gly
 65                  70                  75                  80

Ser Asn Asn Pro Ile Phe Lys Gly Lys Phe Leu Gln Met Arg Gly Ala
                 85                  90                  95

Arg Asp Ile Tyr Gly Thr Leu Phe Pro Thr Tyr Ile Cys Gln Lys Ile
             100                 105                 110

Asp Glu Ser Lys Leu Lys Pro Tyr Thr Arg Tyr Arg Val Arg Gly Phe
         115                 120                 125

Val Gly Ser Ser Lys Asp Leu Lys Leu Met Val Thr Arg Tyr Gly Lys
    130                 135                 140

Glu Ile Asp Ala Ile Met Asn Val Pro Asn Asp Leu Ala Tyr Met Gln
145                 150                 155                 160

Pro Asn Pro Ser Cys Gly Asp Tyr Arg Cys Glu Ser Ser Gln Tyr
                165                 170                 175

Val Ser Gln Gly Tyr Pro Thr Pro Thr Asp Gly Tyr Ala Pro Asp Met
            180                 185                 190

Tyr Ala Cys Pro Gln Asn Ile Asp Arg Lys His Val Lys Cys His Asp
        195                 200                 205

Arg His Pro Phe Asp Phe His Ile Asp Thr Gly Glu Val Asp Thr Asn
    210                 215                 220

Thr Asn Val Gly Ile Asp Val Leu Leu Lys Ile Ser Asn Pro Asp Gly
225                 230                 235                 240

Tyr Ala Thr Val Gly Asn Leu Glu Val Ile Glu Glu Gly Pro Leu Thr
                245                 250                 255

Gly Glu Ala Leu Ala His Val Lys Gln Lys Glu Lys Lys Trp Lys Gln
            260                 265                 270

His Met Glu Lys Lys Arg Trp Glu Thr Gln Gln Ala Tyr Asp Pro Ala
        275                 280                 285

Lys Gln Ala Val Asp Ala Leu Phe Thr Asn Glu Gln Glu Leu His Tyr
    290                 295                 300

His Ile Thr Leu Asp His Ile Gln Asn Ala Asp Arg Leu Val Gln Ser
305                 310                 315                 320

Ile Pro Tyr Val Tyr His Asn Trp Leu Pro Asn Ala Pro Gly Met Asn
                325                 330                 335

Tyr Asp Val Tyr Gln Glu Leu Asn Ala Arg Ile Met Gln Gly Tyr Asn
            340                 345                 350

Leu Tyr Asp Ala Arg Asn Val Ile Thr Asn Gly Asp Phe Thr Gln Gly
        355                 360                 365

Leu Gln Gly Trp His Ala Thr Gly Asn Ala Ala Val Gln Gln Met Asp
    370                 375                 380

Gly Ala Ser Val Leu Val Leu Ser Asn Trp Ser Ala Gly Val Ser Gln
385                 390                 395                 400

Asn Leu His Ala Gln Asp His His Gly Tyr Val Leu Arg Val Ile Ala
                405                 410                 415
```

-continued

```
Lys Lys Glu Gly Pro Gly Lys Gly Tyr Val Thr Met Met Asp Cys Asn
            420                 425                 430
Gly Lys Gln Glu Thr Leu Lys Phe Thr Ser Cys Glu Gly Tyr Met
        435                 440                 445
Thr Lys Thr Val Glu Val Phe Pro Glu Ser Asp Arg Val Arg Ile Glu
    450                 455                 460
Ile Gly Glu Thr Glu Gly Thr Phe Tyr Ile Asp Ser Ile Glu Leu Leu
465                 470                 475                 480
Cys Met Gln Gly Tyr Asp Asn Asn Asn Leu His Thr Gly Asn Met
                485                 490                 495
Tyr Glu Gln Ser Tyr Asn Gly Asn Tyr Asn Gln Asn Thr Ser Asp Val
                500                 505                 510
Tyr Tyr Gln Gly Tyr Thr Asn Asn Tyr Asn Gln Asp Ser Ser Asn Met
            515                 520                 525
Tyr Asn Gln Asn Tyr Thr Asn Asn Asp Asp Leu His Ser Gly Cys Thr
        530                 535                 540
Cys Asn Gln Gly His Asn Ser Gly Cys Thr Cys Asn Gln Gly Tyr Asn
545                 550                 555                 560
Arg

<210> SEQ ID NO 8
<211> LENGTH: 1176
<212> TYPE: PRT
<213> ORGANISM: Bacillus thuringiensis

<400> SEQUENCE: 8

Met Asp Asn Asn Pro Asn Ile Asn Glu Cys Ile Pro Tyr Asn Cys Leu
 1               5                  10                  15
Ser Asn Pro Glu Val Glu Val Leu Gly Gly Glu Arg Ile Glu Thr Gly
                20                  25                  30
Tyr Thr Pro Ile Asp Ile Ser Leu Ser Leu Thr Gln Phe Leu Leu Ser
            35                  40                  45
Glu Phe Val Pro Gly Ala Gly Phe Val Leu Gly Leu Val Asp Ile Ile
    50                  55                  60
Trp Gly Ile Phe Gly Pro Ser Gln Trp Asp Ala Phe Pro Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
                100                 105                 110
Ser Phe Arg Glu Trp Glu Ala Asp Pro Thr Asn Pro Ala Leu Arg Glu
            115                 120                 125
Glu Met Arg Ile Gln Phe Asn Asp Met Asn Ser Ala Leu Thr Thr Ala
    130                 135                 140
Ile Pro Leu Leu Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
                180                 185                 190
Tyr Asn Asp Leu Thr Arg Leu Ile Gly Asn Tyr Thr Asp Tyr Ala Val
            195                 200                 205
Arg Trp Tyr Asn Thr Gly Leu Glu Arg Val Trp Gly Pro Asp Ser Arg
    210                 215                 220
```

-continued

```
Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
```

-continued

```
                645                 650                 655
Glu Phe Cys Leu Asp Glu Lys Gln Glu Leu Ser Glu Lys Val Lys His
            660                 665                 670
Ala Lys Arg Leu Ser Asp Glu Arg Asn Leu Leu Gln Asp Pro Asn Phe
            675                 680                 685
Arg Gly Ile Asn Arg Gln Leu Asp Arg Gly Trp Arg Gly Ser Thr Asp
            690                 695                 700
Ile Thr Ile Gln Gly Gly Asp Asp Val Phe Lys Glu Asn Tyr Val Thr
705                 710                 715                 720
Leu Leu Gly Thr Phe Asp Glu Cys Tyr Pro Thr Tyr Leu Tyr Gln Lys
            725                 730                 735
Ile Asp Glu Ser Lys Leu Lys Ala Tyr Thr Arg Tyr Gln Leu Arg Gly
            740                 745                 750
Tyr Ile Glu Asp Ser Gln Asp Leu Glu Ile Tyr Leu Ile Arg Tyr Asn
            755                 760                 765
Ala Lys His Glu Thr Val Asn Val Pro Gly Thr Gly Ser Leu Trp Pro
            770                 775                 780
Leu Ser Ala Gln Ser Pro Ile Gly Lys Cys Gly Glu Pro Asn Arg Cys
785                 790                 795                 800
Ala Pro His Leu Glu Trp Asn Pro Asp Leu Asp Cys Ser Cys Arg Asp
            805                 810                 815
Gly Glu Lys Cys Ala His His Ser His His Phe Ser Leu Asp Ile Asp
            820                 825                 830
Val Gly Cys Thr Asp Leu Asn Glu Asp Leu Gly Val Trp Val Ile Phe
            835                 840                 845
Lys Ile Lys Thr Gln Asp Gly His Ala Arg Leu Gly Asn Leu Glu Phe
            850                 855                 860
Leu Glu Glu Lys Pro Leu Val Gly Glu Ala Leu Ala Arg Val Lys Arg
865                 870                 875                 880
Ala Glu Lys Lys Trp Arg Asp Lys Arg Glu Lys Leu Glu Trp Glu Thr
            885                 890                 895
Asn Ile Val Tyr Lys Glu Ala Lys Glu Ser Val Asp Ala Leu Phe Val
            900                 905                 910
Asn Ser Gln Tyr Asp Gln Leu Gln Ala Asp Thr Asn Ile Ala Met Ile
            915                 920                 925
His Ala Ala Asp Lys Arg Val His Ser Ile Arg Glu Ala Tyr Leu Pro
            930                 935                 940
Glu Leu Ser Val Ile Pro Gly Val Asn Ala Ala Ile Phe Glu Glu Leu
945                 950                 955                 960
Glu Gly Arg Ile Phe Thr Ala Phe Ser Leu Tyr Asp Ala Arg Asn Val
            965                 970                 975
Ile Lys Asn Gly Asp Phe Asn Asn Gly Leu Ser Cys Trp Asn Val Lys
            980                 985                 990
Gly His Val Asp Val Glu Glu Gln Asn Asn Gln Arg Ser Val Leu Val
            995                 1000                1005
Val Pro Glu Trp Glu Ala Glu Val Ser Gln Glu Val Arg Val Cys Pro
            1010                1015                1020
Gly Arg Gly Tyr Ile Leu Arg Val Thr Ala Tyr Lys Glu Gly Tyr Gly
1025                1030                1035                1040
Glu Gly Cys Val Thr Ile His Glu Ile Glu Asn Asn Thr Asp Glu Leu
            1045                1050                1055
Lys Phe Ser Asn Cys Val Glu Glu Glu Ile Tyr Pro Asn Asn Thr Val
            1060                1065                1070
```

-continued

Thr Cys Asn Asp Tyr Thr Val Asn Gln Glu Glu Tyr Gly Gly Ala Tyr
1075 1080 1085

Thr Ser Arg Asn Arg Gly Tyr Asn Glu Ala Pro Ser Val Pro Ala Asp
1090 1095 1100

Tyr Ala Ser Val Tyr Glu Glu Lys Ser Tyr Thr Asp Gly Arg Arg Glu
1105 1110 1115 1120

Asn Pro Cys Glu Phe Asn Arg Gly Tyr Arg Asp Tyr Thr Pro Leu Pro
1125 1130 1135

Val Gly Tyr Val Thr Lys Glu Leu Glu Tyr Phe Pro Glu Thr Asp Lys
1140 1145 1150

Val Trp Ile Glu Ile Gly Glu Thr Glu Gly Thr Phe Ile Val Asp Ser
1155 1160 1165

Val Glu Leu Leu Leu Met Glu Glu
1170 1175

<210> SEQ ID NO 9
<211> LENGTH: 1178
<212> TYPE: PRT
<213> ORGANISM: Bacillus thuringiensis

<400> SEQUENCE: 9

Met Asp Asn Asn Pro Asn Ile Asn Glu Cys Ile Pro Tyr Asn Cys Leu
1 5 10 15

Ser Asn Pro Glu Val Glu Val Leu Gly Gly Glu Arg Ile Glu Thr Gly
20 25 30

Tyr Thr Pro Ile Asp Ile Ser Leu Ser Leu Thr Gln Phe Leu Leu Ser
35 40 45

Glu Phe Val Pro Gly Ala Gly Phe Val Leu Gly Leu Val Asp Ile Ile
50 55 60

Trp Gly Ile Phe Gly Pro Ser Gln Trp Asp Ala Phe Leu Val Gln Ile
65 70 75 80

Glu Gln Leu Ile Asn Gln Arg Ile Glu Glu Phe Ala Arg Asn Gln Ala
85 90 95

Ile Ser Arg Leu Glu Gly Leu Ser Asn Leu Tyr Gln Ile Tyr Ala Glu
100 105 110

Ser Phe Arg Glu Trp Glu Ala Asp Pro Thr Asn Pro Ala Leu Arg Glu
115 120 125

Glu Met Arg Ile Gln Phe Asn Asp Met Asn Ser Ala Leu Thr Thr Ala
130 135 140

Ile Pro Leu Phe Ala Val Gln Asn Tyr Gln Val Pro Leu Leu Ser Val
145 150 155 160

Tyr Val Gln Ala Ala Asn Leu His Leu Ser Val Leu Arg Asp Val Ser
165 170 175

Val Phe Gly Gln Arg Trp Gly Phe Asp Ala Ala Thr Ile Asn Ser Arg
180 185 190

Tyr Asn Asp Leu Thr Arg Leu Ile Gly Asn Tyr Thr Asp Tyr Ala Val
195 200 205

Arg Trp Tyr Asn Thr Gly Leu Glu Arg Val Trp Gly Pro Asp Ser Arg
210 215 220

Asp Trp Val Arg Tyr Asn Gln Phe Arg Arg Glu Leu Thr Leu Thr Val
225 230 235 240

Leu Asp Ile Val Ala Leu Phe Pro Asn Tyr Asp Ser Arg Arg Tyr Pro
245 250 255

Ile Arg Thr Val Ser Gln Leu Thr Arg Glu Ile Tyr Thr Asn Pro Val

```
                260                 265                 270
Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
        290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685
```

-continued

```
Asn Phe Lys Asp Ile Asn Arg Gln Pro Glu Arg Gly Trp Gly Gly Ser
    690                 695                 700
Thr Gly Ile Thr Ile Gln Gly Gly Asp Val Phe Lys Glu Asn Tyr
705                 710                 715                 720
Val Thr Leu Ser Gly Thr Phe Asp Glu Cys Tyr Pro Thr Tyr Leu Tyr
                725                 730                 735
Gln Lys Ile Asp Glu Ser Lys Leu Lys Ala Phe Thr Arg Tyr Gln Leu
            740                 745                 750
Arg Gly Tyr Ile Glu Asp Ser Gln Asp Leu Glu Ile Tyr Leu Ile Arg
                755                 760                 765
Tyr Asn Ala Lys His Glu Thr Val Asn Val Pro Gly Thr Gly Ser Leu
    770                 775                 780
Trp Pro Leu Ser Ala Gln Ser Pro Ile Gly Lys Cys Gly Glu Pro Asn
785                 790                 795                 800
Arg Cys Ala Pro His Leu Glu Trp Asn Pro Asp Leu Asp Cys Ser Cys
                805                 810                 815
Arg Asp Gly Glu Lys Cys Ala His His Ser His His Phe Ser Leu Asp
            820                 825                 830
Ile Asp Val Gly Cys Thr Asp Leu Asn Glu Asp Leu Gly Val Trp Val
        835                 840                 845
Ile Phe Lys Ile Lys Thr Gln Asp Gly His Ala Arg Leu Gly Asn Leu
    850                 855                 860
Glu Phe Leu Glu Glu Lys Pro Leu Val Gly Glu Ala Leu Ala Arg Val
865                 870                 875                 880
Lys Arg Ala Glu Lys Lys Trp Arg Asp Lys Arg Glu Lys Leu Glu Trp
                885                 890                 895
Glu Thr Asn Ile Val Tyr Lys Glu Ala Lys Glu Ser Val Asp Ala Leu
            900                 905                 910
Phe Val Asn Ser Gln Tyr Asp Gln Leu Gln Ala Asp Thr Asn Ile Ala
        915                 920                 925
Met Ile His Ala Ala Asp Lys Arg Val His Ser Ile Arg Glu Ala Tyr
    930                 935                 940
Leu Pro Glu Leu Ser Val Ile Pro Gly Val Asn Ala Ala Ile Phe Glu
945                 950                 955                 960
Glu Leu Glu Gly Arg Ile Phe Thr Ala Phe Ser Leu Tyr Asp Ala Arg
                965                 970                 975
Asn Val Ile Lys Asn Gly Asp Phe Asn Asn Gly Leu Ser Cys Trp Asn
            980                 985                 990
Val Lys Gly His Val Asp Val Glu Glu Gln Asn Asn Gln Arg Ser Val
        995                 1000                1005
Leu Val Val Pro Glu Trp Glu Ala Glu Val Ser Gln Glu Val Arg Val
    1010                1015                1020
Cys Pro Gly Arg Gly Tyr Ile Leu Arg Val Thr Ala Tyr Lys Glu Gly
1025                1030                1035                1040
Tyr Gly Glu Gly Cys Val Thr Ile His Glu Ile Glu Asn Asn Thr Asp
                1045                1050                1055
Glu Leu Lys Phe Ser Asn Cys Val Glu Glu Glu Ile Tyr Pro Asn Asn
            1060                1065                1070
Thr Val Thr Cys Asn Asp Tyr Thr Val Asn Gln Glu Glu Tyr Gly Gly
        1075                1080                1085
Ala Tyr Thr Ser Arg Asn Arg Gly Tyr Asn Glu Ala Pro Ser Val Pro
    1090                1095                1100
```

```
Ala Asp Tyr Ala Ser Val Tyr Glu Glu Lys Ser Tyr Thr Asp Gly Arg
1105                1110                1115                1120

Arg Glu Asn Pro Cys Glu Phe Asn Arg Gly Tyr Arg Asp Tyr Thr Pro
            1125                1130                1135

Leu Pro Val Gly Tyr Val Thr Lys Glu Leu Glu Tyr Phe Pro Glu Thr
        1140                1145                1150

Asp Lys Val Trp Ile Glu Ile Gly Thr Glu Gly Thr Phe Ile Val
    1155                1160                1165

Asp Ser Val Glu Leu Leu Met Glu Glu
    1170                1175

<210> SEQ ID NO 10
<211> LENGTH: 719
<212> TYPE: PRT
<213> ORGANISM: Bacillus thuringiensis

<400> SEQUENCE: 10

Met Lys Leu Lys Asn Gln Asp Lys His Gln Ser Phe Ser Ser Asn Ala
 1               5                  10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125

Lys Gly Leu Gly Asp Ala Leu Ala Val Tyr His Asp Ser Leu Glu Ser
    130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205

Glu Trp Gly Leu Ser Ser Ser Glu Ile Ser Thr Phe Tyr Asn Arg Gln
    210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
    290                 295                 300
```

```
Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
            325                 330                 335

Asp Phe Leu Glu Gln Val Thr Ile Tyr Ser Leu Leu Ser Arg Trp Ser
        340                 345                 350

Asn Thr Gln Tyr Met Asn Met Trp Gly Gly His Lys Leu Glu Phe Arg
    355                 360                 365

Thr Ile Gly Gly Thr Leu Asn Ile Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
            405                 410                 415

Gly Val Pro Arg Val Asp Phe His Trp Lys Phe Val Thr His Pro Ile
        420                 425                 430

Ala Ser Asp Asn Phe Tyr Tyr Pro Gly Tyr Ala Gly Ile Gly Thr Gln
    435                 440                 445

Leu Gln Asp Ser Glu Asn Glu Leu Pro Pro Glu Ala Thr Gly Gln Pro
450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
            485                 490                 495

Asp Arg Thr Asn Thr Ile Glu Pro Asn Ser Ile Thr Gln Ile Pro Leu
        500                 505                 510

Val Lys Ala Phe Asn Leu Ser Ser Gly Ala Ala Val Val Arg Gly Pro
    515                 520                 525

Gly Phe Thr Gly Gly Asp Ile Leu Arg Arg Thr Asn Thr Gly Thr Phe
530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
            565                 570                 575

Ile Asn Gly Lys Ala Ile Asn Gln Gly Asn Phe Ser Ala Thr Met Asn
        580                 585                 590

Arg Gly Glu Asp Leu Asp Tyr Lys Thr Phe Arg Thr Val Gly Phe Thr
    595                 600                 605

Thr Pro Phe Ser Phe Leu Asp Val Gln Ser Thr Phe Thr Ile Gly Ala
610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
            645                 650                 655

Gln Glu Lys Val Thr Ala Leu Phe Thr Ser Thr Asn Pro Arg Gly Leu
        660                 665                 670

Lys Thr Asp Val Lys Asp Tyr His Ile Asp Gln Val Ser Asn Leu Val
    675                 680                 685

Glu Ser Leu Ser Asp Glu Phe Tyr Leu Asp Glu Lys Arg Glu Leu Phe
690                 695                 700

Glu Ile Val Lys Tyr Ala Lys Gln Leu His Ile Glu Arg Asn Met
705                 710                 715
```

<210> SEQ ID NO 11
<211> LENGTH: 633
<212> TYPE: PRT
<213> ORGANISM: Bacillus thuringiensis

<400> SEQUENCE: 11

Met Asn Asn Val Leu Asn Ser Gly Arg Thr Thr Ile Cys Asp Ala Tyr
1               5                   10                  15

Asn Val Val Ala His Asp Pro Phe Ser Phe Glu His Lys Ser Leu Asp
            20                  25                  30

Thr Ile Gln Lys Glu Trp Met Glu Trp Lys Arg Thr Asp His Ser Leu
        35                  40                  45

Tyr Val Ala Pro Val Val Gly Thr Val Ser Ser Phe Leu Leu Lys Lys
    50                  55                  60

Val Gly Ser Leu Ile Gly Lys Arg Ile Leu Ser Glu Leu Trp Gly Ile
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Ala Arg
            100                 105                 110

Val Asn Ala Glu Leu Ile Gly Leu Gln Ala Asn Ile Arg Glu Phe Asn
        115                 120                 125

Gln Gln Val Asp Asn Phe Leu Asn Pro Thr Gln Asn Pro Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Pro Leu
                165                 170                 175

Phe Ala Gln Ala Ala Asn Met His Leu Ser Phe Ile Arg Asp Val Ile
            180                 185                 190

Leu Asn Ala Asp Glu Trp Gly Ile Ser Ala Ala Thr Leu Arg Thr Tyr
        195                 200                 205

Arg Asp Tyr Leu Arg Asn Tyr Thr Arg Asp Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Met Val Ser Ser Gly
            260                 265                 270

Ala Asn Leu Tyr Ala Ser Gly Ser Gly Pro Gln Gln Thr Gln Ser Phe
        275                 280                 285

Thr Ala Gln Asn Trp Pro Phe Leu Tyr Ser Leu Phe Gln Val Asn Ser
    290                 295                 300

Asn Tyr Ile Leu Ser Gly Ile Ser Gly Thr Arg Leu Ser Ile Thr Phe
305                 310                 315                 320

Pro Asn Ile Gly Gly Leu Pro Gly Ser Thr Thr Thr His Ser Leu Asn
                325                 330                 335

Ser Ala Arg Val Asn Tyr Ser Gly Gly Val Ser Ser Gly Leu Ile Gly
            340                 345                 350

Ala Thr Asn Leu Asn His Asn Phe Asn Cys Ser Thr Val Leu Pro Pro
        355                 360                 365

Leu Ser Thr Pro Phe Val Arg Ser Trp Leu Asp Ser Gly Thr Asp Arg
    370                 375                 380

Glu Gly Val Ala Thr Ser Thr Asn Trp Gln Thr Glu Ser Phe Gln Thr
385                 390                 395                 400

Thr Leu Ser Leu Arg Cys Gly Ala Phe Ser Ala Arg Gly Asn Ser Asn
            405                 410                 415

Tyr Phe Pro Asp Tyr Phe Ile Arg Asn Ile Ser Gly Val Pro Leu Val
            420                 425                 430

Ile Arg Asn Glu Asp Leu Thr Arg Pro Leu His Tyr Asn Gln Ile Arg
            435                 440                 445

Asn Ile Glu Ser Pro Ser Gly Thr Pro Gly Gly Ala Arg Ala Tyr Leu
            450                 455                 460

Val Ser Val His Asn Arg Lys Asn Asn Ile Tyr Ala Ala Asn Glu Asn
465                 470                 475                 480

Gly Thr Met Ile His Leu Ala Pro Glu Asp Tyr Thr Gly Phe Thr Ile
            485                 490                 495

Ser Pro Ile His Ala Thr Gln Val Asn Asn Gln Thr Arg Thr Phe Ile
            500                 505                 510

Ser Glu Lys Phe Gly Asn Gln Gly Asp Ser Leu Arg Phe Glu Gln Ser
            515                 520                 525

Asn Thr Thr Ala Arg Tyr Thr Leu Arg Gly Asn Gly Asn Ser Tyr Asn
            530                 535                 540

Leu Tyr Leu Arg Val Ser Ser Ile Gly Asn Ser Thr Ile Arg Val Thr
545                 550                 555                 560

Ile Asn Gly Arg Val Tyr Thr Val Ser Asn Val Asn Thr Thr Thr Asn
            565                 570                 575

Asn Asp Gly Val Asn Asp Asn Gly Ala Arg Phe Ser Asp Ile Asn Ile
            580                 585                 590

Gly Asn Ile Val Ala Ser Asp Asn Thr Asn Val Thr Leu Asp Ile Asn
            595                 600                 605

Val Thr Leu Asn Ser Gly Thr Pro Phe Asp Leu Met Asn Ile Met Phe
            610                 615                 620

Val Pro Thr Asn Leu Pro Pro Leu Tyr
625                 630

<210> SEQ ID NO 12
<211> LENGTH: 652
<212> TYPE: PRT
<213> ORGANISM: Bacillus thuringiensis

<400> SEQUENCE: 12

Met Ile Arg Lys Gly Gly Arg Lys Met Asn Pro Asn Asn Arg Ser Glu
1               5                   10                  15

His Asp Thr Ile Lys Thr Thr Glu Asn Asn Glu Val Pro Thr Asn His
            20                  25                  30

Val Gln Tyr Pro Leu Ala Glu Thr Pro Asn Pro Thr Leu Glu Asp Leu
            35                  40                  45

Asn Tyr Lys Glu Phe Leu Arg Met Thr Ala Asp Asn Asn Thr Glu Ala
        50                  55                  60

Leu Asp Ser Ser Thr Thr Lys Asp Val Ile Gln Lys Gly Ile Ser Val
65                  70                  75                  80

Val Gly Asp Leu Leu Gly Val Val Gly Phe Pro Phe Gly Gly Ala Leu
                85                  90                  95

Val Ser Phe Tyr Thr Asn Phe Leu Asn Thr Ile Trp Pro Ser Glu Asp
            100                 105                 110

Pro Trp Lys Ala Phe Met Glu Gln Val Glu Ala Leu Met Asp Gln Lys

```
                115                 120                 125
Ile Ala Asp Tyr Ala Lys Asn Lys Ala Leu Ala Glu Leu Gln Gly Leu
    130                 135                 140

Gln Asn Asn Val Glu Asp Tyr Val Ser Ala Leu Ser Ser Trp Gln Lys
145                 150                 155                 160

Asn Pro Val Ser Ser Arg Asn Pro His Ser Gln Gly Arg Ile Arg Glu
                165                 170                 175

Leu Phe Ser Gln Ala Glu Ser His Phe Arg Asn Ser Met Pro Ser Phe
            180                 185                 190

Ala Ile Ser Gly Tyr Glu Val Leu Phe Leu Thr Thr Tyr Ala Gln Ala
        195                 200                 205

Ala Asn Thr His Leu Phe Leu Leu Lys Asp Ala Gln Ile Tyr Gly Glu
    210                 215                 220

Glu Trp Gly Tyr Glu Lys Glu Asp Ile Ala Glu Phe Tyr Lys Arg Gln
225                 230                 235                 240

Leu Lys Leu Thr Gln Glu Tyr Thr Asp His Cys Val Lys Trp Tyr Asn
                245                 250                 255

Val Gly Leu Asp Lys Leu Arg Gly Ser Ser Tyr Glu Ser Trp Val Asn
            260                 265                 270

Phe Asn Arg Tyr Arg Arg Glu Met Thr Leu Thr Val Leu Asp Leu Ile
        275                 280                 285

Ala Leu Phe Pro Leu Tyr Asp Val Arg Leu Tyr Pro Lys Glu Val Lys
    290                 295                 300

Thr Glu Leu Thr Arg Asp Val Leu Thr Asp Pro Ile Val Gly Val Asn
305                 310                 315                 320

Asn Leu Arg Gly Tyr Gly Thr Thr Phe Ser Asn Ile Glu Asn Tyr Ile
                325                 330                 335

Arg Lys Pro His Leu Phe Asp Tyr Leu His Arg Ile Gln Phe His Thr
            340                 345                 350

Arg Phe Gln Pro Gly Tyr Tyr Gly Asn Asp Ser Phe Asn Tyr Trp Ser
        355                 360                 365

Gly Asn Tyr Val Ser Thr Arg Pro Ser Ile Gly Ser Asn Asp Ile Ile
    370                 375                 380

Thr Ser Pro Phe Tyr Gly Asn Lys Ser Ser Glu Pro Val Gln Asn Leu
385                 390                 395                 400

Glu Phe Asn Gly Glu Lys Val Tyr Arg Ala Val Ala Asn Thr Asn Leu
                405                 410                 415

Ala Val Trp Pro Ser Ala Val Tyr Ser Gly Val Thr Lys Val Glu Phe
            420                 425                 430

Ser Gln Tyr Asn Asp Gln Thr Asp Glu Ala Ser Thr Gln Thr Tyr Asp
        435                 440                 445

Ser Lys Arg Asn Val Gly Ala Val Ser Trp Asp Ser Ile Asp Gln Leu
    450                 455                 460

Pro Pro Glu Thr Thr Asp Glu Pro Leu Glu Lys Gly Tyr Ser His Gln
465                 470                 475                 480

Leu Asn Tyr Val Met Cys Phe Leu Met Gln Gly Ser Arg Gly Thr Ile
                485                 490                 495

Pro Val Leu Thr Trp Thr His Lys Ser Val Asp Phe Phe Asn Met Ile
            500                 505                 510

Asp Ser Lys Lys Ile Thr Gln Leu Pro Leu Val Lys Ala Tyr Lys Leu
        515                 520                 525

Gln Ser Gly Ala Ser Val Val Ala Gly Pro Arg Phe Thr Gly Gly Asp
    530                 535                 540
```

```
Ile Ile Gln Cys Thr Glu Asn Gly Ser Ala Ala Thr Ile Tyr Val Thr
545                 550                 555                 560

Pro Asp Val Ser Tyr Ser Gln Lys Tyr Arg Ala Arg Ile His Tyr Ala
            565                 570                 575

Ser Thr Ser Gln Ile Thr Phe Thr Leu Ser Leu Asp Gly Ala Pro Phe
                580                 585                 590

Asn Gln Tyr Tyr Phe Asp Lys Thr Ile Asn Lys Gly Asp Thr Leu Thr
                595                 600                 605

Tyr Asn Ser Phe Asn Leu Ala Ser Phe Ser Thr Pro Phe Glu Leu Ser
        610                 615                 620

Gly Asn Asn Leu Gln Ile Gly Val Thr Gly Leu Ser Ala Gly Asp Lys
625                 630                 635                 640

Val Tyr Ile Asp Lys Ile Glu Phe Ile Pro Val Asn
                645                 650

<210> SEQ ID NO 13
<211> LENGTH: 652
<212> TYPE: PRT
<213> ORGANISM: Bacillus thuringiensis

<400> SEQUENCE: 13

Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
```

-continued

```
                260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
    290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
    370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
        435                 440                 445
His Val Ser Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
Thr Gln Leu Pro Val Val Lys Ala Tyr Ala Leu Ser Ser Gly Ala Ser
        515                 520                 525
Ile Ile Glu Gly Pro Gly Phe Thr Gly Gly Asn Leu Leu Phe Leu Lys
    530                 535                 540
Glu Ser Ser Asn Ser Ile Ala Lys Phe Lys Val Thr Leu Asn Ser Ala
545                 550                 555                 560
Ala Leu Leu Gln Arg Tyr Arg Val Arg Ile Arg Tyr Ala Ser Thr Thr
                565                 570                 575
Asn Leu Arg Leu Phe Val Gln Asn Ser Asn Asn Asp Phe Leu Val Ile
            580                 585                 590
Tyr Ile Asn Lys Thr Met Asn Lys Asp Asp Asp Leu Thr Tyr Gln Thr
        595                 600                 605
Phe Asp Leu Ala Thr Thr Asn Ser Asn Met Gly Phe Ser Gly Asp Lys
    610                 615                 620
Asn Glu Leu Ile Ile Gly Ala Glu Ser Phe Val Ser Asn Glu Lys Ile
625                 630                 635                 640
Tyr Ile Asp Lys Ile Glu Phe Ile Pro Val Gln Leu
                645                 650

<210> SEQ ID NO 14
<211> LENGTH: 1180
<212> TYPE: PRT
<213> ORGANISM: Bacillus thuringiensis
```

<400> SEQUENCE: 14

```
Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
            20                  25                  30

Asn Ser Pro Lys Gln Leu Leu Gln Ser Thr Asn Tyr Lys Asp Trp Leu
        35                  40                  45

Asn Met Cys Gln Gln Asn Gln Gln Tyr Gly Gly Asp Phe Glu Thr Phe
    50                  55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
                85                  90                  95

Phe Gly Thr Leu Ile Pro Val Leu Phe Pro Ala Gln Asp Gln Ser Asn
            100                 105                 110

Thr Trp Ser Asp Phe Ile Thr Gln Thr Lys Asn Ile Ile Lys Lys Glu
        115                 120                 125

Ile Ala Ser Thr Tyr Ile Ser Asn Ala Asn Lys Ile Leu Asn Arg Ser
    130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
                165                 170                 175

Val His Tyr His Phe Gln Asn Val Ile Pro Glu Leu Val Asn Ser Cys
            180                 185                 190

Pro Pro Asn Pro Ser Asp Cys Asp Tyr Asn Ile Leu Val Leu Ser
        195                 200                 205

Ser Tyr Ala Gln Ala Ala Asn Leu His Leu Thr Val Leu Asn Gln Ala
    210                 215                 220

Val Lys Phe Glu Ala Tyr Leu Lys Asn Asn Arg Gln Phe Asp Tyr Leu
225                 230                 235                 240

Glu Pro Leu Pro Thr Ala Ile Asp Tyr Tyr Pro Val Leu Thr Lys Ala
                245                 250                 255

Ile Glu Asp Tyr Thr Asn Tyr Cys Val Thr Thr Tyr Lys Lys Gly Leu
            260                 265                 270

Asn Leu Ile Lys Thr Thr Pro Asp Ser Asn Leu Asp Gly Asn Ile Asn
        275                 280                 285

Trp Asn Thr Tyr Asn Thr Tyr Arg Thr Lys Met Thr Thr Ala Val Leu
    290                 295                 300

Asp Leu Val Ala Leu Phe Pro Asn Tyr Asp Val Gly Lys Tyr Pro Ile
305                 310                 315                 320

Gly Val Gln Ser Glu Leu Thr Arg Glu Ile Tyr Gln Val Leu Asn Phe
                325                 330                 335

Glu Glu Ser Pro Tyr Lys Tyr Tyr Asp Phe Gln Tyr Gln Glu Asp Ser
            340                 345                 350

Leu Thr Arg Arg Pro His Leu Phe Thr Trp Leu Asp Ser Leu Asn Phe
        355                 360                 365

Tyr Glu Lys Ala Gln Thr Thr Pro Asn Asn Phe Phe Thr Ser His Tyr
    370                 375                 380

Asn Met Phe His Tyr Thr Leu Asp Asn Ile Ser Gln Lys Ser Ser Val
385                 390                 395                 400

Phe Gly Asn His Asn Val Thr Asp Lys Leu Lys Ser Leu Gly Leu Ala
```

-continued

```
            405                 410                 415
Thr Asn Ile Tyr Ile Phe Leu Leu Asn Val Ile Ser Leu Asp Asn Lys
            420                 425                 430

Tyr Leu Asn Asp Tyr Asn Asn Ile Ser Lys Met Asp Phe Phe Ile Thr
            435                 440                 445

Asn Gly Thr Arg Leu Leu Glu Lys Glu Leu Thr Ala Gly Ser Gly Gln
            450                 455                 460

Ile Thr Tyr Asp Val Asn Lys Asn Ile Phe Gly Leu Pro Ile Leu Lys
465                 470                 475                 480

Arg Arg Glu Asn Gln Gly Asn Pro Thr Leu Phe Pro Thr Tyr Asp Asn
            485                 490                 495

Tyr Ser His Ile Leu Ser Phe Ile Lys Ser Leu Ser Ile Pro Ala Thr
            500                 505                 510

Tyr Lys Thr Gln Val Tyr Thr Phe Ala Trp Thr His Ser Ser Val Asp
            515                 520                 525

Pro Lys Asn Thr Ile Tyr Thr His Leu Thr Thr Gln Ile Pro Ala Val
            530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
            565                 570                 575

Cys Gln His Ser Asn Phe Gln Ser Tyr Phe Ile Arg Ile Arg Tyr
            580                 585                 590

Ala Ser Asn Gly Ser Ala Asn Thr Arg Ala Val Ile Asn Leu Ser Ile
            595                 600                 605

Pro Gly Val Ala Glu Leu Gly Met Ala Leu Asn Pro Thr Phe Ser Gly
            610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
            645                 650                 655

Asn Arg Ser Asp Val Tyr Thr Asn Thr Thr Val Leu Ile Asp Lys Ile
            660                 665                 670

Glu Phe Leu Pro Ile Thr Arg Ser Ile Arg Glu Asp Arg Glu Lys Gln
            675                 680                 685

Lys Leu Glu Thr Val Gln Gln Ile Ile Asn Thr Phe Tyr Ala Asn Pro
            690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Glu Leu Tyr Pro Lys Glu
            725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
            755                 760                 765

Trp Thr Thr Ser Asp Asn Ile Thr Ile Gln Glu Asp Asp Pro Ile Phe
            770                 775                 780

Lys Gly His Tyr Leu His Met Ser Gly Ala Arg Asp Ile Asp Gly Thr
785                 790                 795                 800

Ile Phe Pro Thr Tyr Ile Phe Gln Lys Ile Asp Glu Ser Lys Leu Lys
            805                 810                 815

Pro Tyr Thr Arg Tyr Leu Val Arg Gly Phe Val Gly Ser Ser Lys Asp
            820                 825                 830
```

```
Val Glu Leu Val Val Ser Arg Tyr Gly Glu Ile Asp Ala Ile Met
        835                 840                 845

Asn Val Pro Ala Asp Leu Asn Tyr Leu Tyr Pro Ser Thr Phe Asp Cys
850                 855                 860

Glu Gly Ser Asn Arg Cys Glu Thr Ser Ala Val Pro Ala Asn Ile Gly
865                 870                 875                 880

Asn Thr Ser Asp Met Leu Tyr Ser Cys Gln Tyr Asp Thr Gly Lys Lys
        885                 890                 895

His Val Val Cys Gln Asp Ser His Gln Phe Ser Phe Thr Ile Asp Thr
            900                 905                 910

Gly Ala Leu Asp Thr Asn Glu Asn Ile Gly Val Trp Val Met Phe Lys
        915                 920                 925

Ile Ser Ser Pro Asp Gly Tyr Ala Ser Leu Asp Asn Leu Glu Val Ile
        930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
            965                 970                 975

Gln Ala Tyr Asp Val Ala Lys Gln Ala Ile Asp Ala Leu Phe Thr Asn
        980                 985                 990

Val Gln Asp Glu Ala Leu Gln Phe Asp Thr Thr Leu Ala Gln Ile Gln
        995                 1000                1005

Tyr Ala Glu Tyr Leu Val Gln Ser Ile Pro Tyr Val Tyr Asn Asp Trp
        1010                1015                1020

Leu Ser Asp Val Pro Gly Met Asn Tyr Asp Ile Tyr Val Glu Leu Asp
1025                1030                1035                1040

Ala Arg Val Ala Gln Ala Arg Tyr Leu Tyr Asp Thr Arg Asn Ile Ile
            1045                1050                1055

Lys Asn Gly Asp Phe Thr Gln Gly Val Met Gly Trp His Val Thr Gly
            1060                1065                1070

Asn Ala Asp Val Gln Gln Ile Asp Gly Val Ser Val Leu Val Leu Ser
        1075                1080                1085

Asn Trp Ser Ala Gly Val Ser Gln Asn Val His Leu Gln His Asn His
        1090                1095                1100

Gly Tyr Val Leu Arg Val Ile Ala Lys Lys Glu Gly Pro Gly Asn Gly
1105                1110                1115                1120

Tyr Val Thr Leu Met Asp Cys Glu Glu Asn Gln Glu Lys Leu Thr Phe
            1125                1130                1135

Thr Ser Cys Glu Glu Gly Tyr Ile Thr Lys Thr Val Asp Val Phe Pro
            1140                1145                1150

Asp Thr Asp Arg Val Arg Ile Glu Ile Gly Glu Thr Glu Gly Ser Phe
            1155                1160                1165

Tyr Ile Glu Ser Ile Glu Leu Ile Cys Met Asn Glu
        1170                1175                1180

<210> SEQ ID NO 15
<211> LENGTH: 1136
<212> TYPE: PRT
<213> ORGANISM: Bacillus thuringiensis

<400> SEQUENCE: 15

Met Asn Ser Gly Tyr Pro Leu Ala Asn Asp Leu Gln Gly Ser Met Lys
1               5                   10                  15

Asn Thr Asn Tyr Lys Asp Trp Leu Ala Met Cys Glu Asn Asn Gln Gln
```

-continued

```
                    20                  25                  30
Tyr Gly Val Asn Pro Ala Ala Ile Asn Ser Ser Val Ser Thr Ala
                35                  40                  45
Leu Lys Val Ala Gly Ala Ile Leu Lys Phe Val Asn Pro Ala Gly
            50                  55                  60
Thr Val Leu Thr Val Leu Ser Ala Val Leu Pro Ile Leu Trp Pro Thr
65                  70                  75                  80
Asn Thr Pro Thr Pro Glu Arg Val Trp Asn Asp Phe Met Thr Asn Thr
                85                  90                  95
Gly Asn Leu Ile Asp Gln Thr Val Thr Ala Tyr Val Arg Thr Asp Ala
                100                 105                 110
Asn Ala Lys Met Thr Val Val Lys Asp Tyr Leu Asp Gln Tyr Thr Thr
                115                 120                 125
Lys Phe Asn Thr Trp Lys Arg Glu Pro Asn Asn Gln Ser Tyr Arg Thr
                130                 135                 140
Ala Val Ile Thr Gln Phe Asn Leu Thr Ser Ala Lys Leu Arg Glu Thr
145                 150                 155                 160
Ala Val Tyr Phe Ser Asn Leu Val Gly Tyr Glu Leu Leu Leu Leu Pro
                165                 170                 175
Ile Tyr Ala Gln Val Ala Asn Phe Asn Leu Leu Ile Arg Asp Gly
                180                 185                 190
Leu Ile Asn Ala Gln Glu Trp Ser Leu Ala Arg Ser Ala Gly Asp Gln
                195                 200                 205
Leu Tyr Asn Thr Met Val Gln Tyr Thr Lys Glu Tyr Ile Ala His Ser
                210                 215                 220
Ile Thr Trp Tyr Asn Lys Gly Leu Asp Val Leu Arg Asn Lys Ser Asn
225                 230                 235                 240
Gly Gln Trp Ile Thr Phe Asn Asp Tyr Lys Arg Glu Met Thr Ile Gln
                    245                 250                 255
Val Leu Asp Ile Leu Ala Leu Phe Ala Ser Tyr Asp Pro Arg Arg Tyr
                260                 265                 270
Pro Ala Asp Lys Ile Asp Asn Thr Lys Leu Ser Lys Thr Glu Phe Thr
                275                 280                 285
Arg Glu Ile Tyr Thr Ala Leu Val Glu Ser Pro Ser Ser Lys Ser Ile
            290                 295                 300
Ala Ala Leu Glu Ala Ala Leu Thr Arg Asp Val His Leu Phe Thr Trp
305                 310                 315                 320
Leu Lys Arg Val Asp Phe Trp Thr Asn Thr Ile Tyr Gln Asp Leu Arg
                    325                 330                 335
Phe Leu Ser Ala Asn Lys Ile Gly Phe Ser Tyr Thr Asn Ser Ser Ala
                340                 345                 350
Met Gln Glu Ser Gly Ile Tyr Gly Ser Ser Gly Phe Gly Ser Asn Leu
                355                 360                 365
Thr His Gln Ile Gln Leu Asn Ser Asn Val Tyr Lys Thr Ser Ile Thr
            370                 375                 380
Asp Thr Ser Ser Pro Ser Asn Arg Val Thr Lys Met Asp Phe Tyr Lys
385                 390                 395                 400
Ile Asp Gly Thr Leu Ala Ser Tyr Asn Ser Asn Ile Thr Pro Thr Pro
                    405                 410                 415
Glu Gly Leu Arg Thr Thr Phe Phe Gly Phe Ser Thr Asn Glu Asn Thr
                420                 425                 430
Pro Asn Gln Pro Thr Val Asn Asp Tyr Thr His Ile Leu Ser Tyr Ile
                435                 440                 445
```

-continued

```
Lys Thr Asp Val Ile Asp Tyr Asn Ser Asn Arg Val Ser Phe Ala Trp
    450                 455                 460
Thr His Lys Ile Val Asp Pro Asn Asn Gln Ile Tyr Thr Asp Ala Ile
465                 470                 475                 480
Thr Gln Val Pro Ala Val Lys Ser Asn Phe Leu Asn Ala Thr Ala Lys
                485                 490                 495
Val Ile Lys Gly Pro Gly His Thr Gly Gly Asp Leu Val Ala Leu Thr
            500                 505                 510
Ser Asn Gly Thr Leu Ser Gly Arg Met Glu Ile Gln Cys Lys Thr Ser
            515                 520                 525
Ile Phe Asn Asp Pro Thr Arg Ser Tyr Gly Leu Arg Ile Arg Tyr Ala
        530                 535                 540
Ala Asn Ser Pro Ile Val Leu Asn Val Ser Tyr Val Leu Gln Gly Val
545                 550                 555                 560
Ser Arg Gly Thr Thr Ile Ser Thr Glu Ser Thr Phe Ser Arg Pro Asn
                565                 570                 575
Asn Ile Ile Pro Thr Asp Leu Lys Tyr Glu Glu Phe Arg Tyr Lys Asp
            580                 585                 590
Pro Phe Asp Ala Ile Val Pro Met Arg Leu Ser Ser Asn Gln Leu Ile
        595                 600                 605
Thr Ile Ala Ile Gln Pro Leu Asn Met Thr Ser Asn Asn Gln Val Ile
            610                 615                 620
Ile Asp Arg Ile Glu Ile Ile Pro Ile Thr Gln Ser Val Leu Asp Glu
625                 630                 635                 640
Thr Glu Asn Gln Asn Leu Glu Ser Glu Arg Glu Val Val Asn Ala Leu
                645                 650                 655
Phe Thr Asn Asp Ala Lys Asp Ala Leu Asn Ile Gly Thr Thr Asp Tyr
            660                 665                 670
Asp Ile Asp Gln Ala Ala Asn Leu Val Glu Cys Ile Ser Glu Glu Leu
        675                 680                 685
Tyr Pro Lys Glu Lys Met Leu Leu Leu Asp Glu Val Lys Asn Ala Lys
    690                 695                 700
Gln Leu Ser Gln Ser Arg Asn Val Leu Gln Asn Gly Asp Phe Glu Ser
705                 710                 715                 720
Ala Thr Leu Gly Trp Thr Thr Ser Asp Asn Ile Thr Ile Gln Glu Asp
                725                 730                 735
Asp Pro Ile Phe Lys Gly His Tyr Leu His Met Ser Gly Ala Arg Asp
            740                 745                 750
Ile Asp Gly Thr Ile Phe Pro Thr Tyr Ile Phe Gln Lys Ile Asp Glu
        755                 760                 765
Ser Lys Leu Lys Pro Tyr Thr Arg Tyr Leu Val Arg Gly Phe Val Gly
    770                 775                 780
Ser Ser Lys Asp Val Glu Leu Val Val Ser Arg Tyr Gly Glu Glu Ile
785                 790                 795                 800
Asp Ala Ile Met Asn Val Pro Ala Asp Leu Asn Tyr Leu Tyr Pro Ser
                805                 810                 815
Thr Phe Asp Cys Glu Gly Ser Asn Arg Cys Glu Thr Ser Ala Val Pro
            820                 825                 830
Ala Asn Ile Gly Asn Thr Ser Asp Met Leu Tyr Ser Cys Gln Tyr Asp
        835                 840                 845
Thr Gly Lys Lys His Val Val Cys Gln Asp Ser His Gln Phe Ser Phe
    850                 855                 860
```

```
Thr Ile Asp Thr Gly Ala Leu Asp Thr Asn Glu Asn Ile Gly Val Trp
865                 870                 875                 880

Val Met Phe Lys Ile Ser Ser Pro Asp Gly Tyr Ala Ser Leu Asp Asn
                885                 890                 895

Leu Glu Val Ile Glu Gly Pro Ile Asp Gly Glu Ala Leu Ser Arg
        900                 905                 910

Val Lys His Met Glu Lys Lys Trp Asn Asp Gln Met Glu Ala Lys Arg
        915                 920                 925

Ser Glu Thr Gln Gln Ala Tyr Asp Val Ala Lys Gln Ala Ile Asp Ala
        930                 935                 940

Leu Phe Thr Asn Val Gln Asp Glu Ala Leu Gln Phe Asp Thr Thr Leu
945                 950                 955                 960

Ala Gln Ile Gln Tyr Ala Glu Tyr Leu Val Gln Ser Ile Pro Tyr Val
                965                 970                 975

Tyr Asn Asp Trp Leu Ser Asp Val Pro Gly Met Asn Tyr Asp Ile Tyr
                980                 985                 990

Val Glu Leu Asp Ala Arg Val Ala Gln Ala Arg Tyr Leu Tyr Asp Thr
        995                 1000                1005

Arg Asn Ile Ile Lys Asn Gly Asp Phe Thr Gln Gly Val Met Gly Trp
        1010                1015                1020

His Val Thr Gly Asn Ala Asp Val Gln Gln Ile Asp Gly Val Ser Val
1025                1030                1035                1040

Leu Val Leu Ser Asn Trp Ser Ala Gly Val Ser Gln Asn Val His Leu
                1045                1050                1055

Gln His Asn His Gly Tyr Val Leu Arg Val Ile Ala Lys Lys Glu Gly
                1060                1065                1070

Pro Gly Asn Gly Tyr Val Thr Leu Met Asp Cys Glu Glu Asn Gln Glu
                1075                1080                1085

Lys Leu Thr Phe Thr Ser Cys Glu Gly Tyr Ile Thr Lys Thr Val
        1090                1095                1100

Asp Val Phe Pro Asp Thr Asp Arg Val Arg Ile Glu Ile Gly Glu Thr
1105                1110                1115                1120

Glu Gly Ser Phe Tyr Ile Glu Ser Ile Glu Leu Ile Cys Met Asn Glu
                1125                1130                1135

<210> SEQ ID NO 16
<211> LENGTH: 475
<212> TYPE: PRT
<213> ORGANISM: Bacillus thuringiensis

<400> SEQUENCE: 16

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110
```

Ala Ser Tyr Gly Phe Lys Val Ala Gly Asp Pro Ser Ile Lys Lys Asp
            115                 120                 125

Gly Tyr Phe Lys Lys Leu Gln Asp Glu Leu Asp Asn Ile Val Asp Asn
        130                 135                 140

Asn Ser Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Ser
    450                 455                 460

Asp Trp Tyr Asn Asn Ser Asp Trp Tyr Asn Asn
465                 470                 475

<210> SEQ ID NO 17
<211> LENGTH: 1138
<212> TYPE: PRT
<213> ORGANISM: Bacillus thuringiensis

<400> SEQUENCE: 17

Met Asn Leu Asn Asn Leu Asp Gly Tyr Glu Asp Ser Asn Arg Thr Leu

-continued

```
  1               5                  10                 15
Asn Asn Ser Leu Asn Tyr Pro Thr Gln Lys Ala Leu Ser Pro Ser Leu
                20                  25                 30
Lys Asn Met Asn Tyr Gln Asp Phe Leu Ser Ile Thr Glu Arg Glu Gln
                35                  40                 45
Pro Glu Ala Leu Ala Ser Gly Asn Thr Ala Ile Asn Thr Val Val Ser
                50                  55                 60
Val Thr Gly Ala Thr Leu Ser Ala Leu Gly Val Pro Gly Ala Ser Phe
 65                  70                 75                 80
Ile Thr Asn Phe Tyr Leu Lys Ile Ala Gly Leu Leu Trp Pro Glu Asn
                85                  90                 95
Gly Lys Ile Trp Asp Glu Phe Met Thr Glu Val Glu Ala Leu Ile Asp
                100                 105                110
Gln Lys Ile Glu Glu Tyr Val Arg Asn Lys Ala Ile Ala Glu Leu Asp
                115                 120                125
Gly Leu Gly Ser Ala Leu Asp Lys Tyr Gln Lys Ala Leu Ala Asp Trp
                130                 135                140
Leu Gly Lys Gln Asp Asp Pro Glu Ala Ile Leu Ser Val Ala Thr Glu
145                 150                 155                160
Phe Arg Ile Ile Asp Ser Leu Phe Glu Phe Ser Met Pro Ser Phe Lys
                165                 170                175
Val Thr Gly Tyr Glu Ile Pro Leu Leu Thr Val Tyr Ala Gln Ala Ala
                180                 185                190
Asn Leu His Leu Ala Leu Leu Arg Asp Ser Thr Leu Tyr Gly Asp Lys
                195                 200                205
Trp Gly Phe Thr Gln Asn Asn Ile Glu Glu Asn Tyr Asn Arg Gln Lys
                210                 215                220
Lys Arg Ile Ser Glu Tyr Ser Asp His Cys Thr Lys Trp Tyr Asn Ser
225                 230                 235                240
Gly Leu Ser Arg Leu Asn Gly Ser Thr Tyr Glu Gln Trp Ile Asn Tyr
                245                 250                255
Asn Arg Phe Arg Arg Glu Met Ile Leu Met Ala Leu Asp Leu Val Ala
                260                 265                270
Val Phe Pro Phe His Asp Pro Arg Arg Tyr Ser Met Glu Thr Ser Thr
                275                 280                285
Gln Leu Thr Arg Glu Val Tyr Thr Asp Pro Val Ser Leu Ser Ile Ser
                290                 295                300
Asn Pro Asp Ile Gly Pro Ser Phe Ser Gln Met Glu Asn Thr Ala Ile
305                 310                 315                320
Arg Thr Pro His Leu Val Asp Tyr Leu Asp Glu Leu Tyr Ile Tyr Thr
                325                 330                335
Ser Lys Tyr Lys Ala Phe Ser His Glu Ile Gln Pro Asp Leu Phe Tyr
                340                 345                350
Trp Ser Ala His Lys Val Ser Phe Lys Ser Glu Gln Ser Asn Leu
                355                 360                365
Tyr Thr Thr Gly Ile Tyr Gly Lys Thr Ser Gly Tyr Ile Ser Ser Gly
                370                 375                380
Ala Tyr Ser Phe His Gly Asn Asp Ile Tyr Arg Thr Leu Ala Ala Pro
385                 390                 395                400
Ser Val Val Val Tyr Pro Tyr Thr Gln Asn Tyr Gly Val Glu Gln Val
                405                 410                415
Glu Phe Tyr Gly Val Lys Gly His Val His Tyr Arg Gly Asp Asn Lys
                420                 425                430
```

-continued

```
Tyr Asp Leu Thr Tyr Asp Ser Ile Asp Gln Leu Pro Pro Asp Gly Glu
        435                 440                 445

Pro Ile His Glu Lys Tyr Thr His Arg Leu Cys His Ala Thr Ala Ile
    450                 455                 460

Phe Lys Ser Thr Pro Asp Tyr Asp Asn Ala Thr Ile Pro Ile Phe Ser
465                 470                 475                 480

Trp Thr His Arg Ser Ala Glu Tyr Tyr Asn Arg Ile Tyr Pro Asn Lys
                485                 490                 495

Ile Thr Lys Ile Pro Ala Val Lys Met Tyr Lys Leu Asp Asp Pro Ser
            500                 505                 510

Thr Val Val Lys Gly Pro Gly Phe Thr Gly Gly Asp Leu Val Lys Arg
        515                 520                 525

Gly Ser Thr Gly Tyr Ile Gly Asp Ile Lys Ala Thr Val Asn Ser Pro
    530                 535                 540

Leu Ser Gln Lys Tyr Arg Val Arg Val Arg Tyr Ala Thr Asn Val Ser
545                 550                 555                 560

Gly Gln Phe Asn Val Tyr Ile Asn Asp Lys Ile Thr Leu Gln Thr Lys
                565                 570                 575

Phe Gln Asn Thr Val Glu Thr Ile Gly Glu Gly Lys Asp Leu Thr Tyr
            580                 585                 590

Gly Ser Phe Gly Tyr Ile Glu Tyr Ser Thr Thr Ile Gln Phe Pro Asp
        595                 600                 605

Glu His Pro Lys Ile Thr Leu His Leu Ser Asp Leu Ser Asn Asn Ser
    610                 615                 620

Ser Phe Tyr Val Asp Ser Ile Glu Phe Ile Pro Val Asp Val Asn Tyr
625                 630                 635                 640

Ala Glu Lys Glu Lys Leu Glu Lys Ala Gln Lys Ala Val Asn Thr Leu
                645                 650                 655

Phe Thr Glu Gly Arg Asn Ala Leu Gln Lys Asp Val Thr Asp Tyr Lys
            660                 665                 670

Val Asp Gln Val Ser Ile Leu Val Asp Cys Ile Ser Gly Asp Leu Tyr
        675                 680                 685

Pro Asn Glu Lys Arg Glu Leu Gln Asn Leu Val Lys Tyr Ala Lys Arg
    690                 695                 700

Leu Ser Tyr Ser Arg Asn Leu Leu Leu Asp Pro Thr Phe Asp Ser Ile
705                 710                 715                 720

Asn Ser Ser Glu Glu Asn Gly Trp Tyr Gly Ser Asn Gly Ile Val Ile
                725                 730                 735

Gly Asn Gly Asp Phe Val Phe Lys Gly Asn Tyr Leu Ile Phe Ser Gly
            740                 745                 750

Thr Asn Asp Thr Gln Tyr Pro Thr Tyr Leu Tyr Gln Lys Ile Asp Glu
        755                 760                 765

Ser Lys Leu Lys Glu Tyr Thr Arg Tyr Lys Leu Lys Gly Phe Ile Glu
    770                 775                 780

Ser Ser Gln Asp Leu Glu Ala Tyr Val Ile Arg Tyr Asp Ala Lys His
785                 790                 795                 800

Arg Thr Leu Asp Val Ser Asp Asn Leu Leu Pro Asp Ile Leu Pro Glu
                805                 810                 815

Asn Thr Cys Gly Glu Pro Asn Arg Cys Ala Ala Gln Gln Tyr Leu Asp
            820                 825                 830

Glu Asn Pro Ser Pro Glu Cys Ser Ser Met Gln Asp Gly Ile Leu Ser
        835                 840                 845
```

-continued

```
Asp Ser His Ser Phe Ser Leu Asn Ile Asp Thr Gly Ser Ile Asn His
    850                 855                 860

Asn Glu Asn Leu Gly Ile Trp Val Leu Phe Lys Ile Ser Thr Leu Glu
865                 870                 875                 880

Gly Tyr Ala Lys Phe Gly Asn Leu Glu Val Ile Glu Asp Gly Pro Val
                885                 890                 895

Ile Gly Glu Ala Leu Ala Arg Val Lys Arg Gln Glu Thr Lys Trp Arg
            900                 905                 910

Asn Lys Leu Ala Gln Leu Thr Thr Glu Thr Gln Ala Ile Tyr Thr Arg
        915                 920                 925

Ala Lys Gln Ala Leu Asp Asn Leu Phe Ala Asn Ala Gln Asp Ser His
    930                 935                 940

Leu Lys Arg Asp Val Thr Phe Ala Glu Ile Ala Ala Ala Arg Lys Ile
945                 950                 955                 960

Val Gln Ser Ile Arg Glu Ala Tyr Met Ser Trp Leu Ser Val Val Pro
                965                 970                 975

Gly Val Asn His Pro Ile Phe Thr Glu Leu Ser Gly Arg Val Gln Arg
            980                 985                 990

Ala Phe Gln Leu Tyr Asp Val Arg Asn Val Val Arg Asn Gly Arg Phe
        995                 1000                1005

Leu Asn Gly Leu Ser Asp Trp Ile Val Thr Ser Asp Val Lys Val Gln
    1010                1015                1020

Glu Glu Asn Gly Asn Asn Val Leu Val Leu Asn Asn Trp Asp Ala Gln
1025                1030                1035                1040

Val Leu Gln Asn Val Lys Leu Tyr Gln Asp Arg Gly Tyr Ile Leu His
                1045                1050                1055

Val Thr Ala Arg Lys Ile Gly Ile Gly Glu Gly Tyr Ile Thr Ile Thr
            1060                1065                1070

Asp Glu Glu Gly His Thr Asp Gln Leu Arg Phe Thr Ala Cys Glu Glu
        1075                1080                1085

Ile Asp Ala Ser Asn Ala Phe Ile Ser Gly Tyr Ile Thr Lys Glu Leu
    1090                1095                1100

Glu Phe Phe Pro Asp Thr Glu Lys Val His Ile Glu Ile Gly Glu Thr
1105                1110                1115                1120

Glu Gly Ile Phe Leu Val Glu Ser Ile Glu Leu Phe Leu Met Glu Glu
                1125                1130                1135

Leu Cys
```

<210> SEQ ID NO 18
<211> LENGTH: 1157
<212> TYPE: PRT
<213> ORGANISM: Bacillus thuringiensis

<400> SEQUENCE: 18

```
Met Ser Pro Asn Asn Gln Asn Glu Tyr Glu Ile Ile Asp Ala Thr Pro
 1               5                  10                  15

Ser Thr Ser Val Ser Ser Asp Ser Asn Arg Tyr Pro Phe Ala Asn Glu
            20                  25                  30

Pro Thr Asp Ala Leu Gln Asn Met Asn Tyr Lys Asp Tyr Leu Lys Met
        35                  40                  45

Ser Gly Gly Glu Asn Pro Glu Leu Phe Gly Asn Pro Glu Thr Phe Ile
    50                  55                  60

Ser Ser Ser Thr Ile Gln Thr Gly Ile Gly Ile Val Gly Arg Ile Leu
65                  70                  75                  80
```

-continued

```
Gly Ala Leu Gly Val Pro Phe Ala Ser Gln Ile Ala Ser Phe Tyr Ser
                85                  90                  95
Phe Ile Val Gly Gln Leu Trp Pro Ser Lys Ser Val Asp Ile Trp Gly
            100                 105                 110
Glu Ile Met Glu Arg Val Glu Glu Leu Val Asp Gln Lys Ile Glu Lys
        115                 120                 125
Tyr Val Lys Asp Lys Ala Leu Ala Glu Leu Lys Gly Leu Gly Asn Ala
    130                 135                 140
Leu Asp Val Tyr Gln Gln Ser Leu Glu Asp Trp Leu Glu Asn Arg Asn
145                 150                 155                 160
Asp Ala Arg Thr Arg Ser Val Val Ser Asn Gln Phe Ile Ala Leu Asp
                165                 170                 175
Leu Asn Phe Val Ser Ser Ile Pro Ser Phe Ala Val Ser Gly His Glu
            180                 185                 190
Val Leu Leu Leu Ala Val Tyr Ala Gln Ala Val Asn Leu His Leu Leu
        195                 200                 205
Leu Leu Arg Asp Ala Ser Ile Phe Gly Glu Glu Trp Gly Phe Thr Pro
    210                 215                 220
Gly Glu Ile Ser Arg Phe Tyr Asn Arg Gln Val Gln Leu Thr Ala Glu
225                 230                 235                 240
Tyr Ser Asp Tyr Cys Val Lys Trp Tyr Lys Ile Gly Leu Asp Lys Leu
                245                 250                 255
Lys Gly Thr Thr Ser Lys Ser Trp Leu Asn Tyr His Gln Phe Arg Arg
            260                 265                 270
Glu Met Thr Leu Leu Val Leu Asp Leu Val Ala Leu Phe Pro Asn Tyr
        275                 280                 285
Asp Thr His Met Tyr Pro Ile Glu Thr Thr Ala Gln Leu Thr Arg Asp
    290                 295                 300
Val Tyr Thr Asp Pro Ile Ala Phe Asn Ile Val Thr Ser Thr Gly Phe
305                 310                 315                 320
Cys Asn Pro Trp Ser Thr His Ser Gly Ile Leu Phe Tyr Glu Val Glu
                325                 330                 335
Asn Asn Val Ile Arg Pro Pro His Leu Phe Asp Ile Leu Ser Ser Val
            340                 345                 350
Glu Ile Asn Thr Ser Arg Gly Gly Ile Thr Leu Asn Asn Asp Ala Tyr
        355                 360                 365
Ile Asn Tyr Trp Ser Gly His Thr Leu Lys Tyr Arg Arg Thr Ala Asp
    370                 375                 380
Ser Thr Val Thr Tyr Thr Ala Asn Tyr Gly Arg Ile Thr Ser Glu Lys
385                 390                 395                 400
Asn Ser Phe Ala Leu Glu Asp Arg Asp Ile Phe Glu Ile Asn Ser Thr
                405                 410                 415
Val Ala Asn Leu Ala Asn Tyr Tyr Gln Lys Ala Tyr Gly Val Pro Gly
            420                 425                 430
Ser Trp Phe His Met Val Lys Arg Gly Thr Ser Ser Thr Thr Ala Tyr
        435                 440                 445
Leu Tyr Ser Lys Thr His Thr Ala Leu Gln Gly Cys Thr Gln Val Tyr
    450                 455                 460
Glu Ser Ser Asp Glu Ile Pro Leu Asp Arg Thr Val Pro Val Ala Glu
465                 470                 475                 480
Ser Tyr Ser His Arg Leu Ser His Ile Thr Ser His Ser Phe Ser Lys
                485                 490                 495
Asn Gly Ser Ala Tyr Tyr Gly Ser Phe Pro Val Phe Val Trp Thr His
```

-continued

```
                500             505             510
Thr Ser Ala Asp Leu Asn Asn Thr Ile Tyr Ser Asp Lys Ile Thr Gln
        515                 520                 525

Ile Pro Ala Val Lys Gly Asp Met Leu Tyr Leu Gly Gly Ser Val Val
    530                 535                 540

Gln Gly Pro Gly Phe Thr Gly Gly Asp Ile Leu Lys Arg Thr Asn Pro
545                 550                 555                 560

Ser Ile Leu Gly Thr Phe Ala Val Thr Val Asn Gly Ser Leu Ser Gln
                565                 570                 575

Arg Tyr Arg Val Arg Ile Arg Tyr Ala Ser Thr Thr Asp Phe Glu Phe
            580                 585                 590

Thr Leu Tyr Leu Gly Asp Thr Ile Glu Lys Asn Arg Phe Asn Lys Thr
        595                 600                 605

Met Asp Asn Gly Ala Ser Leu Thr Tyr Glu Thr Phe Lys Phe Ala Ser
    610                 615                 620

Phe Ile Thr Asp Phe Gln Phe Arg Glu Thr Gln Asp Lys Ile Leu Leu
625                 630                 635                 640

Ser Met Gly Asp Phe Ser Ser Gly Gln Glu Val Tyr Ile Asp Arg Ile
                645                 650                 655

Glu Phe Ile Pro Val Asp Glu Thr Tyr Glu Ala Glu Gln Asp Leu Glu
            660                 665                 670

Ala Ala Lys Lys Ala Val Asn Ala Leu Phe Thr Asn Thr Lys Asp Gly
        675                 680                 685

Leu Arg Pro Gly Val Thr Asp Tyr Glu Val Asn Gln Ala Ala Asn Leu
    690                 695                 700

Val Glu Cys Leu Ser Asp Asp Leu Tyr Pro Asn Glu Lys Arg Leu Leu
705                 710                 715                 720

Phe Asp Ala Val Arg Glu Ala Lys Arg Leu Ser Gly Ala Arg Asn Leu
                725                 730                 735

Leu Gln Asp Pro Asp Phe Gln Glu Ile Asn Gly Glu Asn Gly Trp Ala
            740                 745                 750

Ala Ser Thr Gly Ile Glu Ile Val Glu Gly Asp Ala Val Phe Lys Gly
        755                 760                 765

Arg Tyr Leu Arg Leu Pro Gly Ala Arg Glu Ile Asp Thr Glu Thr Tyr
    770                 775                 780

Pro Thr Tyr Leu Tyr Gln Lys Val Glu Glu Gly Val Leu Lys Pro Tyr
785                 790                 795                 800

Thr Arg Tyr Arg Leu Arg Gly Phe Val Gly Ser Ser Gln Gly Leu Glu
                805                 810                 815

Ile Tyr Thr Ile Arg His Gln Thr Asn Arg Ile Val Lys Asn Val Pro
            820                 825                 830

Asp Asp Leu Leu Pro Asp Val Ser Pro Val Asn Ser Asp Gly Ser Ile
        835                 840                 845

Asn Arg Cys Ser Glu Gln Lys Tyr Val Asn Ser Arg Leu Glu Gly Glu
    850                 855                 860

Asn Arg Ser Gly Asp Ala His Glu Phe Ser Leu Pro Ile Asp Ile Gly
865                 870                 875                 880

Glu Leu Asp Tyr Asn Glu Asn Ala Gly Ile Trp Val Gly Phe Lys Ile
                885                 890                 895

Thr Asp Pro Glu Gly Tyr Ala Thr Leu Gly Asn Leu Glu Leu Val Glu
            900                 905                 910

Glu Gly Pro Leu Ser Gly Asp Ala Leu Glu Arg Leu Gln Arg Glu Glu
        915                 920                 925
```

Gln Gln Trp Lys Ile Gln Met Thr Arg Arg Glu Thr Asp Arg
            930                 935                 940

Arg Tyr Met Ala Ser Lys Gln Ala Val Asp Arg Leu Tyr Ala Asp Tyr
945                 950                 955                 960

Gln Asp Gln Gln Leu Asn Pro Asp Val Glu Ile Thr Asp Leu Thr Ala
                965                 970                 975

Ala Gln Asp Leu Ile Gln Ser Ile Pro Tyr Val Tyr Asn Glu Met Phe
            980                 985                 990

Pro Glu Ile Pro Gly Met Asn Tyr Thr Lys Phe Thr Glu Leu Thr Asp
            995                 1000                1005

Arg Leu Gln Gln Ala Trp Asn Leu Tyr Asp Gln Arg Asn Ala Ile Pro
    1010                1015                1020

Asn Gly Asp Phe Arg Asn Gly Leu Ser Asn Trp Asn Ala Thr Pro Gly
1025                1030                1035                1040

Val Glu Val Gln Gln Ile Asn His Thr Ser Val Leu Val Ile Pro Asn
                1045                1050                1055

Trp Asp Glu Gln Val Ser Gln Gln Phe Thr Val Gln Pro Asn Gln Arg
            1060                1065                1070

Tyr Val Leu Arg Val Thr Ala Arg Lys Glu Gly Val Gly Asn Gly Tyr
    1075                1080                1085

Val Ser Ile Arg Asp Gly Gly Asn Gln Ser Glu Thr Leu Thr Phe Ser
1090                1095                1100

Ala Ser Asp Tyr Asp Thr Asn Gly Val Tyr Asn Asp Gln Thr Gly Tyr
1105                1110                1115                1120

Ile Thr Lys Thr Val Thr Phe Ile Pro Tyr Thr Asp Gln Met Trp Ile
            1125                1130                1135

Glu Ile Ser Glu Thr Glu Gly Thr Phe Tyr Ile Glu Ser Val Glu Leu
            1140                1145                1150

Ile Val Asp Val Glu
        1155

<210> SEQ ID NO 19
<211> LENGTH: 675
<212> TYPE: PRT
<213> ORGANISM: Bacillus thuringiensis

<400> SEQUENCE: 19

Met Asn Pro Tyr Gln Asn Lys Asn Glu Tyr Glu Ile Phe Asn Ala Pro
1               5                   10                  15

Ser Asn Gly Phe Ser Lys Ser Asn Asn Tyr Ser Arg Tyr Pro Leu Ala
            20                  25                  30

Asn Lys Pro Asn Gln Pro Leu Lys Asn Thr Asn Tyr Lys Asp Trp Leu
        35                  40                  45

Asn Val Cys Gln Asp Asn Gln Gln Tyr Gly Asn Asn Ala Gly Asn Phe
    50                  55                  60

Ala Ser Ser Glu Thr Ile Val Gly Val Ser Ala Gly Ile Ile Val Val
65                  70                  75                  80

Gly Thr Met Leu Gly Ala Phe Ala Ala Pro Val Leu Ala Ala Gly Ile
                85                  90                  95

Ile Ser Phe Gly Thr Leu Leu Pro Ile Phe Trp Gln Gly Ser Asp Pro
            100                 105                 110

Ala Asn Val Trp Gln Asp Leu Leu Asn Ile Gly Gly Arg Pro Ile Gln
        115                 120                 125

Glu Ile Asp Lys Asn Ile Ile Asn Val Leu Thr Ser Ile Val Thr Pro

-continued

```
            130                 135                 140
Ile Lys Asn Gln Leu Asp Lys Tyr Gln Glu Phe Phe Asp Lys Trp Glu
145                 150                 155                 160

Pro Ala Arg Thr His Ala Asn Ala Lys Ala Val His Asp Leu Phe Thr
                165                 170                 175

Thr Leu Glu Pro Ile Ile Asp Lys Asp Leu Asp Met Leu Lys Asn Asn
            180                 185                 190

Ala Ser Tyr Arg Ile Pro Thr Leu Pro Ala Tyr Ala Gln Ile Ala Thr
                195                 200                 205

Trp His Leu Asn Leu Leu Lys His Ala Ala Thr Tyr Tyr Asn Ile Trp
210                 215                 220

Leu Gln Asn Gln Gly Ile Asn Pro Ser Thr Phe Asn Ser Ser Asn Tyr
225                 230                 235                 240

Tyr Gln Gly Tyr Leu Lys Arg Lys Ile Gln Glu Tyr Thr Asp Tyr Cys
                245                 250                 255

Ile Gln Thr Tyr Asn Ala Gly Leu Thr Met Ile Arg Thr Asn Thr Asn
                260                 265                 270

Ala Thr Trp Asn Met Tyr Asn Thr Tyr Arg Leu Glu Met Thr Leu Thr
            275                 280                 285

Val Leu Asp Leu Ile Ala Ile Phe Pro Asn Tyr Asp Pro Glu Lys Tyr
290                 295                 300

Pro Ile Gly Val Lys Ser Glu Leu Ile Arg Glu Val Tyr Thr Asn Val
305                 310                 315                 320

Asn Ser Asp Thr Phe Arg Thr Ile Thr Glu Leu Glu Asn Gly Leu Thr
                325                 330                 335

Arg Asn Pro Thr Leu Phe Thr Trp Ile Asn Gln Gly Arg Phe Tyr Thr
            340                 345                 350

Arg Asn Ser Arg Asp Ile Leu Asp Pro Tyr Asp Ile Phe Ser Phe Thr
            355                 360                 365

Gly Asn Gln Met Ala Phe Thr His Thr Asn Asp Asp Arg Asn Ile Ile
            370                 375                 380

Trp Gly Ala Val His Gly Asn Ile Ile Ser Gln Asp Thr Ser Lys Val
385                 390                 395                 400

Phe Pro Phe Tyr Arg Asn Lys Pro Ile Asp Lys Val Glu Ile Val Arg
                405                 410                 415

His Arg Glu Tyr Ser Asp Ile Ile Tyr Glu Met Ile Phe Phe Ser Asn
                420                 425                 430

Ser Ser Glu Val Phe Arg Tyr Ser Ser Asn Ser Thr Ile Glu Asn Asn
            435                 440                 445

Tyr Lys Arg Thr Asp Ser Tyr Met Ile Pro Lys Gln Thr Trp Lys Asn
450                 455                 460

Glu Glu Tyr Gly His Thr Leu Ser Tyr Ile Lys Thr Asp Asn Tyr Ile
465                 470                 475                 480

Phe Ser Val Val Arg Glu Arg Arg Val Ala Phe Ser Trp Thr His
                485                 490                 495

Thr Ser Val Asp Phe Gln Asn Thr Ile Asp Leu Asp Asn Ile Thr Gln
            500                 505                 510

Ile His Ala Leu Lys Ala Leu Lys Val Ser Ser Asp Ser Lys Ile Val
            515                 520                 525

Lys Gly Pro Gly His Thr Gly Gly Asp Leu Val Ile Leu Lys Asp Ser
            530                 535                 540

Met Asp Phe Arg Val Arg Phe Leu Lys Asn Val Ser Arg Gln Tyr Gln
545                 550                 555                 560
```

```
Val Arg Ile Arg Tyr Ala Thr Asn Ala Pro Lys Thr Thr Val Phe Leu
                565                 570                 575

Thr Gly Ile Asp Thr Ile Ser Val Glu Leu Pro Ser Thr Thr Ser Arg
            580                 585                 590

Gln Asn Pro Asn Ala Thr Asp Leu Thr Tyr Ala Asp Phe Gly Tyr Val
        595                 600                 605

Thr Phe Pro Arg Thr Val Pro Asn Lys Thr Phe Glu Gly Glu Asp Thr
    610                 615                 620

Leu Leu Met Thr Leu Tyr Gly Thr Pro Asn His Ser Tyr Asn Ile Tyr
625                 630                 635                 640

Ile Asp Lys Ile Glu Phe Ile Pro Ile Thr Gln Ser Val Leu Asp Tyr
                645                 650                 655

Thr Glu Lys Gln Asn Ile Glu Lys Thr Gln Lys Ile Val Asn Asp Leu
            660                 665                 670

Phe Val Asn
        675

<210> SEQ ID NO 20
<211> LENGTH: 648
<212> TYPE: PRT
<213> ORGANISM: Bacillus thuringiensis

<400> SEQUENCE: 20

Met His Tyr Tyr Gly Asn Arg Asn Glu Tyr Asp Ile Leu Asn Ala Ser
 1               5                  10                  15

Ser Asn Asp Ser Asn Met Ser Asn Thr Tyr Pro Arg Tyr Pro Leu Ala
            20                  25                  30

Asn Pro Gln Gln Asp Leu Met Gln Asn Thr Asn Tyr Lys Asp Trp Leu
        35                  40                  45

Asn Val Cys Glu Gly Tyr His Ile Glu Asn Pro Arg Glu Ala Ser Val
    50                  55                  60

Arg Ala Gly Leu Gly Lys Gly Leu Gly Ile Val Ser Thr Ile Val Gly
65                  70                  75                  80

Phe Phe Gly Gly Ser Ile Ile Leu Asp Thr Ile Gly Leu Phe Tyr Gln
                85                  90                  95

Ile Ser Glu Leu Leu Trp Pro Glu Asp Asp Thr Gln Gln Tyr Thr Trp
            100                 105                 110

Gln Asp Ile Met Asn His Val Glu Asp Leu Ile Asp Lys Arg Ile Thr
        115                 120                 125

Glu Val Ile Arg Gly Asn Ala Ile Arg Thr Leu Ala Asp Leu Gln Gly
    130                 135                 140

Lys Val Asp Asp Tyr Asn Asn Trp Leu Lys Lys Trp Lys Asp Asp Pro
145                 150                 155                 160

Lys Ser Thr Gly Asn Leu Ser Thr Leu Val Thr Lys Phe Thr Ala Leu
                165                 170                 175

Asp Ser Asp Phe Asn Gly Ala Ile Arg Thr Val Asn Asn Gln Gly Ser
            180                 185                 190

Pro Gly Tyr Glu Leu Leu Leu Leu Pro Val Tyr Ala Gln Ile Ala Asn
        195                 200                 205

Leu His Leu Leu Leu Leu Arg Asp Ala Gln Ile Tyr Gly Asp Lys Trp
    210                 215                 220

Trp Ser Ala Arg Ala Asn Ala Arg Asp Asn Tyr Tyr Gln Ile Gln Leu
225                 230                 235                 240

Glu Lys Thr Lys Glu Tyr Thr Glu Tyr Cys Ile Asn Trp Tyr Asn Lys
```

```
                245                 250                 255
Gly Leu Asn Asp Phe Arg Thr Ala Gly Gln Trp Val Asn Phe Asn Arg
            260                 265                 270

Tyr Arg Arg Glu Met Thr Leu Thr Val Leu Asp Ile Ile Ser Met Phe
            275                 280                 285

Pro Ile Tyr Asp Ala Arg Leu Tyr Pro Thr Glu Val Lys Thr Glu Leu
            290                 295                 300

Thr Arg Glu Ile Tyr Ser Asp Val Ile Asn Gly Glu Ile Tyr Gly Leu
305                 310                 315                 320

Met Thr Pro Tyr Phe Ser Phe Glu Lys Ala Glu Ser Leu Tyr Thr Arg
            325                 330                 335

Ala Pro His Leu Phe Thr Trp Leu Lys Gly Phe Arg Phe Val Thr Asn
            340                 345                 350

Ser Ile Ser Tyr Trp Thr Phe Leu Ser Gly Gly Gln Asn Lys Tyr Ser
            355                 360                 365

Tyr Thr Asn Asn Ser Ser Ile Asn Glu Gly Ser Phe Arg Gly Gln Asp
            370                 375                 380

Thr Asp Tyr Gly Gly Thr Ser Ser Thr Ile Asn Ile Pro Ser Asn Ser
385                 390                 395                 400

Tyr Val Tyr Asn Leu Trp Thr Glu Asn Tyr Glu Tyr Ile Tyr Pro Trp
            405                 410                 415

Gly Asp Pro Val Asn Ile Thr Lys Met Asn Phe Ser Val Thr Asp Asn
            420                 425                 430

Asn Ser Ser Lys Glu Leu Ile Tyr Gly Ala His Arg Thr Asn Lys Pro
            435                 440                 445

Val Val Arg Thr Asp Phe Asp Phe Leu Thr Asn Lys Glu Gly Thr Glu
            450                 455                 460

Leu Ala Lys Tyr Asn Asp Tyr Asn His Ile Leu Ser Tyr Met Leu Ile
465                 470                 475                 480

Asn Gly Glu Thr Phe Gly Gln Lys Arg His Gly Tyr Ser Phe Ala Phe
            485                 490                 495

Thr His Ser Ser Val Asp Pro Asn Asn Thr Ile Ala Ala Asn Lys Ile
            500                 505                 510

Thr Gln Ile Pro Val Val Lys Ala Ser Ser Ile Asn Gly Ser Ile Ser
            515                 520                 525

Ile Glu Lys Gly Pro Gly Phe Thr Gly Gly Asp Leu Val Lys Met Arg
            530                 535                 540

Ala Asp Ser Gly Leu Thr Met Arg Phe Lys Ala Glu Leu Leu Asp Lys
545                 550                 555                 560

Lys Tyr Arg Val Arg Ile Arg Tyr Lys Cys Asn Tyr Ser Ser Lys Leu
            565                 570                 575

Ile Leu Arg Lys Trp Lys Gly Glu Gly Tyr Ile Gln Gln Ile His
            580                 585                 590

Asn Ile Ser Pro Thr Tyr Gly Ala Phe Ser Tyr Leu Glu Ser Phe Thr
            595                 600                 605

Ile Thr Thr Thr Glu Asn Ile Phe Asp Leu Thr Met Glu Val Thr Tyr
            610                 615                 620

Pro Tyr Gly Arg Gln Phe Val Glu Asp Ile Pro Ser Leu Ile Leu Asp
625                 630                 635                 640

Lys Ile Glu Phe Leu Pro Thr Asn
            645

<210> SEQ ID NO 21
```

<211> LENGTH: 682
<212> TYPE: PRT
<213> ORGANISM: Bacillus thuringiensis

<400> SEQUENCE: 21

```
Met Asn Ser Tyr Gln Asn Lys Asn Glu Tyr Glu Ile Leu Asp Ala Lys
 1               5                  10                  15

Arg Asn Thr Cys His Met Ser Asn Cys Tyr Pro Lys Tyr Pro Leu Ala
            20                  25                  30

Asn Asp Pro Gln Met Tyr Leu Arg Asn Thr His Tyr Lys Asp Trp Ile
        35                  40                  45

Asn Met Cys Glu Glu Ala Ser Tyr Ala Ser Ser Gly Pro Ser Gln Leu
    50                  55                  60

Phe Lys Val Gly Gly Ser Ile Val Ala Lys Ile Leu Gly Met Ile Pro
65                  70                  75                  80

Glu Val Gly Pro Leu Leu Ser Trp Met Val Ser Leu Phe Trp Pro Thr
                85                  90                  95

Ile Glu Glu Lys Asn Thr Val Trp Glu Asp Met Ile Lys Tyr Val Ala
            100                 105                 110

Asn Leu Leu Lys Gln Glu Leu Thr Asn Asp Thr Leu Asn Arg Ala Thr
        115                 120                 125

Ser Asn Leu Ser Gly Leu Asn Glu Ser Leu Asn Ile Tyr Asn Arg Ala
    130                 135                 140

Leu Ala Ala Trp Lys Gln Asn Lys Asn Asn Phe Ala Ser Gly Glu Leu
145                 150                 155                 160

Ile Arg Ser Tyr Ile Asn Asp Leu His Ile Leu Phe Thr Arg Asp Ile
                165                 170                 175

Gln Ser Asp Phe Ser Leu Gly Gly Tyr Glu Thr Val Leu Leu Pro Ser
            180                 185                 190

Tyr Ala Ser Ala Ala Asn Leu His Leu Leu Leu Arg Asp Val Ala
        195                 200                 205

Ile Tyr Gly Lys Glu Leu Gly Tyr Pro Ser Thr Asp Val Glu Phe Tyr
    210                 215                 220

Tyr Asn Glu Gln Lys Tyr Tyr Thr Glu Lys Tyr Ser Asn Tyr Cys Val
225                 230                 235                 240

Asn Thr Tyr Lys Ser Gly Leu Glu Ser Lys Lys Gln Ile Gly Trp Ser
                245                 250                 255

Asp Phe Asn Arg Tyr Arg Glu Met Thr Leu Ser Val Leu Asp Ile
            260                 265                 270

Val Ala Leu Phe Pro Leu Tyr Asp Thr Gly Leu Tyr Pro Ser Lys Asp
        275                 280                 285

Gly Lys Ile His Val Lys Ala Glu Leu Thr Arg Glu Ile Tyr Ser Asp
    290                 295                 300

Val Ile Asn Asp His Val Tyr Gly Leu Met Val Pro Tyr Ile Ser Phe
305                 310                 315                 320

Glu His Ala Glu Ser Leu Tyr Thr Arg Arg Pro His Ala Phe Thr Trp
                325                 330                 335

Leu Lys Gly Phe Arg Phe Val Thr Asn Ser Ile Asn Ser Trp Thr Phe
            340                 345                 350

Leu Ser Gly Gly Glu Asn Arg Tyr Phe Leu Thr His Gly Glu Gly Thr
        355                 360                 365

Ile Tyr Asn Gly Pro Phe Leu Gly Gln Asp Thr Glu Tyr Gly Gly Thr
    370                 375                 380

Ser Ser Tyr Ile Asp Ile Ser Asn Asn Ser Ser Ile Tyr Asn Leu Trp
```

-continued

```
385                 390                 395                 400

Thr Lys Asn Tyr Glu Trp Ile Tyr Pro Trp Thr Asp Pro Val Asn Ile
                405                 410                 415

Thr Lys Ile Asn Phe Ser Ile Thr Asp Asn Ser Asn Ser Ser Glu Ser
            420                 425                 430

Ile Tyr Gly Ala Glu Arg Met Asn Lys Pro Thr Val Arg Thr Asp Phe
        435                 440                 445

Asn Phe Leu Leu Asn Arg Ala Gly Asn Gly Pro Thr Thr Tyr Asn Asp
    450                 455                 460

Tyr Asn His Ile Leu Ser Tyr Met Leu Ile Asn Gly Glu Thr Phe Gly
465                 470                 475                 480

Gln Lys Arg His Gly Tyr Ser Phe Ala Phe Thr His Ser Ser Val Asp
                485                 490                 495

Arg Tyr Asn Thr Ile Val Pro Asp Lys Ile Val Gln Ile Pro Ala Val
            500                 505                 510

Lys Thr Asn Leu Val Gly Ala Asn Ile Ile Lys Gly Pro Gly His Thr
        515                 520                 525

Gly Gly Asp Leu Leu Lys Leu Glu Tyr Glu Arg Phe Leu Ser Leu Arg
    530                 535                 540

Ile Lys Leu Ile Ala Ser Met Thr Phe Arg Ile Arg Ile Arg Tyr Ala
545                 550                 555                 560

Ser Asn Ile Ser Gly Gln Met Met Ile Asn Ile Gly Tyr Gln Asn Pro
                565                 570                 575

Thr Tyr Phe Asn Ile Ile Pro Thr Thr Ser Arg Asp Tyr Thr Glu Leu
            580                 585                 590

Lys Phe Glu Asp Phe Gln Leu Val Asp Thr Ser Tyr Ile Tyr Ser Gly
        595                 600                 605

Gly Pro Ser Ile Ser Ser Asn Thr Leu Trp Leu Asp Asn Phe Ser Asn
    610                 615                 620

Gly Pro Val Ile Ile Asp Lys Ile Glu Phe Ile Pro Leu Gly Ile Thr
625                 630                 635                 640

Leu Asn Gln Ala Gln Gly Tyr Asp Thr Tyr Asp Gln Asn Ala Asn Gly
                645                 650                 655

Met Tyr His Gln Asn Tyr Ser Asn Ser Gly Tyr Asn Tyr Asn Gln Glu
            660                 665                 670

Tyr Asn Thr Tyr Tyr Gln Ser Tyr Asn Asn
        675                 680

<210> SEQ ID NO 22
<211> LENGTH: 674
<212> TYPE: PRT
<213> ORGANISM: Bacillus thuringiensis

<400> SEQUENCE: 22

Met Asn Gln Tyr Gln Asn Lys Asn Glu Tyr Glu Ile Leu Glu Ser Ser
 1               5                  10                  15

Gln Asn Asn Met Asn Met Pro Asn Arg Tyr Pro Phe Ala Asp Asp Pro
            20                  25                  30

Asn Ala Val Met Lys Asn Gly Asn Tyr Lys Asp Trp Val Asn Glu Cys
        35                  40                  45

Glu Gly Ser Asn Ile Ser Pro Ser Pro Ala Ala Ala Ile Thr Ser Lys
    50                  55                  60

Ile Val Ser Ile Val Leu Lys Thr Leu Ala Lys Ala Val Ala Ser Ser
65                  70                  75                  80
```

```
Leu Ala Asp Ser Ile Lys Ser Ser Leu Gly Ile Ser Lys Thr Ile Thr
                85                  90                  95
Glu Asn Asn Val Ser Gln Val Ser Met Val Gln Val His Gln Ile Ile
               100                 105                 110
Asn Arg Arg Ile Gln Glu Thr Ile Leu Asp Leu Gly Glu Ser Ser Leu
               115                 120                 125
Asn Gly Leu Val Ala Ile Tyr Asn Arg Asp Tyr Leu Gly Ala Leu Glu
130                 135                 140
Ala Trp Asn Asn Asn Lys Ser Asn Ile Asn Tyr Gln Thr Asn Val Ala
145                 150                 155                 160
Glu Ala Phe Lys Thr Val Glu Arg Glu Phe Thr Lys Leu Lys Gly
               165                 170                 175
Ile Tyr Arg Thr Ser Ser Ser Gln Ile Thr Leu Leu Pro Thr Phe Thr
               180                 185                 190
Gln Ala Ala Asn Leu His Leu Ser Met Leu Arg Asp Ala Val Met Tyr
               195                 200                 205
Gln Glu Gly Trp Asn Leu Gln Ser His Ile Asn Tyr Ser Lys Glu Leu
               210                 215                 220
Asp Asp Ala Leu Glu Asp Tyr Thr Asn Tyr Cys Val Glu Val Tyr Thr
225                 230                 235                 240
Lys Gly Leu Asn Ala Leu Arg Gly Ser Thr Ala Ile Asp Trp Leu Glu
               245                 250                 255
Phe Asn Ser Phe Arg Arg Asp Met Thr Leu Met Val Leu Asp Leu Val
               260                 265                 270
Ala Ile Phe Pro Asn Tyr Asn Pro Val Arg Tyr Pro Leu Ser Thr Lys
               275                 280                 285
Ile Ser Leu Ser Arg Lys Ile Tyr Thr Asp Pro Val Gly Arg Thr Asp
               290                 295                 300
Ser Pro Ser Phe Gly Asp Trp Thr Asn Thr Gly Arg Thr Leu Ala Asn
305                 310                 315                 320
Phe Asn Asp Leu Glu Arg Glu Val Thr Asp Ser Pro Ser Leu Val Lys
               325                 330                 335
Trp Leu Gly Asp Met Thr Ile Tyr Thr Gly Ala Ile Asp Ser Tyr Arg
               340                 345                 350
Pro Thr Ser Pro Gly Asp Arg Ile Gly Val Trp Tyr Gly Asn Ile Asn
               355                 360                 365
Ala Phe Tyr His Thr Gly Arg Thr Asp Val Val Met Phe Arg Gln Thr
               370                 375                 380
Gly Asp Thr Ala Tyr Glu Asp Pro Ser Thr Phe Ile Ser Asn Ile Leu
385                 390                 395                 400
Tyr Asp Asp Ile Tyr Lys Leu Asp Leu Arg Ala Ala Ala Val Ser Thr
               405                 410                 415
Ile Gln Gly Ala Met Asp Thr Thr Phe Gly Val Ser Ser Ser Arg Phe
               420                 425                 430
Phe Asp Ile Arg Gly Arg Asn Gln Leu Tyr Gln Ser Asn Lys Pro Tyr
               435                 440                 445
Pro Ser Leu Pro Ile Thr Ile Thr Phe Pro Gly Glu Ser Ser Glu
               450                 455                 460
Gly Asn Ala Asn Asp Tyr Ser His Leu Leu Cys Asp Val Lys Ile Leu
465                 470                 475                 480
Gln Glu Asp Ser Ser Asn Ile Cys Glu Gly Arg Ser Ser Leu Leu Ser
               485                 490                 495
His Ala Trp Thr His Ala Ser Leu Asp Arg Asn Asn Thr Ile Leu Pro
```

```
                    500                 505                 510
Asp Glu Ile Thr Gln Ile Pro Ala Val Thr Ala Tyr Glu Leu Arg Gly
            515                 520                 525

Asn Ser Ser Val Val Ala Gly Pro Gly Ser Thr Gly Gly Asp Leu Val
        530                 535                 540

Lys Met Ser Tyr His Ser Val Trp Ser Phe Lys Val Tyr Cys Ser Glu
545                 550                 555                 560

Leu Lys Asn Tyr Arg Val Arg Ile Arg Tyr Ala Ser His Gly Asn Cys
                565                 570                 575

Gln Phe Leu Met Lys Arg Trp Pro Ser Thr Gly Val Ala Pro Arg Gln
            580                 585                 590

Trp Ala Arg His Asn Val Gln Gly Thr Phe Ser Asn Ser Met Arg Tyr
        595                 600                 605

Glu Ala Phe Lys Tyr Leu Asp Ile Phe Thr Ile Thr Pro Glu Glu Asn
    610                 615                 620

Asn Phe Ala Phe Thr Ile Asp Leu Glu Ser Gly Gly Asp Leu Phe Ile
625                 630                 635                 640

Asp Lys Ile Glu Phe Ile Pro Val Ser Gly Ser Ala Phe Glu Tyr Glu
                645                 650                 655

Gly Lys Gln Asn Ile Glu Lys Thr Gln Lys Ala Val Asn Asp Leu Phe
            660                 665                 670

Ile Asn

<210> SEQ ID NO 23
<211> LENGTH: 675
<212> TYPE: PRT
<213> ORGANISM: Bacillus thuringiensis

<400> SEQUENCE: 23

Met Asn Pro Tyr Gln Asn Lys Ser Glu Cys Glu Ile Leu Asn Ala Pro
1               5                  10                  15

Leu Asn Asn Ile Asn Met Pro Asn Arg Tyr Pro Phe Ala Asn Asp Pro
            20                  25                  30

Asn Ala Val Met Lys Asn Gly Asn Tyr Lys Asp Trp Leu Asn Glu Cys
        35                  40                  45

Asp Gly Ile Thr Pro Ser Ile Phe Gly Thr Leu Gly Val Leu Ala Ser
    50                  55                  60

Ile Val Ile Ser Thr Ile Asn Leu Ala Thr Ser Pro Ser Ile Gly Asp
65                  70                  75                  80

Ala Phe Ala Leu Val Ser Ser Ile Gly Glu Tyr Trp Pro Glu Thr Lys
                85                  90                  95

Thr Ser Phe Pro Leu Ser Val Ala Asp Val Asn Arg Leu Ile Arg Glu
            100                 105                 110

Ala Leu Asp Gln Asn Ala Ile Asn Arg Ala Thr Gly Lys Phe Asn Gly
        115                 120                 125

Leu Met Asp Thr Tyr Asn Thr Val Tyr Leu Lys Asn Leu Gln Asp Trp
    130                 135                 140

Tyr Asp Thr Arg Ile Pro Ala Asn Pro Gln Gly Asp Ser Gln Leu Arg
145                 150                 155                 160

Glu Ala Ala Arg Arg Ser Leu Glu Glu Ile Glu Arg Asp Phe Arg Lys
                165                 170                 175

Ala Leu Ala Gly Glu Phe Ala Glu Ala Gly Ser Gln Ile Val Leu Leu
            180                 185                 190

Pro Ile Tyr Ala Gln Ala Ala Asn Ile His Leu Leu Ile Leu Lys Asp
```

-continued

```
            195                 200                 205
Ala Met Gln Phe Arg Thr Asp Leu Gly Leu Ile Arg Pro Val Gly Val
    210                 215                 220
Pro Ile Thr Thr Ser Ala Glu Asp Pro Phe Glu Ser Glu Phe Leu Leu
225                 230                 235                 240
Arg Ile Lys Lys Tyr Thr Asp His Cys Ile Ser Tyr Tyr Asp Asp Gly
                245                 250                 255
Leu Ala Lys Ile Arg Ser Arg Gly Ser Asp Gly Glu Thr Trp Trp Glu
                260                 265                 270
Phe Asn Lys Phe Arg Arg Glu Met Thr Leu Thr Val Leu Asp Leu Val
            275                 280                 285
Ala Leu Tyr Pro Thr His Asn Ile Lys Leu Tyr Pro Ile Pro Thr Gln
    290                 295                 300
Thr Glu Leu Ser Arg Val Val Tyr Thr Asp Pro Val Gly Cys Phe Gly
305                 310                 315                 320
Asn Arg Lys Ser Asp Ile Phe Ser Arg Leu Asn Phe Asp Tyr Leu Glu
                325                 330                 335
Asn Arg Leu Thr Arg Pro Arg Glu Pro Phe Asn Tyr Leu Asn Ser Val
                340                 345                 350
Gln Leu Phe Ala Ser Thr Val Ser Asn Ser Asn Asn Gly Glu Val Leu
            355                 360                 365
Arg Gly Asn Leu Asn Lys Ile Met Phe Glu Gly Trp Thr Ala Ser
    370                 375                 380
Arg Ser Gly Asp Gly Val Thr Thr Gly Thr Pro Phe Ser Thr Met Asp
385                 390                 395                 400
Trp Ser Tyr Gly Trp Gly Tyr Pro Arg Lys His Tyr Ala Glu Ile Thr
                405                 410                 415
Ser Arg Ser Gln Ala Leu Pro Gly Leu Asn Asn Ser Ile His Val Ile
                420                 425                 430
Val Gly Ile Asp Ser Phe Arg Ala Ile Gly Pro Gly Gln Gly Asp
            435                 440                 445
His Thr Phe Ser Leu Pro Gly Gly Asp Met Tyr Asp Cys Gly Lys Val
    450                 455                 460
Gln Ile Asn Pro Leu Glu Asp Tyr Arg Asn Ser Asp His Trp Ile Ser
465                 470                 475                 480
Asp Met Met Thr Ile Asn Gln Ser Val Gln Leu Ala Ser Asn Pro Thr
                485                 490                 495
Gln Thr Phe Ala Phe Ser Ala Leu Ser Leu Gly Trp His His Ser Ser
                500                 505                 510
Ala Gly Asn Arg Asn Val Tyr Val Tyr Asp Lys Ile Thr Gln Ile Pro
            515                 520                 525
Ala Thr Lys Thr Val Arg Glu His Pro Met Ile Lys Gly Pro Gly Phe
    530                 535                 540
Thr Gly Gly Asp Leu Ala Asp Leu Ser Ser Asn Ser Asp Ile Leu Gln
545                 550                 555                 560
Tyr Asp Leu Arg Ser Asp Tyr Asp Asp Arg Leu Thr Glu Asp Val Pro
                565                 570                 575
Phe Arg Ile Arg Ile Arg Cys Ala Ser Ile Gly Val Ser Thr Ile Ser
                580                 585                 590
Val Asp Asn Trp Gly Ser Ser Pro Gln Val Thr Val Ala Ser Thr
            595                 600                 605
Ala Ala Ser Leu Asp Thr Leu Lys Tyr Glu Ser Phe Gln Tyr Val Ser
    610                 615                 620
```

```
Ile Pro Gly Asn Tyr Tyr Phe Asp Ser Ala Pro Arg Ile Arg Leu Leu
625                 630                 635                 640

Arg Gln Pro Gly Arg Leu Leu Val Asp Arg Ile Glu Ile Ile Pro Val
            645                 650                 655

Asn Phe Phe Pro Leu Ser Glu Gln Glu Asn Lys Ser Val Asp Ser Leu
            660                 665                 670

Phe Ile Asn
    675

<210> SEQ ID NO 24
<211> LENGTH: 659
<212> TYPE: PRT
<213> ORGANISM: Bacillus thuringiensis

<400> SEQUENCE: 24

Asn Ser Tyr Glu Asn Lys Asn Glu Tyr Glu Ile Leu Asn Asp Ser Lys
1               5                   10                  15

Lys Ser Asn Met Ser Asn Pro Tyr Leu Arg Tyr Pro Leu Ala Asn Asp
            20                  25                  30

Ser Leu Ala Ser Met Gln Asn Thr Asn Tyr Lys Asp Trp Leu Thr Met
        35                  40                  45

Cys Asp Arg Thr Asp Thr Asp Val Leu Ser Ser Arg Gly Ala Val Ser
50                  55                  60

Thr Gly Val Gly Met Leu Ser Thr Ile Leu Ser Leu Phe Gly Ile Pro
65                  70                  75                  80

Leu Ile Gly Glu Gly Ile Asp Leu Leu Leu Gly Ala Ala Asp Phe Leu
                85                  90                  95

Trp Pro Glu Ser Asp Gly Gly His Gln Tyr Thr Trp Glu Asp Leu Met
            100                 105                 110

Asn His Ile Glu Glu Leu Met Asp Glu Arg Leu Glu Thr Glu Lys Arg
        115                 120                 125

Thr Thr Ala Leu Asp Asp Leu Arg Gly Leu Lys Ala Leu Leu Gly Leu
130                 135                 140

Phe Arg Asp Ala Phe Asp Ser Trp Glu Lys Asn Gln Asn Asp Pro Ile
145                 150                 155                 160

Ala Lys Asn Arg Val Gly Gly Tyr Phe Glu Asp Val His Thr His Phe
                165                 170                 175

Val Lys Asp Met Ala Ser Ile Phe Ser Ala Thr Asn Tyr Glu Val Leu
            180                 185                 190

Leu Leu Pro Val Tyr Ala Gln Ala Ala Asn Leu His Leu Leu Leu Leu
        195                 200                 205

Arg Glu Gly Val Ile Tyr Gly Ser Arg Trp Gly Ile Ala Pro Ala Ala
210                 215                 220

Asp Phe Tyr His Asp Gln Leu Leu Lys Tyr Thr Ala Ile Tyr Ala Asn
225                 230                 235                 240

His Cys Val Thr Trp Tyr Asn Asn Gly Leu Ala Gln Gln Lys Glu Leu
                245                 250                 255

Phe Ala Lys Ser Pro Asn Trp Asn Arg Phe Asn Ala Tyr Arg Arg Asp
            260                 265                 270

Met Thr Ile Thr Val Leu Asp Ile Ile Ala Leu Phe Pro Thr Tyr Asp
        275                 280                 285

Ala Arg Leu Tyr Thr Lys Pro Ile Lys Thr Glu Leu Thr Arg Glu Ile
290                 295                 300

Tyr Ser Asp Val Leu Asn Leu Asp Val Tyr Gly Val Gln Gln Thr Asp
```

```
               305                 310                 315                 320
Leu Asn Lys Asn Glu Ala Ala Phe Thr Arg Ser Pro His Leu Val Thr
            325                 330                 335
Arg Leu Arg Gly Phe Asp Phe Tyr Thr Arg Thr Lys Tyr Ala Tyr Trp
            340                 345                 350
Arg Tyr Leu Ala Gly His Thr Asn Tyr Phe Ser Phe Thr Gly Asn Gly
            355                 360                 365
Thr Ile Tyr Ser Ser Ser Phe Asn Asn Trp Tyr Asp Thr Asp Met Thr
        370                 375                 380
Lys Ser Thr Ile Asn Ile Pro Asp Tyr Ala Asn Ile Tyr Lys Leu Trp
385                 390                 395                 400
Thr Lys Ser Tyr Thr Asn Ile Ser Pro Tyr Thr Asp Pro Val Gly Ile
                405                 410                 415
Ser Gln Met Gln Phe Ser Leu Thr Asn Asn Gln Gln Leu Thr Tyr Thr
            420                 425                 430
Gly Thr Ser Ala Pro Lys Tyr Pro Val Arg Glu Thr Phe Phe Glu Ile
            435                 440                 445
Pro Pro Thr Asp Glu Lys Pro Leu Thr Tyr Glu Asn Tyr Ser His Ile
        450                 455                 460
Leu Ser Tyr Met Thr Ser Ala Gln His Phe Gly Asp Lys Lys Ile Gly
465                 470                 475                 480
Tyr Thr Phe Ala Trp Met His Glu Ser Val Asp Phe Asp Asn Arg Val
                485                 490                 495
Asp Pro Asp Lys Ile Thr Gln Ile Pro Ala Val Lys Gly Asp Tyr Leu
            500                 505                 510
Gln Tyr Gly Tyr Val Lys Gln Gly Pro Gly His Thr Gly Gly Asp Leu
            515                 520                 525
Val Ser Met Ile Arg Thr Asp Arg Leu Gly Ile Asn Val Tyr Phe Pro
        530                 535                 540
Gln Pro Leu Asp Tyr Arg Ile Arg Ile Arg Tyr Ser Thr Ser Ser Asn
545                 550                 555                 560
Gly Tyr Leu Tyr Ile Tyr Ser Pro Asn Thr Lys Ile Val Tyr Leu Pro
                565                 570                 575
Pro Thr Thr Leu Val Asp Gly Gln Pro Thr Phe Asp Pro Met Asp Phe
            580                 585                 590
Ser Ala Phe Arg Val Val Glu Val Pro Ala Ser Phe Arg Ala Ser Val
            595                 600                 605
Ala Gly Tyr Thr Asn Phe Thr Ile Glu Ala Gly Phe Gly Pro Val Tyr
        610                 615                 620
Ile Asp Lys Ile Glu Phe Ile Pro Asp Asn Thr Thr Thr Leu Glu Tyr
625                 630                 635                 640
Glu Gly Gly Arg Asp Leu Glu Lys Thr Lys Asn Ala Val Asn Asp Leu
                645                 650                 655
Phe Thr Asn

<210> SEQ ID NO 25
<211> LENGTH: 666
<212> TYPE: PRT
<213> ORGANISM: Bacillus thuringiensis

<400> SEQUENCE: 25

Asn Ser Tyr Glu Asn Lys Asn Glu Tyr Glu Ile Leu Glu Ser Ser Ser
 1               5                  10                  15
Asn Asn Thr Asn Met Pro Asn Arg Tyr Pro Phe Ala Asn Asp Arg Asp
```

-continued

```
                  20                  25                  30
Met Ser Thr Met Ser Phe Asn Asp Cys Gln Gly Ile Ser Trp Asp Glu
             35                  40                  45

Ile Trp Glu Ser Ala Glu Thr Ile Thr Ser Ile Gly Ile Asp Leu Ile
 50                  55                  60

Glu Phe Leu Met Glu Pro Ser Leu Gly Gly Ile Asn Thr Leu Phe Ser
 65                  70                  75                  80

Ile Ile Gly Lys Leu Ile Pro Thr Asn His Gln Ser Val Ser Ala Leu
             85                  90                  95

Ser Ile Cys Asp Leu Leu Ser Ile Ile Arg Lys Glu Val Ala Asp Ser
            100                 105                 110

Val Leu Ser Asp Ala Ile Cys Arg Phe Leu Asp Gly Lys Leu Lys Asn
            115                 120                 125

Tyr Arg Glu Tyr Tyr Leu Pro Tyr Leu Glu Ala Trp Leu Lys Asp Gly
            130                 135                 140

Lys Pro Leu Gln Lys Thr Asn Asn Ser Asp Ile Gly Gln Leu Val Lys
145                 150                 155                 160

Tyr Phe Glu Leu Ser Glu Arg Asp Phe Asn Glu Ile Leu Gly Gly Ser
                165                 170                 175

Leu Ala Arg Asn Asn Ala Gln Ile Leu Leu Leu Pro Tyr Phe Cys Ala
            180                 185                 190

Ser Cys Lys Cys Gln Leu Leu Leu Arg Asp Ala Val Gln Tyr Glu
            195                 200                 205

Glu Gln Trp Phe Pro Phe Leu Ser Ala Glu Asn Val Arg Ser Glu Leu
            210                 215                 220

Ile Ser Pro Asn Ser Gly Cys Asp Phe Thr Gly Asp Tyr Tyr Glu Arg
225                 230                 235                 240

Leu Lys Cys Lys Ile Ala Glu Tyr Thr Asp Tyr Cys Glu Tyr Trp Tyr
                245                 250                 255

Gln Ala Gly Leu Asn Gln Ile Lys Gln Ala Gly Thr Gly Ala Asp Thr
            260                 265                 270

Trp Ala Lys Phe Asn Lys Phe Arg Arg Glu Met Thr Leu Thr Val Leu
            275                 280                 285

Asp Ile Ile Ala Ile Phe Gln Thr Tyr Asp Phe Lys Lys Tyr Pro Leu
290                 295                 300

Pro Thr His Val Glu Leu Thr Arg Glu Ile Tyr Thr Asp Pro Val Gly
305                 310                 315                 320

Tyr Ser Ser Gly Thr Tyr Ser Trp Leu Lys Tyr Trp Thr Gly Ala Phe
                325                 330                 335

Asn Thr Leu Glu Ala Asn Gly Thr Arg Gly Pro Gly Leu Val Thr Trp
            340                 345                 350

Leu Arg Ser Ile Gly Ile Tyr Asn Glu Tyr Val Ser Arg Tyr Phe Ser
            355                 360                 365

Gly Trp Val Gly Thr Arg His Tyr Glu Asp Tyr Thr Thr Gly Asn Gly
            370                 375                 380

Asn Phe Gln Arg Met Ser Gly Thr Thr Ser Asn Asp Leu Arg Asp Ile
385                 390                 395                 400

Ser Phe Pro Asn Ser Asp Ile Phe Lys Ile Glu Ser Lys Ala Ile Met
                405                 410                 415

Asn Leu Val Gly Glu Ile Asn Ala Arg Pro Glu Tyr Arg Val Ser Arg
            420                 425                 430

Ala Glu Phe Ser Glu Ser Thr Ala Phe Ile Tyr Leu Tyr Asp Ala Gly
            435                 440                 445
```

```
Asn Ser Gly Leu Ser Ser Met Thr Ile Thr Ser Lys Leu Pro Gly Ile
            450                 455                 460

Lys Asn Pro Glu Pro Ser Tyr Arg Asp Tyr Ser His Arg Leu Ser Asn
465                 470                 475                 480

Ala Ala Cys Val Gly Ala Gly Asn Ser Arg Ile Asn Val Tyr Gly Trp
                485                 490                 495

Thr His Thr Ser Met Ser Lys Tyr Asn Leu Ile Tyr Pro Asp Lys Ile
            500                 505                 510

Thr Gln Ile Pro Ala Val Lys Ala Phe Asp Ile Ser Asp Thr Gly Pro
        515                 520                 525

Gly Gln Val Ile Ala Gly Pro His Thr Gly Gly Asn Val Val Ser
    530                 535                 540

Leu Pro Tyr Tyr Ser Arg Leu Lys Ile Arg Leu Ile Pro Ala Ser Thr
545                 550                 555                 560

Asn Lys Asn Tyr Leu Val Arg Val Arg Tyr Thr Ser Thr Ser Asn Gly
                565                 570                 575

Arg Leu Leu Val Glu Arg Trp Ser Pro Ser Ser Ile Ile Asn Ser Tyr
            580                 585                 590

Phe Phe Leu Pro Ser Thr Gly Pro Gly Asp Ser Phe Gly Tyr Val Asp
        595                 600                 605

Thr Leu Val Thr Thr Phe Asn Gln Pro Gly Val Glu Ile Ile Ile Gln
    610                 615                 620

Asn Leu Asp Thr Pro Ile Asn Val Asp Lys Val Glu Phe Ile Pro Val
625                 630                 635                 640

Asn Ser Thr Ala Leu Glu Tyr Glu Gly Lys Gln Ser Leu Glu Lys Ala
                645                 650                 655

Gln Asp Val Val Asn Asp Leu Phe Val Lys
            660                 665

<210> SEQ ID NO 26
<211> LENGTH: 529
<212> TYPE: PRT
<213> ORGANISM: Bacillus thuringiensis

<400> SEQUENCE: 26

Val Asn Phe Met Leu Thr Ser Gly Ala Lys Asn Met Leu Lys Leu Glu
  1               5                  10                  15

Thr Thr Asp Tyr Glu Ile Asp Gln Met Ala Asn Ala Ile Glu Asn Met
                20                  25                  30

Ser Gly Glu Gln Tyr Ser Gln Glu Lys Met Met Gln Trp His Asp Ile
            35                  40                  45

Lys Tyr Ala Lys Gln Leu Ser Gln Ala Arg Asn Leu Leu Gln Asn Gly
 50                  55                  60

Asp Phe Glu Asp Leu Phe Ser Gly Trp Thr Thr Ser Asn Gln Met Ser
 65                  70                  75                  80

Ile Gln Ala Asp Asn Ala Thr Phe Lys Gly Asn Tyr Leu His Met Ser
                85                  90                  95

Gly Ala Arg Asp Ile Tyr Gly Thr Ile Phe Pro Thr Tyr Ile Tyr Gln
            100                 105                 110

Lys Ile Asp Glu Ser Lys Leu Lys Pro Tyr Thr Arg Tyr Leu Val Arg
        115                 120                 125

Gly Phe Val Gly Ser Ser Lys Asp Leu Glu Leu Met Val Met Arg Tyr
    130                 135                 140

Gly Lys Glu Ile Asp Thr Val Met Asn Val Pro Asn Asp Ile Pro Tyr
```

```
            145                 150                 155                 160

Val Pro Ser Met Pro Val Cys Asn Glu Leu Tyr Asp Gly Gln Gln Pro
                165                 170                 175

Tyr Pro Asn Arg His Val Gly Tyr Tyr Asn Pro Met Pro Val Ser Gln
                180                 185                 190

Pro Ser Tyr Thr Ser Asp Thr Cys Gln Cys Thr Pro Gly Lys Lys His
                195                 200                 205

Val Val Cys His Asp Ser His Gln Phe Lys Phe His Ile Asp Thr Gly
        210                 215                 220

Glu Val Asp Tyr Asn Thr Asn Leu Gly Ile Trp Val Leu Phe Lys Ile
225                 230                 235                 240

Ser Ser Pro Asp Gly Tyr Ala Thr Leu Asp Asn Leu Glu Val Ile Glu
                245                 250                 255

Glu Gly Pro Val Arg Gly Glu Ala Val Thr His Val Lys Gln Lys Glu
                260                 265                 270

Lys Lys Trp Asn Gln Gln Met Glu Lys Arg Met Glu Thr Lys Arg
                275                 280                 285

Val Tyr Asp Arg Ala Lys Gln Ala Val Asp Ala Leu Phe Thr Gly Glu
                290                 295                 300

Glu Leu Asn Tyr Asp Val Thr Leu Ser His Ile Lys Asn Ala Asp Asp
305                 310                 315                 320

Leu Val Gln Ser Ile Pro Tyr Val His Asn Glu Trp Leu Pro Asp Phe
                325                 330                 335

Pro Gly Met Asn Tyr Asp Ile Tyr Gln Glu Leu Asn Ala Arg Ile Met
                340                 345                 350

Gln Ala Arg Tyr Leu Tyr Asp Ala Arg Asn Val Ile Thr Asn Gly Asp
                355                 360                 365

Phe Ala Gln Gly Leu Gln Gly Trp His Ala Glu Gly Lys Val Glu Val
                370                 375                 380

Gln Gln Met Asn Gly Thr Ser Val Leu Val Leu Ser Asn Trp Ser Ser
385                 390                 395                 400

Gly Val Ser Gln Asn Leu His Val Gln His Pro His Gly Tyr Leu Leu
                405                 410                 415

Arg Val Ser Ala Lys Lys Glu Gly Ser Gly Lys Gly Tyr Val Thr Arg
                420                 425                 430

Met Ser Cys Asn Gly Lys Gln Glu Thr Leu Thr Phe Thr Ser Cys Asp
                435                 440                 445

Gly Gly Tyr Met Thr Lys Thr Val Glu Val Phe Pro Glu Ser Asp Arg
                450                 455                 460

Val Arg Ile Glu Ile Gly Glu Thr Glu Gly Ser Phe Tyr Ile Glu Ser
465                 470                 475                 480
```

```
Ile Glu Leu Ile Cys Met Asn Gly Tyr Thr Ser Asn Asn Gln Asn
            485                 490                 495

Met Ser Asn Met Tyr Asp Gln Ser Tyr Ser Gly Asn Tyr Ser Gln Asn
            500                 505                 510

Thr Ser Asp Met Tyr Asp Gln Gly Gly Ser Val Ala Lys Phe Glu Lys
            515                 520                 525

Glu

<210> SEQ ID NO 27
<211> LENGTH: 558
<212> TYPE: PRT
<213> ORGANISM: Bacillus thuringiensis

<400> SEQUENCE: 27

Met Phe Ile Ser Asn Ile Lys Asn Thr Leu Lys Ile Glu Thr Thr Asp
  1               5                  10                  15

Tyr Glu Ile Asp Gln Ala Ala Ile Ser Ile Glu Cys Met Ser Asn Glu
                 20                  25                  30

His Ser Ser Lys Glu Glu Met Met Leu Trp Asp Glu Val Lys Gln Ala
             35                  40                  45

Lys Gln Leu Ser Trp Ser Arg Asn Leu Leu Tyr Asn Gly Asp Phe Glu
         50                  55                  60

Asp Val Ser Asn Gly Trp Lys Thr Ser Asn Thr Ile Glu Ile Arg Glu
 65                  70                  75                  80

Asn Ser Pro Val Phe Lys Gly His Tyr Leu His Met Phe Gly Ala Arg
                 85                  90                  95

Asp Ile Asp Gly Thr Leu Phe Pro Thr Tyr Ile Tyr Gln Lys Ile Glu
            100                 105                 110

Glu Ser Lys Leu Lys Pro Tyr Thr Arg Tyr Arg Val Arg Gly Phe Val
            115                 120                 125

Gly Ser Ser Lys Asp Leu Lys Leu Met Val Thr Arg Tyr Gly Lys Glu
        130                 135                 140

Ile Asp Ala Met Met Asn Val Pro Asn Asp Leu Ala Tyr Met Gln Pro
145                 150                 155                 160

Thr Pro Ser Cys Gly Asp Ser Arg Cys Glu Ser Ser Arg Tyr Val
                165                 170                 175

Ser Gln Gly Tyr Pro Thr Pro Val Thr Asp Gly Tyr Ala Ser Gly Arg
                180                 185                 190

Tyr Ala Cys Gln Ser Asn Arg Gly Thr Lys His Val Lys Cys His Asp
            195                 200                 205

Arg His Pro Phe Asp Phe His Ile Asp Thr Gly Glu Leu Asp Thr Asn
        210                 215                 220

Thr Asn Val Gly Ile Asp Val Leu Phe Lys Ile Ser Asn Pro Asp Gly
225                 230                 235                 240

Tyr Ala Thr Leu Gly Asn Leu Glu Val Ile Glu Glu Gly Pro Leu Thr
                245                 250                 255

Gly Glu Ala Leu Thr His Val Lys Gln Lys Glu Lys Lys Trp Lys Gln
            260                 265                 270

His Met Glu Lys Lys Arg Trp Glu Thr Gln Gln Ala Tyr Asp Pro Ala
        275                 280                 285

Lys Gln Ala Val Asp Ala Leu Phe Thr Asn Glu Gln Glu Leu His Tyr
    290                 295                 300

His Ile Thr Leu Asp His Ile Gln Asn Ala Asp Arg Leu Ile Gln Ala
305                 310                 315                 320
```

```
Ile Pro Tyr Val Tyr His Ala Trp Leu Pro Asp Ala Pro Gly Met Asn
                325                 330                 335

Tyr Asp Gly Tyr Gln Gly Leu Asn Ala Arg Ile Met Gln Ala Tyr Asn
            340                 345                 350

Leu Tyr Asp Ala Arg Asn Val Ile Thr Asn Gly Asp Phe Thr Gln Gly
        355                 360                 365

Leu Thr Gly Trp His Ala Ala Gly Lys Ala Met Val Gln Gln Met Asp
    370                 375                 380

Gly Ala Ser Val Leu Val Leu Ser Asn Trp Ser Ala Gly Val Ser Gln
385                 390                 395                 400

Asn Leu His Val Gln Glu His Gly Tyr Met Leu Arg Val Ile Ala
                405                 410                 415

Lys Lys Glu Gly Pro Gly Lys Gly Tyr Val Thr Met Met Asp Cys Asn
                420                 425                 430

Gly Asn Arg Glu Thr Leu Lys Phe Thr Ser Cys Glu Glu Gly Tyr Met
            435                 440                 445

Thr Lys Thr Val Glu Val Phe Pro Glu Ser Asp Arg Val Arg Ile Glu
        450                 455                 460

Ile Gly Glu Thr Glu Gly Thr Phe Tyr Val Asp Ser Ile Glu Leu Leu
465                 470                 475                 480

Cys Met Gln Gly Tyr Ala Ser Asn Asn Pro His Thr Gly Asn Met
                485                 490                 495

Tyr Gly Gln Ser Tyr Asn Gly Asn Tyr Asn Gln Asn Thr Ser Asp Val
            500                 505                 510

Tyr His Gln Gly Tyr Thr Asn Asn Tyr Asn Gln Asn Ser Ser Asn Met
        515                 520                 525

Tyr Asn Gln Asn Tyr Thr His Asn Asp Asp Leu His Ser Gly Cys Thr
    530                 535                 540

Cys Asn Gln Gly His Asn Ser Gly Cys Thr Cys Ser Gln Gly
545                 550                 555

<210> SEQ ID NO 28
<211> LENGTH: 558
<212> TYPE: PRT
<213> ORGANISM: Bacillus thuringiensis

<400> SEQUENCE: 28

Met Phe Thr Asn Gly Thr Lys Asn Thr Leu Lys Ile Glu Thr Thr Asp
  1               5                  10                  15

Tyr Glu Ile Asp Gln Ala Ala Ile Ser Ile Glu Cys Met Ser Asp Glu
             20                  25                  30

His Ser Pro Lys Glu Lys Met Met Leu Trp Asp Glu Val Lys Arg Ala
         35                  40                  45

Lys Leu Leu Ser Gln Ser Arg Asn Leu Leu Gln Asn Gly Asp Phe Gly
     50                  55                  60

Asp Phe Tyr Gly Asn Asp Trp Lys Phe Gly Asn Asn Ile Ile Ile Gly
 65                  70                  75                  80

Ser Asn Asn Ser Ile Phe Lys Gly Asn Phe Leu Gln Met Ser Gly Ala
                 85                  90                  95

Arg Asp Ile Tyr Gly Thr Ile Phe Pro Thr Tyr Ile Tyr Gln Lys Ile
            100                 105                 110

Asp Glu Ser Lys Leu Lys Pro Tyr Thr Arg Tyr Arg Val Arg Gly Phe
        115                 120                 125

Val Gly Ser Ser Lys Asp Leu Arg Leu Met Val Thr Arg Tyr Gly Lys
```

-continued

```
            130                 135                 140
Glu Ile Asp Ala Met Met Asn Val Pro Asn Asp Leu Ala Tyr Met Gln
145                 150                 155                 160

Pro Asn Pro Ser Cys Gly Asp Ser Arg Cys Glu Ser Ser Gln Tyr
            165                 170                 175

Val Ser Gln Gly Tyr Pro Thr Pro Thr Asp Gly Tyr Ala Pro Asp Arg
            180                 185                 190

Tyr Ala Cys Pro Ser Ser Ser Asp Lys Lys His Val Met Cys His Asp
            195                 200                 205

Arg His Pro Phe Asp Phe His Ile Asp Thr Gly Glu Leu Asp Thr Asn
            210                 215                 220

Thr Asn Val Gly Ile Asp Val Leu Phe Lys Ile Ser Asn Pro Asp Gly
225                 230                 235                 240

Tyr Ala Thr Leu Gly Asn Leu Glu Val Ile Glu Gly Pro Leu Thr
            245                 250                 255

Gly Glu Ala Leu Thr His Val Lys Gln Lys Glu Lys Lys Trp Lys Gln
            260                 265                 270

His Met Glu Lys Lys Arg Trp Glu Thr Gln Gln Ala Tyr Asp Pro Ala
            275                 280                 285

Lys Gln Ala Val Asp Thr Leu Phe Thr Asn Glu Gln Glu Leu His Tyr
            290                 295                 300

His Ile Thr Leu Asp Tyr Ile Gln Thr Leu Ile Asp Trp Tyr Ser Arg
305                 310                 315                 320

Phe Pro Ile Tyr Thr Met Thr Gly Tyr Arg Asp Ala Pro Gly Met Asn
            325                 330                 335

Tyr Asp Gly Tyr Gln Gly Leu Asn Ala Arg Ile Met Gln Ala Tyr Asn
            340                 345                 350

Leu Tyr Asp Ala Arg Asn Val Ile Thr Asn Gly Asp Phe Thr Lys Gly
            355                 360                 365

Leu Gln Gly Trp His Ala Ala Gly Lys Ala Ala Val Gln Gln Ile Asp
            370                 375                 380

Gly Ala Ser Val Leu Val Leu Ser Asn Trp Ser Ala Gly Val Ser Gln
385                 390                 395                 400

Asn Leu His Ala Gln Asp His His Gly Tyr Met Leu Arg Val Ile Ala
            405                 410                 415

Lys Lys Glu Gly Pro Gly Lys Gly Tyr Val Thr Met Met Asp Cys Asn
            420                 425                 430

Gly Asn Gln Glu Thr Leu Lys Phe Thr Ser Cys Glu Glu Gly Tyr Met
            435                 440                 445

Thr Lys Thr Val Glu Val Phe Pro Glu Ser Asp Arg Val Arg Ile Glu
            450                 455                 460

Ile Gly Glu Thr Glu Gly Thr Phe Tyr Val Asp Ser Ile Glu Leu Leu
465                 470                 475                 480

Cys Met Gln Gly Tyr Ala Ser Asn Asn Pro His Thr Gly Asn Met
            485                 490                 495

Tyr Gly Gln Ser Tyr Asn Gly Asn Tyr Asn Gln Asn Thr Ser Asp Val
            500                 505                 510
```

```
Tyr His Gln Gly Tyr Thr Asn Asn Tyr Asn Gln Asn Ser Ser Asn Met
        515                 520                 525

Tyr Asn Gln Asn Tyr Thr His Asn Asp Asp Leu His Ser Gly Cys Thr
    530                 535                 540

Cys Asn Gln Gly His Asn Ser Gly Cys Thr Cys Ser Gln Gly
545                 550                 555
```